US007345078B2

(12) United States Patent
Tepe et al.

(10) Patent No.: US 7,345,078 B2

(45) Date of Patent: *Mar. 18, 2008

(54) NF-κB INHIBITORS AND USES THEREOF

(75) Inventors: Jetze J. Tepe, East Lansing, MI (US); Satyamaheshwar Peddibhotla, College Station, TX (US)

(73) Assignee: The Board of Trustees of Michigan State University, Lansing, MI (US)

( * ) Notice: Subject to any disclaimer, the term of this patent is extended or adjusted under 35 U.S.C. 154(b) by 227 days.

This patent is subject to a terminal disclaimer.

(21) Appl. No.: 10/449,662

(22) Filed: May 30, 2003

(65) Prior Publication Data

US 2003/0232998 A1 Dec. 18, 2003

Related U.S. Application Data

(63) Continuation-in-part of application No. 10/347,323, filed on Jan. 17, 2003, now Pat. No. 6,878,735.

(60) Provisional application No. 60/385,162, filed on May 31, 2002.

(51) Int. Cl.
*A61K 31/4164* (2006.01)

(52) U.S. Cl. ....................................... 514/401; 514/402

(58) Field of Classification Search ................. 514/401
See application file for complete search history.

(56) References Cited

OTHER PUBLICATIONS

Golub et al., Science, vol. 286, Oct. 15, 1999, pp. 531-537.*

* cited by examiner

*Primary Examiner*—Laura L. Stockton
(74) *Attorney, Agent, or Firm*—Medlen & Carroll, LLP

(57) ABSTRACT

A new class of imidazolines as 4-position acids or esters with very potent anti-inflammatory as well as antimicrobial activity is described. The synthesis of these imidazolines includes a multicomponent reaction applicable to a combinatorial synthetic approach. The combination of these two key characteristics provides an effective therapeutic drug in the treatment of septic shock as well as many other inflammatory (arthritis and asthma) and infectious disorders. The use of this novel class of non-steroidal agents as anti-inflammatory agents (for the treatment of asthma, etc.), antibacterial agents, and antiseptic agents is described. The compounds are also useful in the treatment of tumors (such as cancers). The imidazolines are potent inhibitors of the transcription factor NF-κB as well as potent activity against the Gram (+) bacterium. The compositions are also useful for treating autoimmune diseases and for inhibiting rejection of organ and tissue transplants.

7 Claims, 13 Drawing Sheets

1 (75%)

2 (78%)

3 (74%)

4 (65%)

5 (68%)

6 (76%)

7 (70%)

8 (72%)

9 (76%)

10 (75%)

11 (70%)

12 (60%)

13 (51%)

14 (66%)

15 (79%)

16 (60 %)

17 (60%)

18(55%)

19

20

28

29

30

31

32

33

28 (74%)

29 (72%)

30 (55%)

31 (76%)

32 (65%)

33 (75%)

34 (78%)

35 (55%)

36 (68%)

37 (75%)

38 (76%)

39 (70%)

40 (70%)

41 (51%)

42 (66%)

43 (not optimized)

44 (60%)

45 (79%)

46 (35%)

47 (15%)

48 (65%)

49 (60%)

50 (not optimized)

SEQUENCE LISTING

<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: NF-kB consensus oligonucleotide

<400> SEQUENCE: 1
agttgagggg actttcccag gc 22

NF-κB INHIBITORS AND USES THEREOF

CROSS-REFERENCE TO RELATED APPLICATION

This application is a continuation-in-part of U.S. patent application Ser. No. 10/347,323, filed Jan. 17, 2003 now U.S. Pat. No. 6,878,735, and which claims priority to U.S. Provisional Patent Application Ser. No. 60/385,162, filed May 31, 2002.

STATEMENT REGARDING FEDERALLY SPONSORED RESEARCH OR DEVELOPMENT

Not Applicable.

Reference to a "Computer Listing Appendix submitted on a Compact Disc"

Not Applicable.

BACKGROUND OF THE INVENTION (1) Field of the Invention

The present invention relates to novel multi-substituted 4-acid or alkyl ester or amide imidazolines and to a process for their preparation. In particular the present invention relates to the multi-substituted imidazolines containing a 4-acid or an ester group which inhibit NF-κB or NF-κB kinase, are anti-inflammatory and/or antimicrobial and/or chemopotentiator and/or chemosensitizers of anticancer agents and/or immune response inhibitors to foreign and endogenous NF-κB activators. The compositions are useful for treating inflammatory diseases, Alzheimer's disease, stroke atherosclerosis, restenosis, diabetes, glomerulophritis, cancer, Hodgkins disease, cachexia, inflammation associated with infection and certain viral infections, including acquired immune deficiency syndrome (AIDS), adult respiratory distress syndrome, Ataxia Telangiestasia, and a variety of skin related diseases. The compositions are also useful for treating autoimmune diseases and for inhibiting rejection of organ and tissue transplants.

(2) Description of Related Art

The mammalian nuclear transcription factor, NF-κB, is a multisubunit complex involved in the activation of gene transcription, including the regulation of apoptosis (programmed cell death) (Baeuerle, Henkel, Ann. Rev. Immunol., 12: 141-179 (1994); Baldwin, Ann. Rev. Immunol. 14, 649-683 (1996)). NF-kB exists mainly as a homodimer (p50/p50) or heterodimer (p50/p65) in the cytoplasm in the form of an inactive complex with the inhibitory IkB protein. Many cellular stimuli including antineoplastic agents (White, J. Biol. Chem. 272: 14914-14920 (1997); Baldwin, J. Clin. Invest. 107: 241-246 (2001); Hideshima et al., J. Biol. Chem. 277: 16639-16647 (2002); Bottero et al., Cancer Res. 61: 7785-7791 (2001); Um et al., Oncogene 20: 6048-6056 (2001); Weldon et al., Surgery 130: 143-150 (2001); Arlt et al., Oncogene 20: 859-868 (2001); Liu et al., J. Immunol. 166: 5407-5415 (2001); Kim et al., Biochem. Biophys. Res. Commun. 273: 140-146 (2000)), viruses (HIV-1, HTLV-1), inflammatory cytokines (TNF-α, IL-1), phorbol esters, bacterial products (LPS), and oxidative stress, result in the IKK mediated phosphorylation of IkB on serines 32 and 36, followed by ubiquitination and subsequent degradation by the 26S proteosome (Baeuerle and Henkel, Ann. Rev. Immunol. 12: 141-179 (1994). Degradation of IκB ensures the release of NF-kB. Upon release, NF-κB translocates into the nucleus where the subunits bind with specific DNA control elements and initiates gene transcription. During translocation, additional protein phosphorylation events are required for optimal gene transcription (Karin and Lin, Nat. Immunol. 3: 221-227 (2002); Zhong et al., Cell 89: 413-424 (1997); Sizemore et al., Mol. Cell Biol 19: 4798-4805 (1999); Madrid et al., Mol. Cell Biol 20: 1626-1638 (2000)). Even though the kinases responsible for this phosphorylation event are not yet clearly identified, increasing evidence suggests the involvement of the cyclin dependent kinase GSK-3 (Schwabe and Brenner, Am. J. Physiol. Gastrointest. Liver Physiol. 283: G204-211 (2002); Ali et al., Chem. Rev. 101: 2527-2540 (2001)). Inhibition of NF-κB mediated gene transcription can be accomplished through inhibition of phosphorylation of the inhibitory protein IκB, inhibition of IKB degradation, inhibition of NF-κB (p50/p65) nuclear translocation, the inhibition of NF-κB-DNA binding or NF-κB-mediated DNA transcription (for a comprehensive review on NF-κB inhibitors, see Epinat and Gilmore, Oncogene 18: 6896-6909 (1999)). Genes regulated by NF-κB activation are a number of cytokines (TNF, IL-1, IL-2, IL-6, IL-8, iNOS), chemokines, cell adhesion molecules, acute phase proteins, immunoregulatory proteins, eicosanoid metabolizing enzymes, and anti-apoptotic genes.

NF-κB activation plays a role in cancer related disease. NF-κB is activated by oncogenic ras (the most common defect in human tumors), TNF, ionizing radiation (radiation damage) and chemotherapeutic agents. Activation of NF-κB by these signals results in the upregulation of anti-apoptotic cell signals and can therefore result in tumor cell resistance to chemotherapy. Inhibition of NF-κB is therefore a possible treatment in sensitizing tumors to chemotherapeutic drugs and the potential of novel cancer therapies. Related information on this treatment is found in (Das and White, J. Biol. Chem. 272: 14914-14920 (1997); Baldwin, J. Clin Invest. 107: 241-246 (2001); Hideshima et al., J. Biol. Chem. 277: 16639-16647 (2002); Weldon et al., Surgery 130: 143-150 (2001); Arlt et al., Oncogene 20: 859-868 (2001); Crinelli et al., Blood Cells Mol. Dis. 26: 211-222 (2000); Mayo and Baldwin, Biochim. Biophys. Acta 1470: M55-62 (2000); Adams, Curr. Opin. Chem. Biol. 6: 493-500 (2002); Boland, Biochem. Soc. Trans. 29: 674-678 (2001); Chen et al., Am. J. Pathol. 159: 387-397 (2001); Cusack et al., Drug Resist. Updat. 2: 271-273 (1999); Darnell, Jr., Nat. Rev. Cancer 2: 740-749 (2002); Guttridge et al., Mol. Cell. Biol. 19: 5785-5799 (1999); Jones et al., Ann. Thorac. Surg. 70: 930-936 (2000); discussion 936-937; Orlowski et al., J. Clin. Oncol. 20: 4420-4427 (2002); Royds et al., Mol. Pathol. 51: 55-61 (1998); Shah et al., J. Cell. Biochem. 82: 110-122 (2001); Wang et al., Science, 274: 784-787 (1996)). NF-κB activation also plays a significant role in inflammation disorders. NF-κB is activated by TNF and other pro-inflammatory cytokines. Inhibition of NF-κB activation by non-toxic inhibitors could therefore have clinical use in the treatment of many inflammatory disorders, rheumatoid arthritis, inflammatory bowel disease, astma, chronic obstructive pulmonary disease (COPD) osteoarthritis, osteoporosis and fibrotic diseases. Related information on this can be found in (Feldmann et al., Ann. Rheum. Dis. 61: Suppl 2, ii13-18 (2002); Gerard and Rollins, Nat. Immunol. 2: 108-115 (2001); Hart et al., Am. J. Respir. Crit. Care Med. 158: 1585-1592 (1998); Lee and Burckart, J. Clin. Pharmacol. 38: 981-993 (1998); Makarov, Arthritis Res. 3: 200-206 (2001); Manna et al., J. Immunol. 163: 6800-6809 (1999); Miagkov et al., Proc. Natl. Acad. Sci. USA, 95, 13859-13864 (1998); Miossec, Cell Mol. Biol. (Noisy-le-grand), 47: 675-678 (2001); Roshak et al., Curr. Opin. Pharmacol. 2: 316-321 (2002); Tak and Firestein, J. Clin. Invest. 107: 7-11 (2001); Taylor, Mol. Biotechnol. 19: 153-168 (2001); Yamamoto and Gaynor, J. Clin. Invest. 107: 135-142 (2001); Zhang and Ghosh, J. Endotoxin Res. 6: 453-457 (2000)).

NF-κB activation plays a significant role in immune disorders (Ghosh et al., Ann. Rev. Immunol. 16: 225-260 (1998)). Activation of the NF-κB results in the active transcription of a great variety of genes encoding many immunologically relevant proteins (Baeuerle and Henkel, Ann. Rev. Immunol. 12: 141-179 (1994); Daelemans et al., Antivir. Chem. Chemother. 10: 1-14 (1999)). In the case of the human immunodeficiency virus (HIV) infection results in NF-κB activation, which results in regular viral persistence (Rabson, A. B., Lin, H. C. *Adv Pharmacol* , 48, 161-207 (2000); Pati, S., Foulke, J. S., Jr., Barabitskaya, O., Kim, J., Nair, B. C. et al. *J Virol* , 77, 5759-5773 (2003); Quivy, V., Adam, E., Collette, Y., Demonte, D., Chariot, A. et al. *J Virol,* 76, 11091-11103 (2002); Amini, S., Clavo, A., Nadraga, Y., Giordano, A., Khalili, K. et al. *Oncogene,* 21, 5797-5803 (2002); Takada, N., Sanda, T., Okamoto, H., Yang, J. P., Asamitsu, K. et al. *J Virol,* 76, 8019-8030 (2002); Chen-Park, F. E.; Huang, D. B., Noro, B., Thanos, D., Ghosh, G. *J Biol Chem,* 277, 24701-24708 (2002); Ballard, D. W. *Immunol Res,* 23, 157-166 (2001); Baldwin, A. S., Jr. *J Clin Invest,* 107, 3-6 (2001); Calzado, M. A., MacHo, A., Lucena, C., Munoz, E. *Clin Exp Immunol,* 120, 317-323 (2000); Roland, J., Berezov, A., Greene, M. I., Murali, R., Piatier-Tonneau, D. et al. *DNA Cell Biol,* 18, 819-828 (1999); Boykins, R. A., Mahieux, R., Shankavaram, U. T., Gho, Y. S., Lee, S. F. et al. *J Immunol,* 163, 15-20 (1999); Asin, S., Taylor, J. A., Trushin, S., Bren, G., Paya, C. V. *J Virol,* 73, 3893-3903 (1999); Sato, T., Asamitsu, K., Yang, J. P., Takahashi, N., Tetsuka, T. et al. *AIDS Res Hum Retroviruses,* 14, 293-298 (1998)). HIV-1 replication is regulated through an variety of viral proteins as well as cellular transcription factors (in particular NF-κB) that interact with the viral long terminal repeat (LTR) (Asin, S., Taylor, J. A., Trushin, S., Bren, G., Paya, C. V. *J Virol,* 73, 3893-3903 (1999)). HIV-1 is able to enter a latent state in which the integrated provirus remains transcriptionally silent. The ability to continue to infect cells latently aids the virus to establish persistent infections and avoid the host immune system. The latent virus can establish large reservoirs of genetic variants in T-cells residing in lymphoid tissue. In addition, a recent study implicates NF-κB with the reactivation of latent HIV in T-cells in patents undergoing antiviral therapy (Finzi, D., Hermankova, M., Pierson, T., Carruth, L. M.,; Buck, C. et al. *Science,* 278, 1295-1300 (1997)). Relevant patent is this area are EP 0931544 A2 to Baba et al. and WO 02/30423 A1 to Callahan et al.

Chronic airway inflammation as seen with asthma, is associated with the over expression of inflammatory proteins called cytokines. In addition, other inflammatory mediators, such as IL-1 and TNF, play a major role in joint diseases such as rheumatoid arthritis. All of these inflammatory proteins are highly regulated by the nuclear transcription factor kappa B (NF-κB) (Yamamoto, Y., et al., J. Clin Invest 107 135-142 (2001); and Hart, L. A., et al., Am J Respir Crit Care Med 158 1585-1592 (1998)). Inhibition of this regulatory protein or its kinase by anti-inflammatory drugs has been shown to be effective in the treatment of these diseases (Yamamoto, Y., et al., J. Clin Invest 107 135-142 (2001); Coward, W. R., et al., Clin Exp Allergy 28 Suppl 3, 42-46 (1998); Badger, A. M., et al., J. Pharmacol Exp Ther 290 587-593 (1999); Breton, J. J., et al., J Pharmacol Exp Ther 282 459-466 (1997); Roshak, A., et al., J Pharmacol Exp Ther 283 955-961 (1997); Kopp, E., et al., Science 265 956-959 (1994); Ichiyama, T., et al., Brain Res 911 56-61 (2001); Hehner, S. P., et al., J Immunol 163 5617-5623 (1999); Natarajan, K., et al., Proc Natl Acad Sci USA 93 9090-9095 (1996); and Fung-Leung, W. P., et al., Transplantation 60 362-368 (1995)). The common anti-inflammatory agent, aspirin, and aspirin-like drugs, the salicylates, are widely prescribed agents to treat inflammation and their effectiveness has been attributed to NF-κB inhibition. However, in order to treat chronic inflammations, the cellular levels of these salicylates need to be at very high concentration and are generally prescribed at 1-3 miliMolar plasma concentrations (*Science* 265, 956-959 (1994)).

Since the discovery of penicillin, over 100 antibacterial agents have been developed to combat a wide variety of bacterial infections. Today, the clinically used antibacterial agents mainly consists of β-lactams (penicillins, carbapenems and cephalosporins), aminoglycosides, tetracyclines, sulfonamides, macrolides (erythromycin), quinolones, and the drug of last resort: vancomycin (a glycopeptide). In recent years, many new strains of bacteria have developed resistance to these drugs throughout the world. There is a need for new antimicrobials.

Invasive infection with Gram positive or Gram negative bacteria often results in septic shock and death. Invasion of the blood stream by both types of bacteria (Gram positive and Gram negative) causes sepsis syndrome in humans as a result of an endotoxin, Lipopolysaccharide (LPS) (H. Bohrer, J. Clin. Invest. 972-985 (1997)), that triggers a massive inflammation response in the host. The mechanism by which LPS caused septic shock is through the activation of the transcription factor NF-κB. Activation of this protein by its kinase initiates the massive release of cytokines resulting in a potentially fatal septic shock. For example, the pneumococcus bacteria is the leading cause of death with a mortality rate of 40% in otherwise healthy elderly individuals and staphylococcal infections are the major cause of bacteremia in US hospitals today. Septic shock, caused by an exaggerated host response to these endotoxins often leads to multiple organ dysfunction, multiple organ failure, and remains the leading cause of death in trauma patients. Inhibition of NF-kB activation by LPS would, therefore, be therapeutically useful in the treatment of Septic shock and other bacterial infections.

There is considerable interest in modulating the efficacy of currently used antiproliferative agents to increase the rates and duration of antitumor effects associated with conventional antineoplastic agents. Conventional antiproliferative agents used in the treatment of cancer are broadly grouped as chemical compounds which (1) affect the integrity of nucleic acid polymers by binding, alkylating, inducing strand breaks, intercalating between base pairs or affecting enzymes which maintain the integrity and function of DNA and RNA; and (2) chemical agents that bind to proteins to inhibit enzymatic action (e.g. antimetabolites) or the function of structural proteins necessary for cellular integrity (e.g., antitubulin agents). Other chemical compounds that have been identified to be useful in the treatment of some cancers include drugs which block steroid hormone action for the treatment of breast and prostate cancer, photochemically activated agents, radiation sensitizers and protectors.

Of special interest to this invention are those compounds that directly affect the integrity of the genetic structure of the cancer cells. Nucleic acid polymers such as DNA and RNA are prime targets for anticancer drugs. Alkylating agents such as nitrogen mustards, nitrosoureas, aziridine (such as mitomycin C) containing compounds directly attack DNA. Metal coordination compounds such as cisplatin and carboplatin similarly directly attack the nucleic acid structure resulting in lesions that are difficult for the cells to repair, which, in turn, can result in cell death. Other nucleic acid affecting compounds include anthracycline molecules such as doxorubicin, which intercalates between the nucleic acid base pairs of DNA polymers, bleomycin which causes nucleic acid strand breaks, fraudulent nucleosides such as pyrimidine and purine nucleoside analogs which are inappropriately incorporated into nucleic polymer structures and ultimately cause premature DNA chain termination. Certain enzymes that affect the integrity and functionality of the genome can also be inhibited in cancer cells by specific chemical agents and result in cancer cell death. These include enzymes that affect ribonucleotide reductase (.e.g., hydroxyurea, gemcitabine), topoisomerase I (e.g., camptothecin) and topoisomerase II (e.g. etoposide).

The topoisomerase enzymes affect the structure of supercoiled DNA, because most of the functions of DNA require untwisting. Topoisomerase I (top 1) untwists supercoiled DNA, breaking only one of the two strands, whereas topoisomerase II (top 2) breaks both.

Topoisomerase I inhibition has become important in cancer chemotherapy through the finding that camptothecin (CPT), an alkaloid of plant origin, is the best known inhibitor of top 1 and is a very potent anticancer agent. CPT is contained in a Chinese tree, *Camptotheca acuminata.* A number of analogs have become approved for commercial use to treat a number of tumor types. These include CPT-11 (irinotecan) and topotecan.

While the clinical activity of camptothecins against a number of types of cancers are demonstratable, improvements in tumor response rates, duration of response and ultimately patient survival are still sought. The invention described herein demonstrates the novel use which can potentiate the antitumor effects of chemotherapeutic drugs, including topoisomerase I inhibitors, in particular, camptothecins.

Relevant Literature includes the following: Cancer Chemotherapeutic Agents, W. O. Foye, ed., (ACS, Washington, D.C.) (1995)); Cancer Chemotherapy Handbook, R. T. Dorr and D. D. VonHoff, (Appleton and Lange, Norwalk, Conn.) (1994); and M. P. Boland, Biochemical Society Transactions (2001) volume 29, part 6, p 674-678. DNA damage signaling and NF-κB: implications for survival and death in mammalian cells.

NF-κB has been indicated to inhibit apoptosis (programmed cell death). Many clinically used chemotherapeutic agents (including the vinca alkaloids, vincristine and vinblastinc, camptothecin and many others) have recently been shown to activate NF-κB resulting in a retardation of their cytotoxicity. This form of resistance is commonly referred to as NF-κB mediated chemoresistance. Inhibition of NF-κB has shown to increase the sensitivity to chemotherapeutic agents of tumor cells and solid tumors.

References: Cusack, J. C., Liu, F., Baldwin, A. S. *Drug Resist Updat*, 2, 271-273 (1999); Mayo, M. W., Baldwin, A. S. Science, 274, 784-787 (1996); Cusack, J. C., Jr., Liu, R., Baldwin, A. S., Jr. *Cancer Res,* 60, 2323-2330 (2000). Brandes, L. M., Lin, Z. P., Patierno, S. R., Kennedy, K. A. *Mol Pharmacol,* 60, 559-567 (2001); Arlt, A., Vorndamm, J., Breitenbroich, M., Folsch, U. R., Kalthoff, H. et al. *Oncogene,* 20, 859-868 (2001). Cusack, J. C., Jr., Liu, R., Houston, M., Abendroth, K., Elliott, P. J. et al. *Cancer Res* 61, 3535-3540 (2001).

The current invention describes the synthesis and application of imidazolines as clinically important compounds. The imidazolines were prepared via a new 1,2-dipolar cycloadditions reaction. 1,3 Dipolar cycloadditions reactions utilizing azlactones of "munchones" provide a general route for the synthesis of pyrroles and imidazoles (Hershenson, F. M. P., Synthesis 999-1001 (1988); Consonni, R. C., et al., J. chem. Research (S) 188-189 (1991); and Bilodeau, M. T. C., J. Org. Chem. 63 2800-2801 (1998)). This approach has not yet been reported for the imidazoline class of heterocycles. The synthetic and pharmacological interest in efficient syntheses of imidazolines has fueled the development of several diverse synthetic approaches (Puntener, K., et al., J. Org Chem 65 8301-8306 (2000); Hsiao, Y. H., J. Org. Chem. 62 3586-3591 (1997)). Recently, Arndtsen et al reported synthesis of symmetrically substituted imidazoline-4-carboxylic acids via a Pd-catalyzed coupling of an imine, acid chloride and carbon monoxide (Dghaym, R. D. D., et al., Angew. Chem. Int. Ed. Engl. 40 3228-3230 (2001)). In addition, diastereoselective 1,3-dipolar cycloaddition of azomethine ylides has been reported from amino acid esters with enantiopure sulfinimines to yield N-sulfinyl imidazolidines (Viso, A., et al., J. Org. Chem. 62 2316-2317 (1997)).

U.S. Pat. No. 6,318,978 to Ritzeler et al describes 3,4-benzimidazoles which are structurally quite different than those of the present invention. They inhibit NF-κB kinase. As can be seen, activity is retained where there are numerous different substituents in the imidazoline and benzene rings. M. Karin, Nature immunology, 3, 221-227 (2002); Baldwin, J. Clin. Invest., 3, 241-246 (2001); T. Huang et al, J. Biol. Chem., 275, 9501-9509 (2000); and J. Cusack and Baldwin, Cancer Research, 60, 2323-2330 (2000) describe the effect of activation of NF-κB on cancer. U.S. Pat. Nos. 5,804,374 and 6,410,516 to Baltimore describe NF-κB inhibition which are incorporated by reference.

Patents of interest for the general methodology of inhibition are set forth in U.S. Pat. No. 5,821,072 to Schwartz et al and U.S. Pat. No. 6,001,563 to Deely et al.

SUMMARY OF THE INVENTION

The present invention relates to a method for inhibiting inflammation in a mammal which comprises administering a multi-substituted 4-acid or 4-alkyl ester imidazoline to the mammal in an amount sufficient to inhibit the inflammation.

The present invention also relates to a method of inhibiting the activation of the NF-κB protein by inhibition of the degradation of the inhibitory protein, I kappa B, or its kinases and the ability to inhibit NF-κB which comprises of contacting the protein or its activating proteins with a multi-substituted 4-acid or 4-alkyl ester or amide imidazoline in an amount sufficient to inhibit activation of the protein.

The present invention also relates to a method for inhibiting autoimmune diseases, certain viral infections, including acquired immune deficiency syndrome (AIDS), adult respiratory distress syndrome, Ataxia Telangiestasia and a variety of skin related diseases, including psoriasis, atopic dermatitis and ultraviolet radiation induced skin damage.

The present invention further relates to inhibiting an immune response to a foreign NF-κB activator introduced into a mammal which makes the compounds useful for treatment of autoimmune diseases and useful for inhibiting rejection of tissue, skin, and organ transplants.

The present invention further relates to a method of inhibiting a cancer which comprises contacting the cancer with a multi-substituted imidazoline in an amount sufficient to inhibit the cancer.

The present invention relates to an imidazoline of the formula:

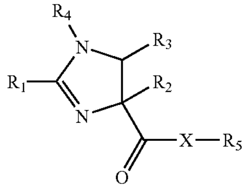

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; X is selected from the group consisting of O and S; and $R_5$ is selected from the group consisting of hydrogen, alkyl, acyl, aryl arylalkyl, heteroaryl, $NH_2$, NH—$R_6$ and

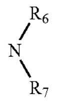

where $R_6$ and $R_7$ are selected from the group consisting of hydrogen, alkyl, aryl, arylalkyl, and heteroaryl and heterocyclic, which may be the same or different.

Further the present invention relates to an imidazoline of the formula

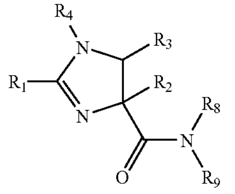

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; and wherein $R_8$ and $R_9$ and selected from the group consisting of hydrogen, alkyl, aryl, arylalkyl, heteroaryl and heterocyclic, which may be the same or different.

Further, the present invention relates to a process for the preparation of an amino imidazoline which comprises reacting an imidazoline of the formula:

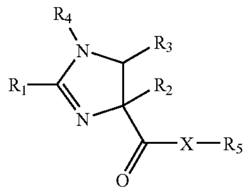

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; X is selected from the group consisting of O and S; and $R_5$ is selected from the group consisting of hydrogen, alkyl, acyl, aryl arylalkyl, heteroaryl, $NH_2$, NH—$R_6$ and

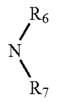

where $R_6$ and $R_7$ and selected from the group consisting of hydrogen, alkyl, aryl, arylalkyl, and heteroaryl and heterocyclic, which may be the same or different, with an amine of the formula:

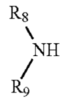

to produce a compound of the formula:

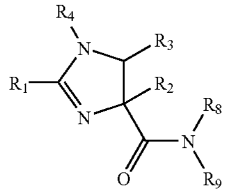

wherein $R_8$ and $R_9$ are selected from the group consisting of hydrogen, alkyl, acyl, arylalkyl and heteroalkyl, which may be the same or different.

The present invention relates to an imidazoline of the formula

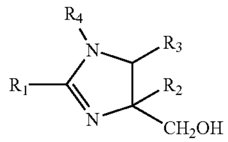

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; and $R_5$ is selected from the group consisting of hydrogen and an alkyl group, all of which are optionally substituted.

The present invention particularly relates to an imidazoline of the formula:

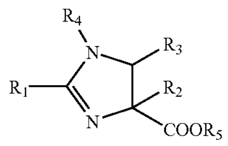

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and $R_5$ is selected from the group consisting of hydrogen and an alkyl group, all of which are optionally substituted. Preferably $R_1$ is phenyl; $R_4$ is benzyl; $R_5$ is lower alkyl containing 1 to 4 carbon atoms. Also preferably $R_5$ is ethyl; $R_2$ is lower alkyl containing 1 to 4 carbon atoms. Most preferably $R_2$ is methyl and $R_3$ is selected from the group consisting of phenyl and substituted phenyl.

The imidazoline (Compound 1) wherein $R_1$ is phenyl, $R_2$ is methyl, $R_3$ is phenyl, $R_4$ is benzyl and $R_5$ is H is a preferred compound. The imidazoline (Compound 2) wherein $R_1$ is phenyl, $R_2$ is methyl, $R_3$ is 4-methoxyphenyl, $R_4$ is benzyl and $R_5$ is H is a preferred compound. The imidazoline (Compound 3) wherein $R_1$ is phenyl, $R_2$ is methyl, $R_3$ is phenyl, $R_4$ is 4-fluorophenyl and $R_5$ is H is a preferred compound. The imidazoline (compound 4) wherein $R_1$ is phenyl, $R_2$ is phenyl, $R_3$ is phenyl, $R_4$ is benzyl and $R_5$ is H is a preferred compound. The imidazoline (Compound 5) wherein $R_1$ is phenyl, $R_2$ is 1H-indol-3-ylmethyl, $R_3$ is phenyl, $R_4$ is benzyl and $R_5$ is H is a preferred compound. The imidazoline (Compound 6) wherein $R_1$ is phenyl, $R_2$ is methyl, $R_3$ is pyridin-4-yl, $R_4$ is benzyl and $R_5$ is H is a preferred compound. The imidazoline (Compound 7) wherein $R_1$ is phenyl, $R_2$ is methyl, $R_3$ is phenyl, $R_4$ is H and $R_5$ is H is a preferred compound. The imidazoline (Compound 8) wherein $R_1$ is phenyl, $R_2$ is methyl, $R_3$ is ethoxycarbonyl, $R_4$ is H and $R_5$ is H is a preferred compound. The imidazoline (Compound 9) wherein $R_1$ is phenyl, $R_2$ is methyl, $R_3$ is pyridin-4-yl, $R_4$ is benzyl and $R_5$ is Et is a preferred compound. The imidazoline (Compound 10) wherein $R_1$ is phenyl, $R_2$ is methyl, $R_3$ is phenyl, $R_4$ is benzyl and $R_5$ is Et is a preferred compound.

The present invention also relates to a process for the preparation of imidazoline of the formula:

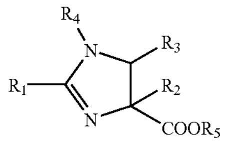

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; and $R_5$ is selected from the group consisting of hydrogen and an alkyl group, all of which are optionally substituted, which comprises:

(a) reacting a reaction mixture of (1) an oxazolone of the formula:

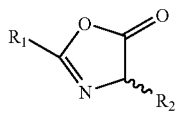

(2) a ketone of the formula:

$R_3{=}O$

; and (3) an amine of the formula:

$H_2N{-}R_4$ in the presence of trimethyl silyl chloride or an acid chloride and a solvent for the reactants in the absence of water in the presence of a non-reactive gas and at a temperature between about 0 and 100° C. to produce the imidazoline; and (b) separating the imidazoline from the reaction mixture. The imidazoline can be esterified by reaction with an alcohol. The imidazoline is most preferably esterified by reaction with the alcohol and sulfonyl dichloride.

The present invention relates to a method for inhibiting inflammation in a mammal which comprises administering an imidazoline of the formula:

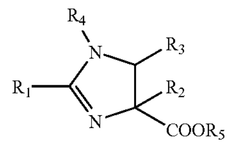

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted, to the mammal in an amount sufficient to inhibit the inflammation. Preferably the mammal is human. The mammal can be a lower mammal. The administration can be oral, topical, or by injection (such as intravenous) into the mammal.

The present invention also relates to a method for inhibiting a microorganism which comprises:

administering an effective amount of a compound of the formula:

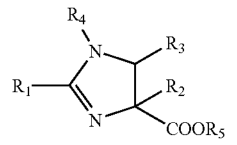

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted, to inhibit the microorganism. The inhibition can be in vitro or in vivo. The administration can be to a lower mammal or to a human. The administration can be oral, by injection into the mammal, or topical.

Further, the present invention relates to a method of inhibiting degradation of a protein which is NF-κB or NF-κB kinase which comprises contacting the protein with a compound of the formula:

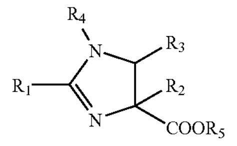

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted. The compounds are also useful in the treatment of tumors (cancers) where NFkB is involved. The inhibition is preferably in vivo.

The present invention further relates to a method for inhibiting an immune response to a foreign NF-κB activator introduced into a mammal which comprises administering an effective amount of an imidazoline of the formula:

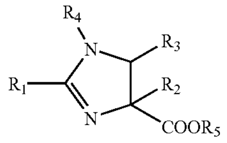

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and, $R_5$ is selected from the group consisting of hydrogen and an alkyl group, all of which are optionally substituted, to the mammal so as to thereby inhibit the immune response to the foreign NF-κB activator.

The present invention further relates to a method for treating an autoimmune disease in a mammal without bringing on complete immunodeficiency in the mammal which comprises administering an effective amount of an imidazoline of the formula:

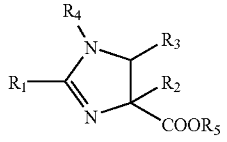

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and, $R_5$ is selected from the group consisting of hydrogen and an alkyl group, all of which are optionally substituted, to the mammal so as to treat the autoimmune disease.

The present invention further relates to a method for inhibiting rejection of an organ transplanted into a mammal which comprises administering an effective amount of an imidazoline of the formula:

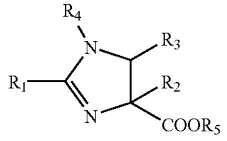

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and, $R_5$ is selected from the group consisting of hydrogen and an alkyl group, all of which are optionally substituted, to the mammal so as to inhibit rejection of the organ transplanted into the mammal.

The present invention further relates to a method for inhibiting reactivation of human immunodeficiency virus (HIV) in cells latently infected with the HIV which comprises administering an effective amount of an imidazoline of the formula:

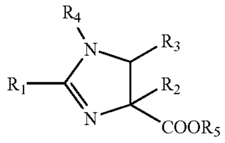

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and, $R_5$ is selected from the group consisting of hydrogen and an alkyl group, all of which are optionally substituted, to inhibit the reactivation of the HIV in the latently infected cells.

In further embodiments of the above methods, $R_1$ is phenyl, $R_4$ is benzyl, $R_5$ is lower alkyl containing 1 to 4 carbon atoms, $R_5$ is ethyl, $R_2$ is lower alkyl containing 1 to 4 carbon atoms, $R_2$ is methyl and $R_3$ is selected from the group consisting of phenyl and substituted phenyl, or combinations of the above.

$R_1$ is (1) phenyl, mono- or disubstituted independently of one another by (1) (1)—CN;

(1) (2)—$NO_2$;

(1) (3)—O—($C_1$-$C_4$)-alkyl;

(1) (4)—$NH_2$; or (1) (5)—($C_1$-$C_4$)-alkyl-$NH_2$;

(1) (6)—x, wherein x is a halogen.

(2) heteroaryl having 5 to 14 ring members, in which the heteroaryl is unsubstituted or mono-, di-, or trisubstituted independently of one another by —N—$R^{14}$, in which $R^{14}$ is —($C_1$-$C_6$)-alkyl, —($C_3$-$C_6$)-cycloalkyl, phenyl, halogen, —OH, or —($C_1$-$C_4$)-alkyl; or (3) a heterocycle having 5 to 12 ring members, in which the heterocycle is unsubstituted or mono-, di-, or trisubstituted independently of one another by —N—$R^{14}$, in which $R^{14}$ is —($C_1$-$C_6$)-alkyl, —($C_3$-$C_6$)-cycloalkyl, phenyl, halogen, —OH, or —($C_1$-$C_4$)-alkyl.

The term "halogen" is understood as meaning fluorine, chlorine, bromine, or iodine. The term "aryl" is understood as meaning aromatic hydrocarbon groups having 6 to 14 carbon atoms in the ring. ($C_6$-$C_{14}$)-Aryl groups are, for example, phenyl, naphthyl, for example, 1-naphthyl, 2-naphthyl, biphenylyl, for example, 2-biphenylyl, 3-biphenylyl, and 4-biphenylyl, anthryl, or fluorenyl. Biphenylyl groups, naphthyl groups, and, in particular, phenyl groups are preferred aryl groups. Aryl groups, in particular phenyl groups, can be mono-substituted or polysubstituted, preferably monosubstituted, disubstituted, or trisubstituted, by identical or different groups, preferably by groups selected from ($C_1$-$C_8$)-alkyl, in particular ($C_1$-$C_4$)-alkyl, ($C_1$-$C_8$)-alkoxy, in particular ($C_1$-$C_4$)-alkoxy, halogen, nitro, amino, trifluoromethyl, hydroxyl, hydroxy-($C_1$-$C_4$)-alkyl such as hydroxymethyl, 1-hydroxyethyl, or 2-hydroxyethyl, methylenedioxy, ethylenedioxy, formyl, acetyl, cyano, hydroxycarbonyl, aminocarbonyl, ($C_1$-$C_4$)-alkoxycarbonyl, phenyl, phenoxy, benzyl, benzyloxy, or tetrazolyl. Further, when aryl is phenyl, phenyl is optionally mono- or disubstituted independently of one another by —CN, —$NO_2$, —O—($C_1$-$C_4$)-alkyl, —N($R^{11}$)$_2$, —NH—C(O)—$R^{11}$, —S(O)$_x$$R^1$, in which x is the integer 0, 1, or 2, —C(O)—$R^{11}$, in which $R^{11}$ is as defined above, or —($C_1$-$C_4$)-alkyl-$NH_2$. The same applies, for example, to groups such as arylalkyl or arylcarbonyl. Arylalkyl groups are, in particular, benzyl and also 1- and 2-naphthylmethyl, 2-, 3-, and 4-biphenylylmethyl, and 9-fluorenylmethyl. Substituted arylalkyl groups are, for example, benzyl groups and naphthylmethyl groups substituted in the aryl moiety by one or more ($C_1$-$C_8$)-alkyl groups, in particular ($C_1$-$C_4$)-alkyl groups, for example, 2-, 3-, and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7-, and 8-methyl-1-naphthylmethyl, 1-, 3-, 4-, 5-, 6-, 7-, and 8-methyl-2-naphthylmethyl, by one or more ($C_1$-$C_8$)-alkoxy groups, in particular ($C_1$-$C_4$)-alkoxy groups, benzyl groups, and naphthylmethyl groups substituted in the aryl moiety for example, 4-methoxybenzyl, 4-neopentyloxybenzyl, 3,5-dimethoxybenzyl, 3,4-methylenedioxybenzyl, 2,3,4-trimethoxybenzyl, nitrobenzyl groups, for example, 2-, 3-, and 4-nitrobenzyl, halobenzyl groups, for example, 2-, 3-, and 4-chloro- and 2-, 3-, and 4-fluorobenzyl, 3,4-dichlorobenzyl, pentafluorobenzyl, trifluoromethylbenzyl groups, for example, 3- and 4-trifluoromethylbenzyl, or 3,5-bis(trifluoromethyl)benzyl.

In monosubstituted phenyl groups, the substituent can be located in the 2-position, the 3-position, or the 4-position. Disubstituted phenyl can be substituted in the 2,3-position, the 2,4-position, the 2,5-position, the 2,6-position, the 3,4-position, or the 3,5-position. In trisubstituted phenyl groups, the substituents can be located in the 2,3,4-position, the 2,3,5-position, the 2,4,5-position, the 2,4,6-position, the 2,3,6-position, or the 3,4,5-position.

The explanations for the aryl groups apply accordingly to divalent arylene groups, for example, to phenylene groups that can be present, for example, as 1,4-phenylene or as 1,3-phenylene.

Phenylene-($C_1$-$C_6$)-alkyl is in particular phenylenemethyl (—$C_6H_4$—$CH_2$—) and phenyleneethyl. ($C_1$-$C_6$). Alkylenephenyl is in particular methylenephenyl (—$CH_2$-$C_6H_4$—). Phenylene-($C_1$-$C_6$)-alkenyl is in particular phenyleneethenyl and phenylenepropenyl.

The expression "heteroaryl having 5 to 14 ring members" represents a group of a monocyclic or polycyclic aromatic system having 5 to 14 ring members, which contains 1, 2, 3, 4, or 5 heteroatoms as ring members. Examples of heteroatoms are N, O, and S. If a number of heteroatoms are contained, these can be identical or different. Heteroaryl groups can likewise be monosubstituted or polysubstituted, preferably monosubstituted, disubstituted, or trisubstituted, by identical or different groups selected from ($C_1$-$C_8$)-alkyl, in particular ($C_1$-$C_4$)-alkyl, ($C_1$-$C_8$)-alkoxy, in particular ($C_1$-$C_4$)-alkoxy, halogen, nitro, —N($R^{11}$)$_2$, trifluoromethyl, hydroxyl, hydroxy-($C_1$-$C_4$)-alkyl such as hydroxymethyl, 1-hydroxyethyl, or 2-hydroxyethyl, methylenedioxy, formyl, acetyl, cyano, hydroxycarbonyl, aminocarbonyl, ($C_1$-$C_4$)-alkoxycarbonyl, phenyl, phenoxy, benzyl, benzyloxy, or tetrazolyl. Heteroaryl having 5 to 14 ring members preferably represents a monocyclic or bicyclic aromatic group which contains 1, 2, 3, or 4, in particular 1, 2, or 3, identical or different heteroatoms selected from N, O, and S, and which can be substituted by 1, 2, 3, or 4, in particular 1, 2, or 3, identical or different substituents selected from ($C_1$-$C_6$)-alkyl, ($C_1$-$C_6$)-alkoxy, fluorine, chlorine, nitro, —N($R^{11}$)$_2$, trifluoromethyl, hydroxyl, hydroxy ($C_1$-$C_4$)-alkyl, ($C_1$-$C_4$)-alkoxycarbonyl, phenyl, phenoxy, benzyloxy, and benzyl. Heteroaryl particularly preferably represents a monocyclic or bicyclic aromatic group having 5 to 10 ring members, in particular a 5-membered or 6-membered monocyclic aromatic group which contains 1, 2, or 3, in particular 1 or 2, identical or different heteroatoms selected from N, O, and S, and can be substituted by 1 or 2 identical or different substituents selected from ($C_1$-$C_4$)-alkyl, halogen, hydroxyl, —N($R^{11}$)$_2$, ($C_1$-$C_4$)-alkoxy, phenyl, phenoxy, benzyloxy, and benzyl. $R^{11}$ is as defined in substituent $R^9$ of formula I.

The expression "heterocycle having 5 to 12 ring members" represents a monocyclic or bicyclic 5-membered to 12-membered heterocyclic ring that is partly saturated or completely saturated. Examples of heteroatoms are N, O, and S. The heterocycle is unsubstituted or substituted on one or more carbons or on one or more heteroatoms by identical or different substituents. These substituents have been defined above for the radical heteroaryl. In particular, the heterocyclic ring is monosubstituted or polysubstituted, for example, monosubstituted, disubstituted, trisubstituted, or tetrasubstituted, on carbons by identical or different groups selected from ($C_1$-$C_8$)-alkyl, for example, ($C_1$-$C_4$)-alkyl, ($C_1$-$C_8$)-alkoxy, for example, ($C_1$-$C_4$)-alkoxy such as methoxy, phenyl-($C_1$-$C_4$)-alkoxy, for example, benzyloxy, hydroxyl, oxo, halogen, nitro, amino, or trifluoromethyl, and/or it is substituted on the ring nitrogens in the heterocyclic ring by ($C_1$-$C_8$)-alkyl, for example, ($C_1$-$C_4$)-alkyl such as methyl or ethyl, by optionally substituted phenyl or phenyl-($C_1$-$C_4$)-alkyl, for example, benzyl. Nitrogen heterocycles can also be present as N-oxides or as quaternary salts.

Examples of the expressions heteroaryl having 5 to 14 ring members or heterocycle having 5 to 12 ring members are groups which are derived from pyrrole, furan, thiophene, imidazole, pyrazole, oxazole, isoxazole, thiazole, isothiazole, tetrazole, 1,3,4-oxadiazole, 1,2,3,5-oxathiadiazole-2-oxides, triazolones, oxadiazolones, isoxazolones, oxadiazolidinediones, triazoles which are substituted by F, CN, $CF_3$, or COO—($C_1$-$C_4$)-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these hterocycles. Particularly preferred groups are 2- or 3-pyrrolyl, phenylpyrrolyl such as 4- or 5-phenyl-2-pyrrolyl, 2-furyl, 2-thienyl, 4-imidazolyl, methylimidazolyl, for example, 1-methyl-2,4-, or 5-imidazolyl, 1,3-thiazol-2-yl, 2-pyridyl, 3-pyridyl, 4-pyridyl, 2-, 3-, or 4-pyridyl-N-oxide, 2-pyrazinyl, 2-, 4-, or 5-pyrimidinyl, 2-, 3-, or 5-indolyl, substituted 2-indolyl, for example, 1-methyl-, 5-methyl-, 5-methoxy-, 5-benzyloxy-, 5-chloro-, or 4,5-dimethyl-2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, or benzothiazolyl, or dihydropyridinyl, pyrrolidinyl, for example, 2- or 3-(N-methylpyrrolidinyl), piperazinyl, morpholinyl, thiomorpholinyl, tetrahydrothienyl, or benzodioxolanyl.

Thus methods and compositions are provided for the treatment of a host with a cellular proliferative disease, particularly a neoplasia. In the subject methods, pharmaceutically acceptable imidazolines and an antiproliferative agent are administered, preferably systemically.

Methods and compositions are provided for the treatment of a host with a cellular proliferative disease, particularly a neoplasia. In the subject methods, a pharmaceutically acceptable imidazoline is administered, preferably systemically, in conjunction with an antiproliferative agent to improve the anticancer effects. In a preferred embodiment, the imidazoline provides a chemopotentiator effect.

A chemical agent is a chemopotentiator when it enhances the effect of a known antiproliferative drug in a more than additive fashion relative to the activity of the chemopotentiator or antiproliferative agent used alone. In some cases, a chemosensitizing effect may be observed. This is defined as the effect of use of an agent that if used alone would not demonstrate significant antitumor effects but would improve the antitumor effects of an antiproliferative agent in a more than additive fashion than the use of the antiproliferative agent by itself.

As used herein, the term imidazoline includes all members of that chemical family including the forms and analogs thereof. The imidazoline family is defined by chemical structure as the ring structures previously described.

As used herein, antiproliferative agents are compounds, which induce cytostasis or cytotoxicity. Cytostasis is the inhibition of cells from growing while cytotoxicity is defined as the killing of cells. Specific examples of antiproliferative agents include: antimetabolites, such as methotrexate, 5-fluorouracil, gemcitabine, cytarabine; anti-tubulin protein agents such as the vinca alkaloids, paclitaxel, colchicine; hormone antagonists, such as tamoxifen, LHRH analogs; and nucleic acid damaging agents such as the alkylating agents melphalan, BCNU, CCNU, thiotepa, intercalating agents such as doxorubicin and metal coordination complexes such as cisplatin and carboplatin.

Thus methods and compositions are provided for the treatment of a host with a cellular proliferative disease, particularly a neoplasia. In the subject methods, pharmaceutically acceptable imidazolines and an antiproliferative agent are administered, preferably systemically.

Methods and compositions are further provided for the treatment of a host with an autoimmune disease or an organ transplant or skin graft. In the subject methods, a pharmaceutically acceptable imidazoline is administered, preferably systemically, optionally in conjunction with one or more anti-autoimmune or anti-rejection agents to improve the inhibition of the immune response involved in the autoimmune disease or transplant or graft.

OBJECTS

It is an object of the present invention to provide novel compounds which inhibit immune responses to foreign NF-κB activators introduced into a mammal.

It is also an object of the present invention to provide novel compounds which inhibit immune responses involved in rejection of organs transplanted into a mammal.

It is further an object of the present invention to provide novel compounds which inhibit the immune response involved in autoimmune diseases in a mammal which involve NF-κB activation.

It is a further still object of the present invention to inhibit HIV by inhibiting NF-κB translocation to the cell nucleus of cells infected with HIV.

It is a further still object of the present invention to inhibit immune responses to foreign NFκB activators such as those involved in organ transplants or immune responses which are involved in autoimmune diseases without bringing on complete immunodeficiency in the mammal.

It is a further still object of the present invention to provide novel compounds which are anti-inflammatory, antimicrobial and inhibit NFκB or NFκB kinase.

It is a further still object of the present invention to provide for inhibition of cancers by inhibition of chemoresistance.

It is a further still object of the present invention to provide a novel process for the preparation of such compounds.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides a method for inhibiting pathological activation of the transcription factor NF-kappaB (NF-κB) by imidazolines. These agents were synthesized and found to be potent non-toxic inhibitors of NF-κB. Such compounds may be used in the treatment of diseases, in which activation of the NF-κB signaling pathway is involved. Inhibition of NF-κB activation inhibits the transcription of genes related to a variety of inflammatory diseases such as: rheumatoid arthritis, inflammatory bowel disease, astma, chronic obstructive pulmonary disease (COPD) osteoarthritis, osteoporosis and fibrotic diseases. Inhibition of NF-κB is useful in the treatment of autoimmune diseases including systemic lupus eythematosus, multiple sclerosis, psoriatic arthritis, alkylosing spondylitis, and tissue and organ rejection. In addition, inhibition of NF-κB is useful in the treatment of Alzheimer's disease, stroke atherosclerosis, restenosis, diabetes, glomerulophritis, cancer, Hodgkins disease, cachexia, inflammation associated with infection and certain viral infections, including acquired immune deficiency syndrome (AIDS), adult respiratory distress syndrome, Ataxia Telangiestastia and a variety of skin related diseases, including psoriasis, atopic dermatitis and ultraviolet radiation induced skin damage. In particular embodiments, the imidazolines herein have the ability to inhibit an immune response to a foreign NF-κB activator introduced into a mammal which makes the compounds useful for treatment of autoimmune diseases and useful for inhibiting rejection of tissue, skin, and organ transplants.

Figure 1:
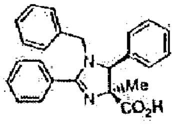
FIG. 1 shows the structures of compounds 1 to 20.
Figure 1:
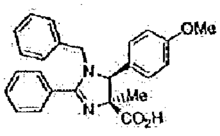
Figure 1:
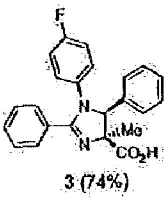
Figure 1:
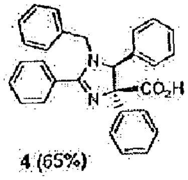
Figure 1:
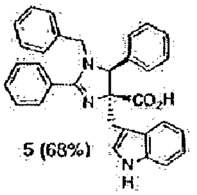
Figure 1:
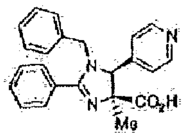
Figure 1:
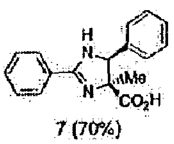
Figure 1:
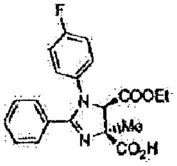
Figure 1:
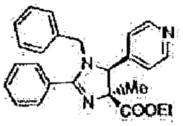
Figure 1:
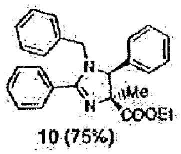
Figure 1:
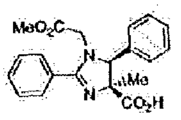
Figure 1:
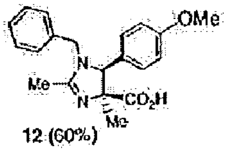
Figure 1:
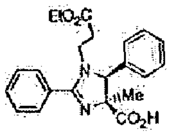
Figure 1:
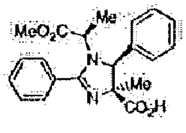
Figure 1:
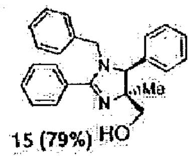
Figure 1:
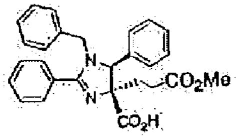
Figure 1:
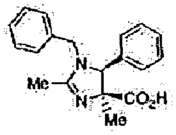
Figure 1:
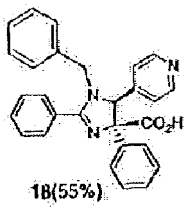
Figure 1:
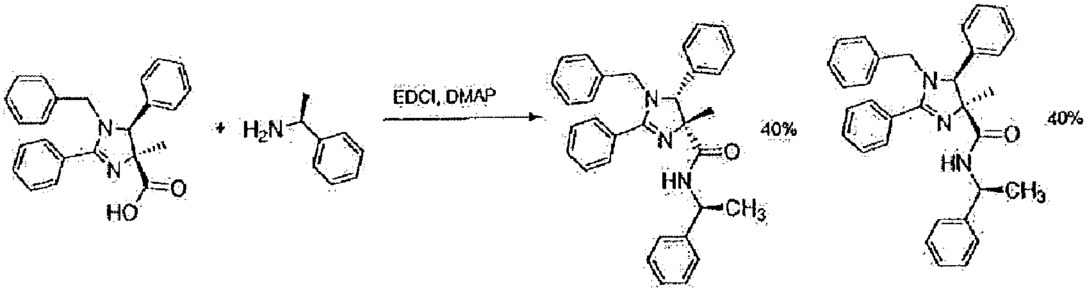
Figure 2:
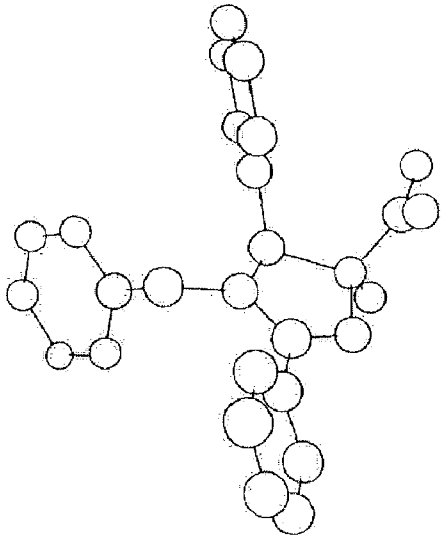
FIG. 2 shows the x-ray crystal structure of compound 1 which is representative.
Figure 6:
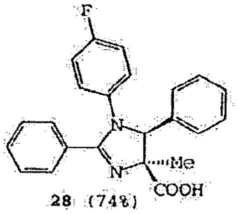
FIG. 6 shows the structure of novel imidazolines 28-50. 37 and 38 are after esterification with $(COCl)_2$, EtOH. 39 is after hydrogenation with $H_2$, 5% Pd/C.
Figure 6:
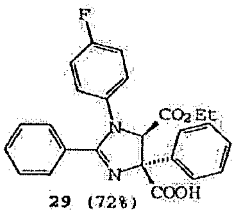
Figure 6:
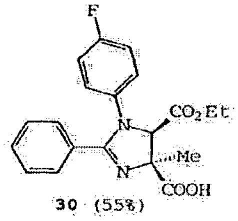
Figure 6:
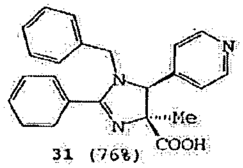
Figure 6:
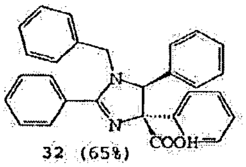
Figure 6:
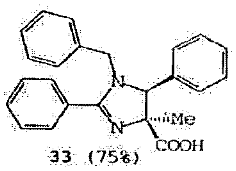
Figure 6:
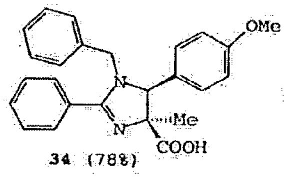
Figure 6:
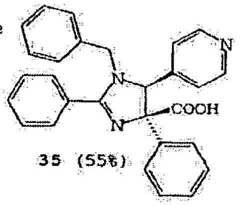
Figure 6:
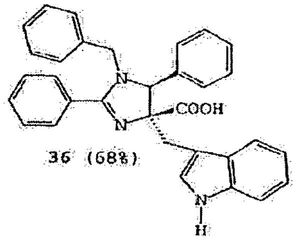
Figure 6:
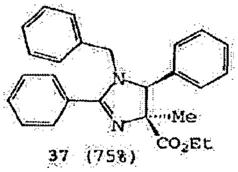
Figure 6:
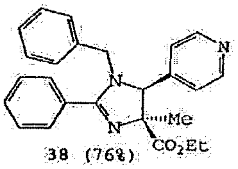
Figure 6:
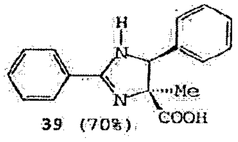
Figure 6:
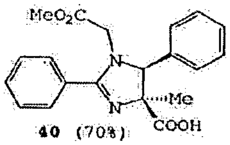
Figure 6:
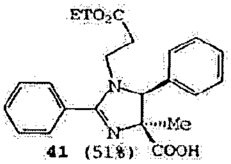
Figure 6:
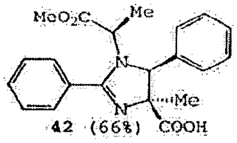
Figure 6:
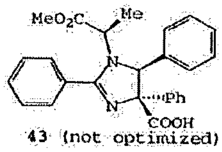
Figure 6:
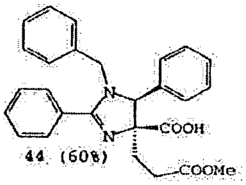
Figure 6:
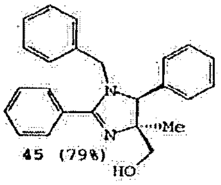
Figure 6:
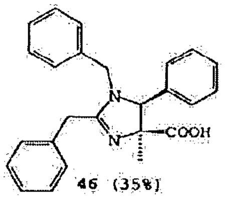
Figure 6:
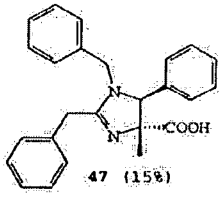
Figure 6:
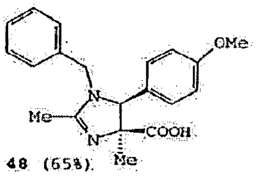
Figure 6:
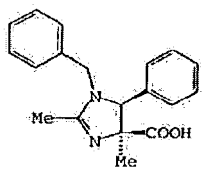
Figure 6:
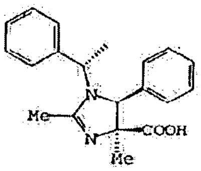

Preferred compounds are shown in FIGS. 1 and 6. The stereopositioning is shown in FIG. 2. The combination of these two key characteristics makes this class of imidazolines an extremely effective therapeutic drug to treat inflammatory diseases, cancers, autoimmune diseases and to inhibit rejection of transplanted organs, tissues, and grafted skin. The objective of this invention is the use of multisubstituted imidazolines for therapeutic use as (1) anti-inflammatory agents (for example in the treatment of asthma and rheumatoid arthritis), (2) antibacterial agents, including antiseptic agents, (3) anticancer agents and potentiators of anticancer drugs such as cisplatin and the like, (4) anti-autoimmune agents (for example, for the treatment of autoimmune diseases such as systemic lupus eythematous, multiple sclerosis, psoriatic arthritis, alkylosing spondylitis) and (5) anti-rejection agents for use in organ transplant and skin graft procedures with or without other anti-rejection compounds to inhibit rejection of the transplanted organ or grafted skin.

The compounds of the present invention are very potent inhibitors of NF-κB in vitro (less than 0.1 μM concentrations) and preliminary experiments in cells have indicated that the compounds are not cytotoxic over a 72 hour time period. Several of the imidazolines indicated antimicrobial activity against several strains of bacteria with MIC's of 50 μg/mL.

The present invention also relates to the synthesis of the first class of imidazoline-type NF-κB inhibitors. The imidazolines were prepared via a novel highly diastereoselective multicomponent synthesis using amino acid derived oxazolidinones as general templates.

The general procedure for synthesis of imidazoline-4-carboxylic acids is as follows. A solution of aldehyde (for example 0.57 mmol), amine (for example 0.57 mmol) in dry $CH_2Cl_2$ (10 mL) was refluxed under $N_2$ for 2 hours. A solution of the oxazolone (for example 0.57 mmol) in dry $CH_2Cl_2$ (for example 5 mL) was added and the mixture was refluxed under $N_2$ for 6 hours, and then stirred overnight at room temperature. The product was preferably either precipitated out from 1:1 $CH_2Cl_2$ or isolated after silica gel chromatography with 4:1 EtOAc/MeOH.

This is a novel highly diastereoselective multicomponent one-pot synthesis of aryl, acyl, alkyl and heterocyclic unsymmetrical substituted imidazolines. After screening a small number of Lewis acids it was found that TMSCl (trimethylsilylchloride) promotes the condensation of azlactones and imines to afford imidazolines in good yields as single diastereometers (Scheme 1).

Scheme 1 -
Multicomponent one-pot synthesis of imidazolines

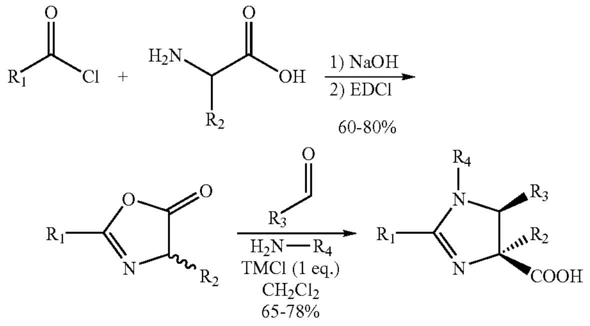

Acyl chlorides (RCOCl) where R is chiral can be used to obtain a single enantiomer. The azlactones were prepared from different N-acyl-α-amino acids followed by EDCl (1-(3-dimethylaminopropyl)-3-ethylcarbodiimide hydrochloride) mediated dehydration to provide the pure azlactones in high yields (Schunk et al., Organic letters 2: 907-910 (2000); Sain et al., Heterocycles 23: 1611-1614 (1985)). The cycloaddition reactions with the imines proceeded well at slightly elevated temperatures (for example 40° C.) to provide the high substituted imidazolines in good yields. The absence of trimethylsilyl chloride resulted in the formation of β-lactams, presumably via a ketene intermediate (Peddibhotla et al., Highly Diastereoselective Multicomponent Synthesis of Unsymmetrical Imidazolines, Organic Letters 4: 3533-3535 (2002)). Only the trans diastereomers of the imidazolines were observed in most of these reactions as determined by NOE experiments and X-ray crystallography. The diastereoselective multicomponent one-pot synthesis provided a wide range of aryl, acyl, alkyl and heterocyclic substituted imidazolines in excellent yields (Table 1).

TABLE 1

Preparation of imidazolines 1-10

| compound | $R_1$ | $R_2$ | $R_3$ | $R_4$ | $R_5$ | Yield (%) |
|---|---|---|---|---|---|---|
| 1 | Phenyl | Methyl | Phenyl | Benzyl | H | 75 |
| 2 | Phenyl | Methyl | 4-methoxy-phenyl | Benzyl | H | 78 |
| 3 | Phenyl | Methyl | Phenyl | 4-Fluorophenyl | H | 74 |
| 4 | Phenyl | Phenyl | Phenyl | Benzyl | H | 65 |
| 5 | Phenyl | 1H-indol-3-yl-methyl | Phenyl | Benzyl | H | 68 |
| 6 | Phenyl | methyl | pyridin-4-yl | Benzyl | H | 76 |
| 7[a] | Phenyl | Methyl | Phenyl | H | H | 70 |

TABLE 1-continued

Preparation of imidazolines 1-10

| compound | $R_1$ | $R_2$ | $R_3$ | $R_4$ | $R_5$ | Yield (%) |
|---|---|---|---|---|---|---|
| 8 | Phenyl | Methyl | Ethoxy-carbonyl | H | H | 72 |
| 9[b] | Phenyl | Methyl | pyridin-4-yl | Benzyl | Et | 76 |
| 10[c] | Phenyl | Methyl | Phenyl | Benzyl | Et | 75 |

[a]After hydrogenation (10% Pd/C, $H_2$ 1 atm) of compound 1.
[b]After esterification (SOCl2, EtOH) of compound 6.
[c]After esterification (SOCl2, EtOH) of compound 1.

While the complete mechanistic detail of this process is still under investigation, the reaction does not seem to proceed by activation of the carbonyl oxygen of the oxazolone by trimethylsilyl chloride, in turn causing ring-opening to the intermediate nitrilium ion as initially expected (Ivanova, G. G., Tetrahedron 48 177-186 (1992)). Carrying out the condensation in presence of slight excess of triethylamine halted the reaction altogether suggesting that acidic conditions were required. In addition, the addition of Lewis acids such as $TiCl_4$ or $BF_3$. $OEt_2$ did not result in any product formation. In the light of these findings, it is proposed that the reaction probably proceeds by 1,3-dipolar type of cycloaddition. Steric repulsion between the $R_2$ and $R_3$ moieties during the cycloaddition can explain the diastereoselectivity (Scheme 2).

Scheme 2.
Proposed mechanism for imidazoline formation.

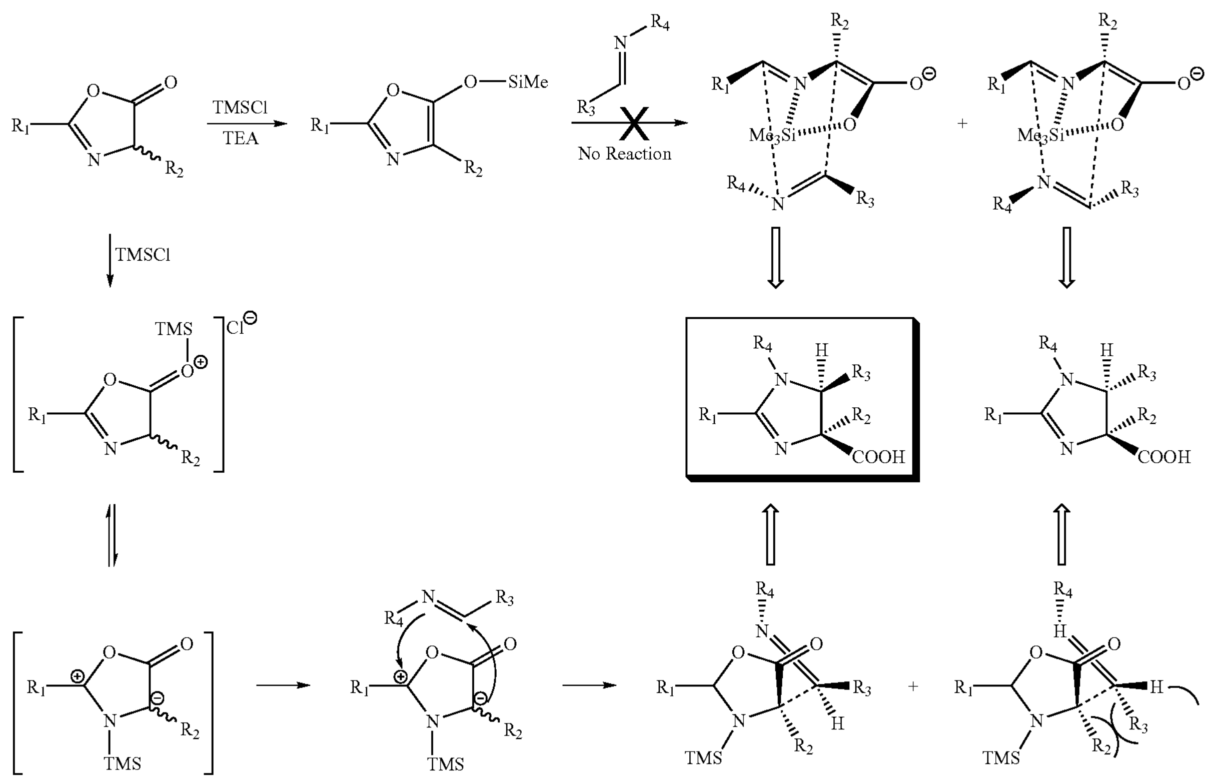

In pharmaceutical compositions, the imidazoline is inhibitory at a dosage of 1 to 1,000 micrograms per milliliter or gram. It can be used in a ratio of 1 to 100 or 100 to 1 with other compounds or drugs for the treatment of autoimmune diseases or anti-rejection compounds or drugs. In a preferred embodiment, one or more of the imidazolines for treating a patient are provided to the patient at an inhibitory dose in a pharmaceutically acceptable carrier. As such, the imidazolines are processed with pharmaceutical carrier substances by methods well known in the art such as by means of conventional mixing, granulating, coating, suspending and encapsulating methods, into the customary preparations for oral or rectal administration. Thus, imidazoline preparations for oral application can be obtained by combining one or more of the imidizolines with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropylmethylcellulose phthalate, with or without suitable softeners such as phthalic acid ester or triacetin. Dyestuffs or pigments may be added to the tablets or dragee coatings, for example for identification or marking of the various doses of active ingredient.

Imidazoline preparations comprising one or more of the imidizolines which can be administered orally further include hard gelatine capsules, as well as hard or soft closed capsules made from gelatine and, if required, a softener such as glycerin or sorbitol. The hard gelatine capsules can contain one or more of the imidazolines in the form of a granulate, for example in admixture with fillers such as maize starch, optionally granulated wheat starch, binders or lubricants such as talcum, magnesium stearate or colloidal silicic acid, and optionally stabilizers. In closed capsules, the one or more of the imidazolines is in the form of a powder or granulate; or it is preferably present in the form of a suspension in suitable solvent, whereby for stabilizing the suspensions there can be added, for example, glycerin monostearate.

Other imidazoline preparations to be administered orally are, for example, aqueous suspensions prepared in the usual manner, which suspensions contain the one or more of the imidizolines in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable imidazoline preparations for rectal administration are, for example, suppositories consisting of a mixture of one or more of the imidazolines with a suppository foundation substance. Such substances are, in particular, natural or synthetic triglyceride mixtures. Also suitable are gelatine rectal capsules consisting of a suspension of the one or more of the imidazolines in a foundation substance. Suitable foundation substances are, for example, liquid triglycerides, of higher or, in particular, medium saturated fatty acids.

Likewise of particular interest are preparations containing the finely ground one or more of the imidazolines, preferably that having a median of particle size of 5 μm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the imidazolines are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the imidazoline/starch mixture with a surface-active substance or with other auxiliaries, these substances may also be added to the water used to prepare the suspension. The concentrates for producing suspensions, consisting of the one or more of the imidazoline/starch mixtures and optionally auxiliaries, can be packed in single-dose amounts, if required in an airtight and moisture-proof manner.

In addition, the one or more imidazolines can be administered to a patient intraperitoneally, intranasally, subcutaneously, or intravenously. In general, for intraperitoneal, intranasal, subcutaneous, or intravenous administration, one or more of the imidazolines are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more imidazolines are provided in a composition acceptable for intraperitoneal, subcutaneous, or intravenous use in warm-blooded animals or humans. For example, such compositions can comprise a physiologically acceptable solution such as a buffered phosphate salt solution as a carrier for the one or more anthraquinones. Preferably, the solution is at a physiological pH. In particular embodiments, the composition is injected directly into the patient perfused through the tumor by intravenous administration.

Preparations according to the present invention comprise one or more of the imidazolines at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the imidazolines, the concentration is preferably not lower than about 0.3%, in order to ensure an easy ingestion of the required doses of the one or more imidazolines. The treatment of patients with the preparations comprising one or more of the imidazolines is carried out preferably by one or more administrations of a dose of the one or more imidazoline which over time is sufficient to substantially inhibit NF-κB. If required, the doses can be administered daily or divided into several partial doses which are administered at intervals of several hours. In particular cases, the preparations can be used in conjunction with or following one or more other therapies such as radiation or chemotherapy. The administered dose of the one or more imidazolines is dependent both on the patient (species of warm-blooded animal or human) to be treated, the general condition of the patient to be treated, and on the type of disease to be treated or type of organ transplant or skin graft.

The present invention is useful as an immune suppressant for inhibiting autoimmune diseases and rejection of organ and skin transplants because NF-κB activation plays a significant role in immune disorders (Ghosh et al., Ann. Rev. Immunol. 16: 225-260 (1998)). Activation of the NF-κB results in the active transcription of a great variety of genes encoding many immunologically relevant proteins (Baeuerle and Henkel, Ann. Rev. Immunol. 12: 141-17 (1994); Daelemans et al., Antivir. Chem. Chemother. 10: 1-14 (1999)). In the case of the human immunodeficiency virus (HIV) infection results in NF-κB activation, which results in regular viral persistence (Rabson et al., Adv. Pharmacol. 48: 161-207 (2000); Pati et al., J. Virol. 77: 5759-5773 (2003); Quivy et al., J. Virol. 76: 11091-11103 (2002); Amini et al., Oncogene 21: 5797-5803 (2002); Takada et al., J. Virol. 76: 8019-8030 (2002); Chen-Park et al., J. Biol. Chem. 277: 24701-24708 (2002); Ballard, Immunol. Res. 23: 157-166 (2001); Baldwin, J. Clin. Invest. 107: 3-6 (2001); Calzado et al., Clin. Exp. Immunol. 120: 317-323 (2000); Roland et al., DNA Cell Biol 18: 819-828 (1999); Boykins et al., J. Immunol. 163: 15-20 (1999); Asin et al., J. Virol. 73: 3893-3903 (1999); Sato et al., AIDS Res. Hum. Retroviruses 14:, 293-29 (1998)). HIV-1 replication is regulated through an variety of viral regular proteins as well as cellular transcription factors (in particular NF-κB) that interact with the viral long terminal repeat (LTR) (Asin et al., J. Virol. 73: 3893-3903 (1999)). HIV-1 is able to enter a latent state in which the integrated provirus remains transcriptionally silent. The ability to continue to infect cells latently aids the virus to establish persistent infections and avoid the host immune system. The latent virus can establish large reservoirs of genetic variants in T-cells residing in lymphoid tissue. In addition, a recent study implicates NF-κB with the reactivation of latent HIV in T-cells in patents undergoing antiviral therapy (Finzi et al., Science 278: 1295-1300 (1997)).

The present invention is useful for treating inflammation disorders because NF-κB activation plays a significant role in inflammation disorders. NF-κB is activated by TNF and other pro-inflammatory cytokines. Inhibition of NF-κB activation by non-toxic inhibitors could, therefore, have clinical use in the treatment of many inflammatory disordersrheumatoid arthritis, inflammatory bowel disease, astma, chronic obstructive pulmonary disease (COPD) osteoarthritis, osteoporosis and fibrotic diseases. Related information on this can be found in (Feldmann et al., Ann. Rheum. Dis. 61: Suppl 2, ii13-18 (2002); Gerard and Rollins, Nat. Immunol. 2: 108-115 (2001); Hart et al., Am. J. Respir. Crit. Care Med. 158: 1585-1592 (1998); Lee and Burckart, J. Clin. Pharmacol. 38: 981-99 (1998); Makarov, Arthritis Res. 3: 200-206 (2001); Manna et al., J. Immunol. 163: 6800-6809 (1999); Miagkov et al., Proc. Natl. Acad. Sci. USA 95: 13859-13864 (1998); Miossec, Cell. Mol. Biol. (Noisy-le-grand) 47: 675-678 (2001); Roshak et al., Curr. Opin. Pharmacol. 2: 316-321 (2002); Tak and Firestein, J. Clin. Invest. 107: 7-11 (2001); Taylor, Mol. Biotechnol. 19: 153-168 (2001); Yamamoto and Gaynor, J. Clin. Invest. 107: 135-142 (2001); Zhang and Ghosh, J. Endotoxin Res. 6: 453-457 (2000)).

Models for demonstrating the compounds disclosed herein inhibitory effect on inflammation include the following.

Septic Shock model: Ref. Journal of Clinical Investigation 100: 972-985 (1997). Role of NF-κB in the mortality of Sepsis. Animal model: Female BALB/c mice, aged 10-12 wk, 18-20 g were injected intraperitoneally with a mixture of *E. coli* LPS (Sigma), 1.75 μg in 0.1 mL sterile PBS, pH 7.4) and D-galactosamine (Sigma, 15 mg in 0.1 mL sterile PBS), in order to sensitize them to the lethal effects of LPS (see also, Proc. Natl. Acad. Sci. USA 76: 5939-5943 (1979) and J. Exp. Med. 165, 657-663 (1987). Mortalilty was monitored after 4, 8, 12, 16, 20, and 24 hours.

Inflammation model: Ear edema using PMA as described by Chang, Eur. J. Pharmacol. 142: 197-205 (1987). 20 μL of imidazoline (various concentrations), dexamethasone (40 μg/ear) or vehicle (DMSO: Ethanol; 25:75 v/v) was applied topically to the right ear of mice 30 minutes before and 30 minutes after the application of 20 μL of PMA (5 μg/ear) dissolved in ethanol. Ear swelling was measured 6 hours after PMA application using a microgauge and expressed as the mean difference in thickness between the treated (right) and untreated (left) ears. A value of $p<0.05$ was considered statistically significant.

The following examples are intended to promote a further understanding of the present invention.

EXAMPLES 1-20

Experimental Section

Dl-(3S,4S)-1-Benzyl-4-methyl-2,5-diphenyl-4,5-dihydro-1H-imidazole-4-carboxylic acid SP-1-61 (1) was made as follows.

A solution of benzaldehyde (0.06 g, 0.57 mmol), benzylamine (0.061 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using 1:1 dichloromethane/hexanes mixture (0.155 g, 74%). $^1$H NMR (300 MHz) (DMSO-$d_6$): δ 1.8 (3H, s), 4.05 (1H, d, J=15 Hz), 4.95 (1H, d, J=14.8 Hz), 5.05 (1H, s), 7.05 (2H, s), 7.25-7.54 (8H, m), 7.74 (2H, t, J=7.2 Hz), 7.83 (1H, t, J=6.9 Hz), 8.0 (2H, d, J=8.4 Hz); $^{13}$C NMR (75 MHz) (DMSO-$d_6$): δ 25.2, 48.8, 70.4, 73.3, 122.3, 127.8, 128.3, 128.5, 128.9, 129.1, 129.3, 129.6, 129.7, 132.3, 133.2, 134, 166.1, 169.5; IR (neat): 3350 cm$^{-1}$, 1738 cm$^{-1}$; HRMS (EI): calculated for $C_{24}H_{22}N_2O_2$ $[M-H]^+$ 369.1603, found $[M-H]^+$ 369.1610; M.P.: decomposes at 185-190° C.

Dl-(3S,4S)-1-Benzyl-5-(4-methoxyphenyl)-4-methyl-2-phenyl-4,5-dihydro-1H-imidazole-4-carboxylic acid SP-1-63 (2) was made as follows.

A solution of p-anisaldehyde (0.077 g, 0.57 mmol), benzylamine (0.061 g, 0.57 mmol) in dry dichloromethane (15 mL) was refluxed under nitrogen for 2 hours. 2-Phenyl-4- methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using 1:1 dichloromethane/hexanes mixture (0.180 g, 78%). 1H NMR (300 MHz) ($CDCl_3$+2 drops DMSO-$d_6$): δ 1.8 (3H, s), 3.8 (3H, s), 3.95 (1H, d, J=15.3 Hz), 4.5 (1H, s), 4.9 (1H, d, J=15 Hz), 6.83-6.92 (4H, m), 7.08-7.19 (3H, m), 7.3-7.4 (3H) dd, $J_1$=5.1 Hz, $J_2$=1.8 Hz), 7.54-7.62 (2H, t, J=7.2 Hz), 762-7.68 (1H, t, J=7.2 Hz), 7.9 (2H, d, J=6.9 Hz); $^{13}$C NMR (75 MHz) ($CD_3OD$): δ 25.3, 48.8, 55.6, 70.9, 74.1, 115.2, 122.2, 123, 125.5, 127.9, 128.4, 129.2, 129.3, 129.6, 129.9, 132.8, 134.2, 161.1, 166.3, 168.4; IR (neat): 3388 $cm^{-1}$ 1738 $cm^{-1}$; HRMS(EI): calculated for $C_{25}H_{24}N_2O_3$ $[M-H]^+$ 397.1709, found $[M-H]^+$ 399.1717; M.P.: decomposes at 205-208° C.

Dl-(3S,4S)-1-(4-Fluorophenyl)-4-methyl-2,5-diphenyl-4,5-dihydro-1H-imidazole-4-carboxylic acid SP-1-101 (3) was made as follows.

A solution of benzaldehyde (0.060 g, 0.57 mmol), 4-fluoroaniline (0.063 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using 1:1 dichloromethane/hexanes mixture (0.160 g, 74%). $^1$H NMR (300 MHz) (DMSO-$d_6$): δ 1.98 (3H, s), 5.98 (1H, s), 7.05-7.65 (14H, m); $^{13}$C NMR (75 MHz) (DMSO-$d_6$) δ 25.2, 71.2, 77.9, 116.9, 117, 117.1, 117.3, 123, 125.1, 125.3, 129.3, 129.4, 129.6, 130.1, 130.3, 130.4, 130.5, 132.5, 133.3, 134.5, 160.4, 163.7, 165.3, 170.4; IR (neat): 3450 $cm^{-1}$, 1744 $cm^{-1}$. HRMS (EI): calculated for $C_{23}H_{19}FN_2O_2$ $[M-H]^+$ 373.1352, found $[M-H]^+$ 373.1359; M.P.: decomposes at 230-232° C.

Dl-(3S,4S)-1-Benzyl-2,4,5-triphenyl-4,5-dihydro-1H-imidazole-4-carboxylic acid SP-1-125 (4) was made as follows.

A solution of benzaldehyde (0.6 g, 5.7 mmol), benzylamine (0.61 g, 5.7 mmol) in dry dichloromethane (120 mL) was refluxed under nitrogen for 2 hours. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 hours and then stirred overnight at room temperature. The product was purified by silica-gel column chromatography with 1:5 ethanol/ethyl acetate to afford 2.1 g of product in 65% yield as an off-white solid. $^1$H NMR (300 MHz) ($CDCL_3$): δ 3.8 (1H, d, J=15.6 Hz), 4.62 (1H, d, J=15.6 Hz), 4.98 (1H, s), 6.58 (2H, d, J=8.1 Hz), 7.05-7.65 (16H, m), 7.9 (2H, d, J=7.2 Hz); $^{13}$C NMR (75 MHz) ($CDCl_6$) δ 29.7, 48.3, 75.6, 79.1, 123.1, 125.7, 126.7, 127.3, 127.4, 127.9, 128.1, 128.2, 128.8, 128.9, 129, 129.3, 132.9, 133.8, 136, 143.1, 164.8, 168.1; IR (neat): 3400 $cm^{-1}$ (very broad), 1738 $cm^{-1}$; HRMS (EI): calculated for $C_{29}H_{24}N_2O_2$ $[(M-H)\ CO_2]^+$387.1526 and observed $[M-H)—CO_2]^+$ 387.1539; M. P.: decomposes at 153-155° C.

Dl-(3S,4S)-1-Benzyl-4-(1H-indol-3-ylmethyl)-2,5-diphenyl-4,5-dihydro-1H-imidazole-4-carboxylic acid SP-1-128 (5) was made as follows.

A solution of benzaldehyde (0.6 g, 5.7 mmol), benzylamine (0.61 g, 5.7 mmol) in dry dichloromethane (120 mL) was refluxed under nitrogen for 2 hours. 4-(1H-Indol-3-ylmethyl)-2-phenyl-4H-oxazol-5-one (1.65 g, 5.7 mmol) and chlorotrimethylsilane (0.8 g, 7.4 mmol) were added and the mixture was refluxed under nitrogen for 6 hours and then stirred overnight at room temperature. The product was purified by silica-gel column chromatography with 1:5 ethanol/ethyl acetate to afford 3.1 g of product in 68% yield as an off-white solid. $^1$H NMR (300 MHz) (DMSO-$d_6$): δ 3.95 (1H, d, J=16.2 Hz), 4.6 (1H, d, J=16.2 Hz), 5.25 (1H, s), 6.1 (2H, d, J=7.8 Hz), 6.9-7.3 (5H, m), 7.3-8.0 (15H, m), $^{13}$C NMR (75 MHz) (DMSO-$d_6$) δ 169.6, 166, 136.5, 133.7, 132.5, 132.3, 129.7, 129.4, 128.9, 128.7, 128.6, 127.9, 127.8, 126.7, 126.6, 122.7, 121.4, 119, 111, 105.8, 74.4, 70.4, 48.5, 32.3; IR (neat): 3420 $cm^{-1}$ (very broad), 1741 $cm^{-1}$; HRMS(EI); calculated for $C_{32}H_{27}N_3O_2$ $[M-H]^+$ 484.2025 and observed $[M-H]^+$ 484.2011; M.P.: decomposes at >250° C.

Dl-(3S,4S)-1-Benzyl-4-methyl-2-phenyl-5-pyridin-4yl-4,5-dihydro-1H-imidazole-4-carboxylic acid SP-1-150 (6) was made as follows.

A solution of pyridin-4-carboxalaldehyde (0.061 g, 0.57 mmol), benzylamine (0.061 g, 0.57 mmol) in dry dichloromethane (15 mL) was refluxed under nitrogen for 2 hours. 2-Phenyl-4-methyl 4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was isolated using 4:1 ethyl acetate/methanol as an off-white solid (0.161 g, 76%). $^1$H NMR (300 MHz) (DMSO-$d_6$): δ 1.8 (3H, s), 4.24 (1H, d, J=15.9 Hz), 4.9 (1H, d, J=14.8 Hz), 5.15 (1H, s), 7.0-7.15 (2H, m), 7.25-7.35 (3H, m), 7.45-7.5 (2H, m), 7.7-7.9 (3H, m), 7.95-8.05 (2H, m), 8.6-8.7 (2H, m); $^{13}$C NMR (75 MHz)(DMSO-$d_6$) δ 25.1, 49.1, 70.6, 71.7, 122.1, 123, 127.9, 128.4, 128.8, 129.2, 129.4, 132.8, 133.9, 141.4, 149.8, 166.5, 169.05; IR (neat); 3400 $cm^{-1}$, 1746 $cm^{-1}$; HRMS (EI): calculated for $C_{23}H_{21}N_3O_2$ $[M-H]^+$ 370.1556, found $[M-H]^+$ 370.1556; M.P. : decomposes at 185-190° C.

Dl (3S,4S)-4-Methyl-2,5-diphenyl-4,5-dihydro-1H-imidazole-4-carboxylic acid: 16/17 [JK1-1-135] (7) was made as follows.

To a well-stirred suspension of imidazoline-4-carboxylic acid 10 (0.1 gm, 0.27 mmol) and cyclohexene (0.1 mL, 1.25 mmol) in dry THF (30 mL) added 10% Pd/C (45 mg, 0.06 mmol). The suspension was refluxed for 36 hours. The reaction mixture cooled to room temperature and ethanol (10 mL) was added. The mixture was filtered through a Celite bed, washed with ethanol and the filtrate was evaporated under reduced pressure. The crude product was purified by column silica-gel chromatography using ethanol, to yield a white solid (0.070 g, 93%). $^1$H NMR (300 MHz) (DMSO-$d_6$) δ 1.76 (s, 3H), 5.34 (s, 1H), 7.34-7.36 (b, 5H), 7.69 (dd, J=8.1, 7.2, 2H), 7.81 (1H, dd, $J_1$=6.9 Hz and $J_2$=7.2 Hz), 8.15 (2H, d, J=8.4 Hz); $^{13}$C NMR (75 MHz) (DMSO-$d_6$): 25.32, 55.66, 70.79, 72.57, 123.12, 128.24, 128.96, 129.42, 129.67, 130.12, 135.42, 136.24, 164.24, 170.77; IR (neat) 1734 $cm^{-1}$, 1616 $cm^{-1}$; MS (EI): calculated for $C_{17}H_{16}N_2O_2$ (m/z) 280.12 observed m/z: 280.1; M.P.: decomposes at 222-224° C.

Dl-(3S,4S)-1-(4-Fluorophenyl)-4-methyl-2-phenyl-4,5-dihydro-1H-imidazole-4,5-dicarboxylic acid 5-ethyl ester SP-1-175 (8) was made as follows.

A solution of ethyl glyoxalate (0.058 g, 0.57 mmol) as 50% solution in toluene (1.03 g/ml), 4-fluoroaniline (0.063 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was purified by silica-gel column chromatography using 4:1 ethyl acetate/methanol, to yield a white solid (0.152 g, 72%). $^1$H NMR (300 MHz) ($CD_3OD$): δ 1.2 (3H, t, J=7.2 Hz), 2.03 (3H, s), 4.9 (2H, dq, $J_1$=7.2 Hz, $J_2$=2.1 Hz), 5.48 (1H, s), 7.1-7.8 (9H, m); $^{13}$C NMR (75 MHz) ($CD_3OD$): δ 169.9, 166.2, 164.0, 162.1, 134.4, 131.5, 129.7, 129.6, 129.5, 129.3, 121.8, 116.9, 116.7, 75.1, 69.1, 62.9, 24.2, 12.8; 1R (neat): 3450 $cm^{-1}$, 1743 $cm^{-1}$; HRMS (EI): calculated for $C_{20}H_{19}FN_2O_4$ $[M-H]^+$ 369.1251, and observed $[M-H]^+$ 369.1255; M.P. decomposes at 190-193° C.

Dl-(3S,4S)-1-Benzyl-4-methyl-2-phenyl-5-pyridin-4-yl-4,5-dihydro-1H-imidazole-4-carboxylic acid ethyl ester JK-1-183 (9) was made as follows.

To a well-stirred suspension of dl-(3S,4S)-1-Benzyl-4-methyl-2-phenyl-5-pyridin-4yl-4,5-dihydro-1H-imidazole-4-carboxylic acid 12 (0.1 g, 0.27 mmol) in dry dichloromethane (30 mL) at 0° C. added a solution of oxallyl chloride (0.14 g, 1.1 mmol) in dry dichloromethane (5 mL). A solution of DMF (0.001 mL) was added to the reaction mixture and was stirred at 0° C. for another 2 hours. The dichloromethane was evaporated under vacuum and the reaction mixture cooled to 0° C. after which absolute ethanol (20 mL) was added. The solution was allowed to stir for an additional 1 hour. The solvent was evaporated under vacuum and the reaction mixture diluted with dichloromethane (30 mL) and washed with saturated sodium bicarbonate (1-0 mL) and water (10 mL). The organic layer was dried over sodium sulfate and was concentrated under vacuum to yield crude product, which was further purified by silica-gel column chromatography using ethyl acetate, to yield a pale yellow oil (0.097 gm, 91%). $^1H$ NMR (300 MHz) ($CDCl_3$): δ 0.86 (3H, t, J=7.2 Hz), 1.57 (3H, s), 3.64 (2H, q, J=7.2 Hz), 3.83 (1H, d, J=15.3 Hz), 4.27 (1H, s), 4.77 (1H, d, J=15.3, Hz), 6.97 (2H, dd, $J_1$=7.2 Hz and $J_2$=2.4 Hz), 7.22-7.54 (6H, m), 7.31-7.54 (2H, m), 7.78-7.81 (2H, m), 8.59-8.61 (2H, m). $^{13}C$ NMR (75 MHz) ($CDCl_3$): δ 13.45, 27.13, 49.47, 60.83, 71.87, 77.94, 122.56, 127.79, 127.93, 128.55, 128.70, 130.21, 130.51, 135.82, 146.59, 149.75, 166.02, 171.37; IR (neat): 1734 $cm^{-1}$; MS (EI): calculated for $C_{25}H_{26}N_2O_2$ (m/z) 399.19 observed m/z: 399.3.

Dl-(3S,4S)-1-Benzyl-4-methyl-2,5-diphenyl-4,5-dihydro-1H-imidazole-4-carboxylic acid ethyl ester JK-1-186 (10) was made as follows.

To a well-stirred suspension of imidazoline-4-carboxylic acid 10 (0.1 gm, 0.27 mmol) in dry methylene chloride (30 mL) at 0° C. added a solution of oxallyl chloride (0.14 g, 1.1 mmol) in dry dichloromethane (5 mL). A solution of DMF (0.001 mL) in dry dichloromethane (1 mL) was added to the reaction mixture and was stirred at 0° C. for another 2 hours. The dichloromethane was evaporated under vacuum and the reaction mixture cooled to 0° C. after which absolute ethanol (20 mL) was added. The solution was allowed to stir for an additional 1 hour. The solvent was evaporated under vacuum and the reaction mixture diluted with dichloromethane (30 mL) and washed with saturated sodium bicarbonate (10 mL) and water (10 mL). The organic layer was dried over sodium sulfate and was concentrated under vacuum to yield crude product, which was further purified by silica-gel column chromatography using ethyl acetate, to yield colorless oil (0.095 gm, 89%). $^1H$ NMR (300 MHz, $CDCl_3$): δ 0.84 (3H, t, J=7.2 Hz), 1.57 (3H, s), 3.60 (2H, q, J=7.2 Hz), 3.85 (1H, d, J=15.3 Hz), 4.32 (1H, s), 4.74 (1H, d, J=15.3 Hz), 6.98 (2H, dd, $J_1$=6.9 Hz and $J_2$=2.1 Hz), 7.27-7.35 (m, 8H), 7.49-7.51 (2H, m), 7.76-7.79 (2H, m); $^{13}C$ NMR (75 MHz, $CDCl_3$): δ 13.80, 27.13, 49.12, 60.06, 71.31, 127.98, 128.03, 128.12, 128.67, 129.02, 129.11, 130.96, 136.40, 136.80, 166.11, 171.78; IR (neat); 1730 $cm^{-1}$, 1495 $cm^{-1}$; MS (EI): calculated for $C_{26}H_{26}N_2O_2$ (m/z) 398.2 observed m/z=398.9.

Dl-(3S,4S)-1-Methoxycarbonylmethyl-4-methyl-2,5-diphenyl-4,5-dihydro-1H-imidazole-4-carboxylic acid JK-1-199 (11) were made as follows.

To a well stirred solution of 2-Phenyl-4-methyl-4H-oxazolin-5-one (0.5 g, 2.85 mmol) and TMSCl (0.37 g, 3.42 mmol) in dry dichloromethane (50 mL) added a solution of (Benzylidene-amino)-acetic acid methyl ester (0. gm, mmol) in dry methylene chloride (20 mL) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (0.70 g, 70%). $^1H$ NMR (300 MHz) ($CD_3OD$): δ 1.99 (3H, (1H, d, J=18.3 Hz), 4.53 (1H, d, J=18.3 Hz), 5.39 (1H, s), 7.47-7.50 (5H, m), 7.74-7.87 (5H, m). $^{13}C$ NMR (75 MHz) ($CD_3OD$): δ 24.23, 52.09, 70.83, 75.38, 121.84, 128.26, 128.69, 129.52, 129.75, 131.78, 134.02, 167.59, 168.62, 169.19; IR (neat): 3468 $cm^{-1}$, 1747 $cm^1$; MS (EI): calculated for $C_{20}H_{20}N_2O_4$ (m/z) 352.14 observed m/z=353.2; M.P.: decomposes at 215-217° C.s), 3.67 (3H, s), 3.96.

1-Benzyl-5-(4-methoxy-phenyl)-2,4-dimethyl-4,5-dihydro-1H-imidazole-4-carboxylic acid SP-1-189 (12) was made as follows.

A solution of p-anisaldehyde (1.4 g, 10.4 mmol), benzylamine (1.11 g, 10.4 mmol) in dry dichloromethane (150 mL) was refluxed under nitrogen for 2 h. 2,4-dimethyl-4H-oxazolin-5-one SP-1-188 (1f) (1 g, 8.7 mmol) and chlorotrimethylsilane (1.22 g, 11.3 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (1.9 g, 65%). $^1H$ NMR (300 MHz) ($CDCl_3$): δ 1.13 (3H, s), 2.43 (3H, s), 3.83 (3H, s), 4.17 (1H, d, J=15.9 Hz), 4.57 (1H, d, J=15.9 Hz), 5.8 (1H, s) 6.92 (2H, d, J=8 Hz), 7.05 (2H, d, J=8 Hz) 7.2-7.4 (5H, m); $^{13}C$ NMR (75 MHz) ($CDCl_3$): δ 12.3, 21.9, 47.8, 55.2, 70.4, 114.3, 125.2, 126.9, 128.5, 129.3, 133.3, 159.9, 163.2, 174.8; IR (neat): 3388 $cm^{-1}$; 1738 $cm^{-1}$; HRMS (EI): calculated for $C_{20}H_{22}N_2O_3$ $[M-H]^+$(m/z)=337.1552, found (m/z) 337.1548.

Dl-(3S,4S)-1-(2-Ethoxycarbonyl-ethyl)-4-methyl-2,5-diphenyl-4,5-dihydro-1H-imidazole-4-carboxylic acid JK-1-215 (13) was made as follows.

To a well stirred solution of 2-Phenyl-4-dimethyl-4H-oxazolin-5-one (1.0 g, 5.7 mmol) and TMSCl (1 mL, 6.8 mmol) in dry dichloromethane (80 mL) added a solution of 3-(Benzylidene-amiono)-propionic acid ethyl ester (1.4 gm, 6.8 mmol) in dry methylene chloride (60 mL) and the mixture was refluxed under nitrogen for 10 hours and then stirred overnight at room temperature. The reaction mixture was evaporoated to dryness under vacuum. The product was precipitated out as a white solid using a 1:1 dichloromethane/hexanes mixture (1.08 g, 51.4%). $^1H$ NMR (500 MHz) ($CD_3OD$): δ 1.17 (t, J=7.5, 3H), 1.9 (s, 3H), 2.47-2.52 (m, 1H), 2.52-2.71 (m, 1H), 3.34-3.39 (m, 1H), 3.40-4.09 (m, 3H), 5.42 (s, 1H), 7.46-7.49 (m, 5H), 7.72-7.87 (m, 5H); $^{13}C$ NMR (100 MHz) ($CD_3OD$): δ 13.35, 24.87, 30.64, 41.64, 61.00, 70.94, 73.51, 122.77, 128.99, 129.21, 129.80, 130.10, 132.78, 134.09, 167.32, 169.81, 170.9. IR (neat): 3481 $cm^{-1}$, 1743 $cm^{-1}$; MS (EI): calculated for $C_{22}H_{24}N_2O_4$ (m/z) 380.44 observed m/z=380.7. M.P.: decomposes at 218-220° C.

Dl-(3S,4S)-1-(1-Methoxycarbonyl-ethyl)-4-methyl-2,5-diphenyl-4,5-dihydro-1H-imidazole-4-carboxylic acid JK-1-192 (14) was made as follows.

To a well stirred solution of 2-Phenyl-4-methyl-4H-oxazolin-5-one (0.25 g, 1.5 mmol) and TMSCl (0.23 mL, 1.8 mmol) in dry dichloromethane (50 mL) added a solution of 2-(Benzlidene-amino)-propionic acid methyl ester (0.34 gm, 1.8 mmol) in dry methylene chloride (20 mL) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (0.340 g, 66%). $^1$H NMR (300 MHz) ($CD_3OD$): δ 1.19 (d, J=6.9, 3H), 2.06 (s, 3H), 3.38 (s, 3H), 4.89 (q, J=6.9, 1H), 544 (s, 1H), 7.43-7.46 (5H, m), 7.75-7.85 (5H, m). $^{13}$C NMR (75 MHz) ($CD_3OD$): δ 14.9, 25.6, 52.7, 56.7, 71.9, 72.5, 122.2, 128.8, 128.9, 129.6, 130.0, 134.5, 135.8, 169.2, 169.4, 170.4, IR (neat): 3431 $cm^{-1}$, 1740 $cm^{-1}$; MS (EI): calculated for $C_{21}H_{22}N_2O_4$ (m/z) 366.4 observed m/z=366.6. M.P.: decomposes at 222-226° C.

1-Benzyl-4-methyl-2,5-diphenyl-4,5-dihydro-1H-imidazol-4-yl)-methanol 14 [JK-1-123] (15) was made as follows.

To a well stirred suspension of Lithium aluminum hydride (0.12 gm, 0.3 mmol) in dry THF (5 mL) added a solution of 1-Benzyl-4-methyl-2,5-diphenyl-4,5-dihydro-1H-imidazole-4-carboxylic acid (0.1 gm, 0.27 mmol) in dry THF (5 mL) at 0° C. drop wise, stirred at same temperature for 15 min quenched with ice cold saturated ammonium chloride solution [Caution: Ammonium chloride solution kept at 0° C. for about 30 minutes; and should be added with extreme care; highly exothermic reaction and the reaction mixture should be at 0° C.] then added about 10 mL of 10% HCl. The reaction mixture diluted with excess of ethyl acetate (100 mL) washed with water (20 mL) dried over anhydrous sodium sulfate, filtered through a fluted filter paper and the organic layer evaporated under reduced pressure to yield the crude product which was purified by column chromatography using ethyl acetate. Yield: 79%; viscous oil, IR (neat): 3314, 2928, 1643, 1516; δ H (300 MHz, $CD_3Cl_3$): δ 1.25 (s, 3H), 3.48 (d, J=12, 1H), 3.56 (d, J=11.8, 1H), 3.75 (d, 12.9, 1H), 3.87 (s, 1H), 3.94 (d, J=12.9, 1H), 7.28-7.54 (m, 13H), 7.77-7.79 (m, 2H), 8.06 (brs, 1H); δ C (75 MHz, $CDCl_3$): δ 17.25, 51.67, 61.54, 66.28, 66.93, 127.266, 127.68, 128.26, 128.56, 128.82, 129.06, 131.77, 135.48 138.03, 139.90, 167.91; m/z: 357.2.

1-Benzyl-4-(2-methoxycarbonyl-ethyl)-2,5-diphenyl-4,5-dihydro-1H-imidazole-4-carboxylic acid SP-1-201 (16) was made as follows.

A solution of benzaldehyde (0.252 g, 2.4 mmol), benzylamine (0.258 g, 2.4 mmol) in dry dichloromethane (100 mL) was refluxed under nitrogen for 2 hours. 3-(5-Oxo-2-phenyl-4,5-dihydro-oxazol-4-yl)-propionic acid methyl ester SP-1-182 (1e) (0.5 g, 2 mmol) and chlorotrimethylsilane (0.282 g, 2.6 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (0.54 g, 60%). $^1$H NMR (300 MHz) ($CDCl_3$): δ 2.05-2.25 (2H, m), 2.3-2.5 (2H, m), 3.55 (3H, s), 4.38 (2H, ddd, $J_1$=4 Hz, $J_2$=9 Hz, $J_3$=25 Hz), 4.86 (1H, q, J=3.3), 7.1-7.6 (12H, m), 7.7-7.9 (4H, m); $^{13}$C NMR (75 MHz) ($CDCl_3$): δ 27.6, 30.1, 43.3, 51.6, 52.7, 127.1, 127.2, 127.3, 128.2, 128.3, 131.5, 131.6, 133.3, 137.8, 167.5, 171.4, 173.6; IR (neat): 1734 $cm^{-1}$, 1653 $cm^{-1}$; MS (EI): calculated for $C_{24}H_{22}N_2O_2$ (m/z) 442.5, found (m/z) 443.

Dl-(3S,4S)-1-Benzyl-2,4-dimethyl-5-phenyl-4,5-dihydro-1H-imidazole-4-carboxylic acid 15[JK-1-238] (17) was made as follows.

To a well stirred solution of 2,4-dimethyl-4H-oxazolin-5-one (0.4 g, 3.5 mmol) and TMSCl (0.58 mL, 4.2 mmol) in dry dichloromethane (60 mL) added a solution of Benzyl-benzylidene-amine (0.82 gm, 4.2 mmol) in dry methylene chloride (40 mL) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (0.60 g, 60%). $^1$H NMR (300 MHz) ($CD_3OD$): δ 1.11 (s, 3H), 2.47 (s, 3H), 4.17 (d, J=16.2, 1H), 4.63 (q, J=16.2, 1H), 5.84 (s, 1H), 7.04-7.07 (m, 2H), 7.27-7.42 (m, 7H). $^{13}$C NMR (75 MHz) ($CD_3OD$): δ 12.62, 22.12, 48.27, 70.39, 71.25, 127.31, 128.83, 129.28, 129.58, 133.40, 133.46, 164.12, 175.19. IR (neat): 3431 $cm^{-1}$, 1740 $cm^{-1}$; MS (EI); calculated for $C_{19}H_{20}N_2O_2$ (m/z) 308.37 observed m/z 308.3, M.P.; decomposes at 232-234° C.

Dl-(3S,4S)-1-Benzyl-2,4-diphenyl-5-pyridin-4-yl-4,5-dihydro-1H-imidazole-4-carboxylic acid SP-1-195 (18) was made as follows.

A solution of pyridin-4-carboxylaldehyde (0.61 g, 0.57 mmol), benzylamine (0.61 g, 5.7 mmol) in dry dichloromethane (120 mL) was refluxed under nitrogen for 2 hours. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 hours and then stirred overnight at room temperature. The product was purified by precipitation from dichloromethane/ether mixture to afford 1.35 g of the product in 55% yield as an off-white solid. $^1$H NMR (300 MHz) ($CDCl_3$): δ 4 (1H, d, J=15.6 Hz), 5.0 (1H, d, J=15.6 Hz), 5.38 (1H, s), 7.1-7.65 (17H, m), 8.5 (2H, d, J=7.2 Hz); $^{13}$C NMR (75 MHz) ($CDCl_3$): δ 45.2, 66.3, 75.6, 123.7, 126.5, 126.9, 128.5, 128.6, 128.8, 129.2, 129.3, 131.9, 133.5, 134.4, 136.2, 143.4, 149.7, 166.6, 166.9; IR (neat): 3400 $cm^{-1}$ (very broad), 1733 $cm^{-1}$; MS (EI): calculated for $C_{24}H_{22}N_2O_2$ (m/z) 434.34, found (m/z) 434.2.

Compounds 19 and 20 were made as follows.

Synthesis of 1-Benzyl-4-methyl-2,5-diphenyl-4,5-dihydro-1H-imidazole-4-carboxylic acid (1-phenyl-ethyl)-amide from 1-Benzyl-4-methyl-2,5-diphenyl-4,5-dihydro-1H-imidazole-4-carboxylic acid: JK-1-309.

To a well-stirred suspension of 1-Benzyl-4-methyl-2,5-diphenyl-4,5-dihydro-1H-imidazole-4-carboxylic acid (1.0 g, 0.27 mmol) in dry methylene chloride (25 mL), (S)-(−)-1-Phenyl-ethylamine (0.36 g, 29 mmol) was added EDCI-HCl (0.57 g, 29 mmol), after five minutes added a solution of DMAP (0.35 gm, 29 mmol) in methylene chloride (10 mL) and stirred for 5-6 hours. The reaction mixture was washed with water (2×10 mL), saturated sodium bicarbonate (20 mL), water (20 mL), 2N HCl (20 mL) and then with water (30 mL). The organic layer dried over sodium sulfate and evaporated under reduced pressure. The crude product was purified by column silica-gel chromatography using ethyl acetate hexane mixture (1:1). Compound 19: Yield (0.26 g, 40.7%). {$[\alpha]_D$=+41.5°)} $^1$H NMR (300 MHz): δ 1.02 (d, J=6.9, 3H), 1.56 (s, 3H), 3.85 (d, J=15.6, 1H), 4.40 (s, 1H), 4.66 (d, J=15.6 , 1H), 4.72 (t, J=6.9, 1H), 7.07-7.09 (m, 2H), 7.17-7.55 (m, 16H), 7.69-7.73 (m, 2H); $^{13}$C NMR (75 MHz): 21.39, 27.56, 48.09, 48.73, 72.66, 126.52, 127.24, 127.71, 127.99, 128.42, 128.57, 128.67, 128.95, 129.01, 129.14, 130.75, 130.82, 137.38, 137.60, 143.29, 165.44, 171.61. Compound 20: (0.24 g, 38%). {$[\alpha]_D$=37.7°)} $^1$H NMR (300 MHz): δ 1.40 (d, J=7.2 3H), 1.61 (s, 3H), 3.77 (d, J=15.6, 1H), 4.37 (s, 1H), 4.60 (d, J=15.6, 1H), 4.75 (t, J=7.5, 1H), 6.922-7.090 (m, 2H), 7.11-7.22 (m, 13H), 7.507-7.529 (m, 3H), 7.651-7.682 (m, 2H): $^{13}$C NMR (75 MHz): 21.58, 28.08, 47.97, 48.59, 72.62, 126.66, 126.99, 127.200, 127.69, 127.96, 128.21, 128.51, 128.58, 128.64, 129.13, 129.122, 130.70, 130.83, 137.184, 137.22, 143.28, 165.35, 171.62.

EXAMPLE 21

All compounds were evaluated for their potential anti-inflammatory activity by examining the activity of NF-κB in vitro in nuclear extracts using the procedure from Breton and Charbot-Fletcher (Breton et al., J. Pharmacol. Exp. Ther. 282 459-466 (1997)). Briefly, Human Jurkat leukemia T-cells (clone E6-1; Amer. Type Culture Collection, Manassas, Va.) are grown in RPMI-1640 Media (Gibco-BRL, Bethesda, Md.) supplemented with 10% Fetal Bovine Serum, Penicillin (614 ηg/mL), Streptomycin (10 μg/mL) and Hepes Buffer, pH 7.2 at 37° C., 5% $CO_2$. The Jurkat cells ($1\times10^7$ cells/mL) are subsequently treated with various concentrations of imidazoline for 30 minutes at 37° C. followed by PMA stimulation (5.0 ng/mL) for an additional 5 hours. Nuclear extracts are incubated for 20 minutes with a double stranded Cy3 labeled NF-κB consensus oligonucleotide, 5'-AGTTGAGGGGACTTTCCCAGGC-3' (SEQ ID NO:1) at room temperature. The crude mixture is loaded on a 5% non-denaturing polyacrylamide gel prepared in 1×Tris borate/EDTA buffer and electrophoresed at 200V for 2 hours. After electrophoresis the gel is analyzed using a phosphorimager (Biorad FX PLUS) for detection of the NF-κB-DNA binding.

Figure 3:
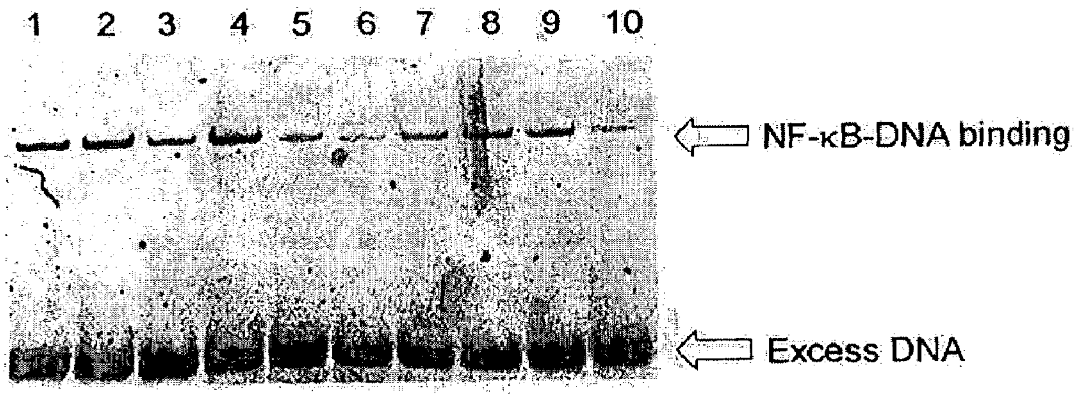
FIG. 3 is a EMSA of nuclear extracts with imidazolines 8-10. Lane 1, DNA only (control); lane 2, DNA, nuclear extract (10 μg) with p50 homodimer (control); lane 3, DNA, nuclear extract (10 μg) with PMA activation (control); lane 4, DNA, nuclear extract (10 μg) with no PMA activation (control); lane 5, DNA, nuclear extract (10 μg) after PMA activation with compound 8 (1.0 μM); lane 6, DNA, nuclear extract (10 μg) after PMA activation with compound 8 (0.1 μM); lane 7, DNA, nuclear extract (10 μg) after PMA activation with compound 9 (1.0 μM); lane 8, DNA, nuclear extract (10 μg) after PMA activation with compound 9 (0.1 μM); lane 9, DNA, nuclear extract (10 μg) after PMA activation with compound 10 (0.1 μM); lane 10, DNA, nuclear extract (10 μg) after PMA activation with compound 10 (0.1 μM).

Treatment of the cells to the imidazolines exhibited a significant inhibition of nuclear NF-κB activity. FIG. 3 clearly illustrates a decrease of nuclear NF-κB-DNA binding by imidazolines 8-10 (FIG. 3, lanes 5-10).

Cells treated with the imidazolines exhibited a significant inhibition of nuclear NF-κB activity (FIG. 3). FIG. 3 clearly illustrates a significant decrease of nuclear NF-κB-DNA binding in the presence 100 nM concentration of imidazolines 8-10 (FIG. 3, lanes 5-10).

The apparent absence of a slow moving band in lane 5 is indicative of significant (94%) NF-κB inhibition by compound 8 at 1 μM concentration in Jurkat Leukemia T-cells. Lane 6 indicates 88% inhibition of NF-κB-DNA binding in the nucleus by 100 ηM concentrations of compound 8.

EXAMPLE 22

All compounds were tested for their ability to inhibit NF-κB and the collected data is shown in Table 2. Currently, the most active compound in the series is the heterocyclic imidazoline 9 which exhibited 88% inhibition of NF-κB at 100 nM concentrations. Preliminary results indicate that the imidazolines do not exhibit significant cytotoxicity for up to 72 hours.

TABLE 2

Inhibition of NF-κB by imidazolines 1-10.

| compound | concentration | % inhibition |
|---|---|---|
| 1 | 1.0 μM | 19% |
| 2 | 1.0 μM | 68% |
| 3 | 1.0 μM | 35% |
| 4 | 1.0 μM | 65% |
| 5 | 1.0 μM | 0% |
| 6 | 0.1 μM | 84% |
| 7 | 0.1 μM | 38% |
| 8 | 0.1 μM | 88% |
| 9 | 0.1 μM | 71% |
| 10 | 0.1 μM | 22% |

The most active compound in this series was compound 8.

$IC_{50}$ values in Mammalian Jurkat cells Leukemia T cells: $IC_{50}$ value is defined as the concentration of compounds at which 50% of the protein/enzyme is inhibited in cells (Table 3).

TABLE 3

| Compound | $IC_{50}$ |
|---|---|
| 1 | 1.95 μM |
| 2 | 40 ηM |
| 3 | 6.5 ηM |
| 4 | 73 ηM |
| 5 | not tested |
| 6 | 0.3 μM |
| 7 | 20 ηM |

EXAMPLE 23

Compounds 4, 6, and 7 were tested for the inhibition of bacteria. A total of 9 bacterial strains were screened. The following Gram-negative and Gram-positive bacteria were included: *Staphylococcus aureus, Enterobacter aerogenes, Esherichia coli, Klebsiella pneumonia, Pseudomonas aeruginosa, Serratia marcescens, Bacillus cerius, Bacillus subtillus* and *micrococcus luteus.* Bacterial isolates were removed from storage, streaked on to nutrient agar plates and incubated for 18-24 hours at 35° C. A working bacterial suspension was prepared by suspending 3-5 isolated colonies in 5 mL saline solution. The turbidity of this suspension was carefully adjusted photometrically to equal that of a 0.5 McFarland standard. The zone diameters were determined by a standardized disk diffusion method using cation-supplemented Mueller-Hinton agar according to NCCLS guidelines (National Committee for Clinical Laboratory Standards. *Methods for dilution Antimicrobial Susceptibility Tests for Bacteria that Grow Aerobically.* Fifth Edition: Approved Standard M7-A5. Wayne, Pa.: NCCLS (2000)). Minimum inhibitory concentrations (MICs) were considered the lowest concentration that gave a clear zone of inhibition. The inoculated agar plates were incubated for 16-20 hours at 35° C. in ambient air. The diameters of the zones were read in millimeters. The results are shown in Table 4.

TABLE 4

| Microbe | MIC |
|---|---|
| Compound 4 | |
| *Bacillus subtillus* | 13 mm 50 μg |
| *Bacillus cereus* | 11 mm 50 μg |
| *Micrococcus luteus* | 12 mm 200 μg |
| *Staphylococcus aureus* | 12 mm 200 μg |
| Compound 6 | |
| *Micrococcus luteus* | 10 mm 200 ηg |
| Compound 7 | |
| *Micrococcus luteus* | 10 mm 56 ηg |

EXAMPLE 24

Treatment of Imidazoline in RIF-1 Murine Tumor Model

Several of the NF-κB inhibitors (compounds 1, 3, 4, and 6) were tested in animals. Tumor cells were injected, bilaterally, into the backs of mice. When tumors reached 100 $mm^3$, the mice were treated with an intraperitoneal injection of the compound. Tumor volumes were measured 3 times a week until they reached 4 times the size they were on the first treatment day. Data is recorded as "Days to 4×' or ratio of 'Days to 4×" of the treated over untreated controls.

Figure 4A:
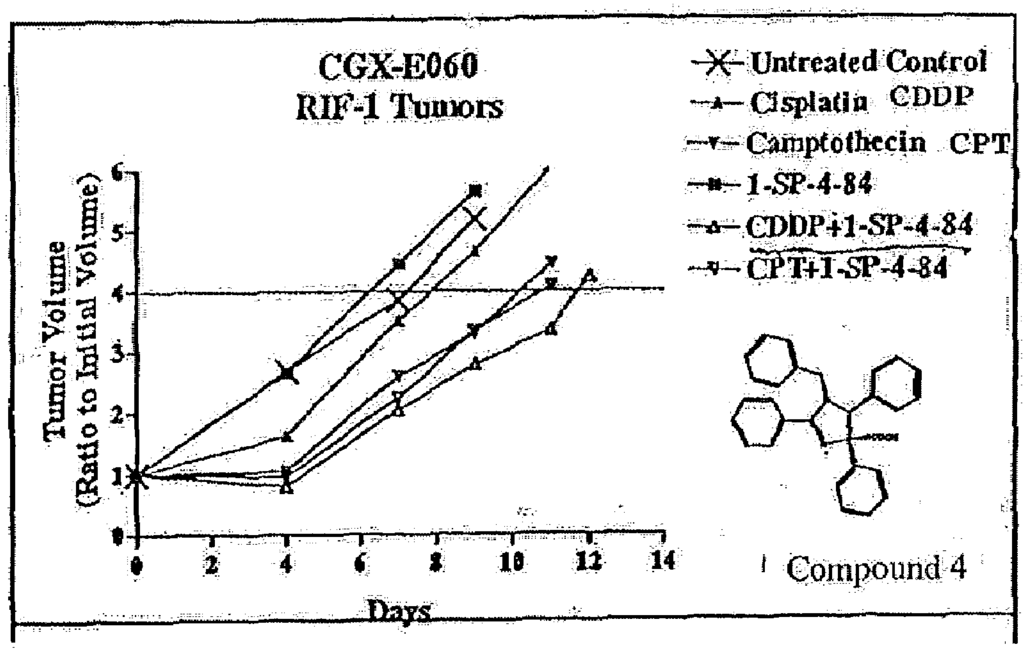
FIGS. 4A and 4B show tumor growth delay with compounds 4 and 6.

Combinational treatment of the mice with cis-platin (CDDP) and camptothecin (CPT) in the presence of compound 4 (1-SP-4-84) exhibited considerable chemopotentiation of cis-platin (FIG. 4A). In addition, this group had 4 of the 8 tumors that remained <4× its volume at day 22 of the experiment. No significant chemopotentiation of camptothecin in the presence of compound 4 was shown.

Figure 4B:
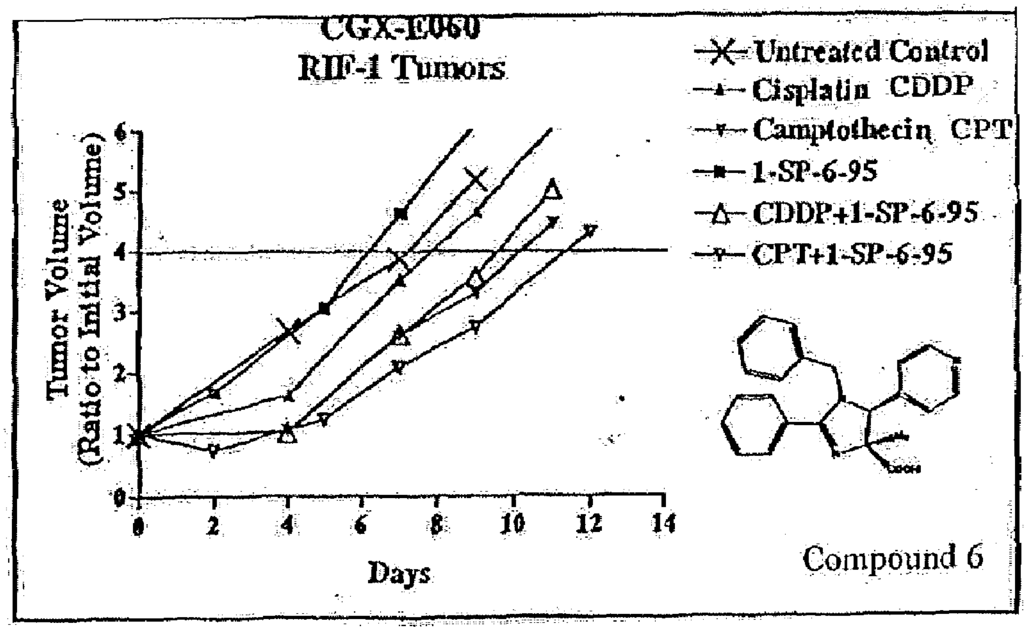

Compound 6 (1-SP-6-95) exhibited significant chemopotentiation of cis-platin as well as camptothecin (FIG. 4B). However, chemopotentiation by 6 was not as pronounced as seen with compound 4.

Combinational treatment of the mice with cis-platin (CDDP) and camptothecin (CPT) in the presence and absence of the imidazolines indicated that compounds 1 and 3 showed no significant chemopotentiation of either cis-platin or camptothecin (data not shown).

Combinational therapy of compound 4 with cis-platin showed a tumor growth delay (in days) of more than 10.26 days as compared to cis-platin (0.82 days) or camptothecin (3.79 days) alone (Table 5). In addition, half of the tumors in this RIF-1 murine model did not reach the 4× tumor volume cut-off point at day 22 days when exposed to combinational treatment with compound 4.

TABLE 5

Antitumor efficacy of imidazolines as measured by the RIF-1 murine model of tumor growth delay. CGX-E060

| Treatment | # of Tumors | Route | Dose (mg/kg) | Days to 4x (Ave ±SE) | T/C | Median | Days Delay |
|---|---|---|---|---|---|---|---|
| Untreated | 10 | — | — | 7.3 ± 0.6 | 0.0 | 7.0 | 0.00 |
| Cis-platin | 8 | IP | 4 | 8.1 ± 0.4 | 1.1 | 7.8 | 0.82 |
| Compound 1 | 8 | IP | 100 | 6.5 ± 0.3 | 0.9 | 6.4 | −0.57 |
| Compound 3 | 8 | IP | 100 | 7.6 ± 1.0 | 1.0 | 6.8 | −0.20 |
| Compound 4 | 6/8 | IP | 100 | 6.4 ± 0.2 | 0.9 | 6.5 | −0.56 |
| Compound 6 | 8 | IP | 100 | 6.6 ± 0.3 | 0.9 | 6.6 | −0.41 |
| CDDP + 1 | 8 | IP | 4/100 | 8.8 ± 0.5 | 1.2 | 9.1 | 2.05 |
| CDDP + 3 | 8 | IP | 4/100 | 8.8 ± 0.3 | 1.2 | 8.5 | 1.49 |
| CDDP + 4* | 8 | IP | 4/100 | >17.1 ± 1.9 | >2.3 | >17.3 | >10.26 |
| CDDP + 6 | 8 | IP | 4/100 | 9.8 ± 0.3 | 1.3 | 10.1 | 3.09 |
| Campto-thecin | 8 | IP | 6 | 10.3 ± 0.6 | 1.4 | 10.8 | 3.79 |
| CPT + 1 | 8 | IP | 6/100 | 10.2 ± 0.4 | 1.4 | 10.3 | 3.27 |
| CPT + 3 | 8 | IP | 6/100 | 8.8 ± 0.6 | 1.2 | 8.7 | 1.70 |
| CPT + 4 | 4/8 | IP | 6/100 | 10.8 ± 0.4 | 1.5 | 11.1 | 4.07 |
| CPT + 6 | 8 | IP | 6/100 | 11.8 ± 0.9 | 1.6 | 10.7 | 3.72 |

*This group had 4 of 8 tumors < 4x at Day 22. Abbreviations: CDDP (cis-platin) and CPT (camptothecin) and IP (intraperitoneal injection).

This data illustrates the efficacy of the imidazolines in the chemopotentiation of commonly used anticancer drugs. Inhibition of chemoresistance by these novel NF-κB inhibitors (especially compound 4) results in a significant delay of tumor growth as compared to treatment of the tumors with the anticancer drug alone.

EXAMPLE 25

Figure 5:
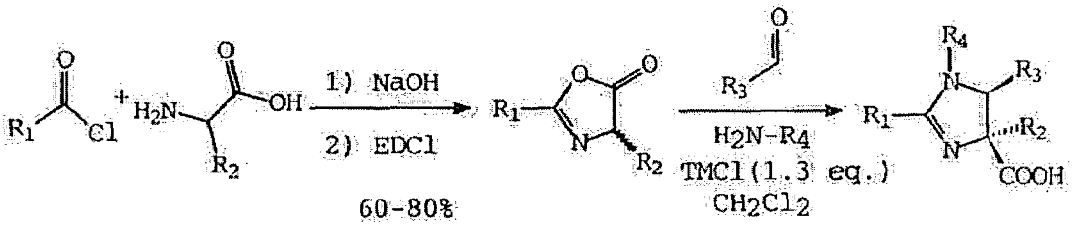
FIG. 5 shows the synthesis of imidazoline scaffolds 28-33.
Figure 5:
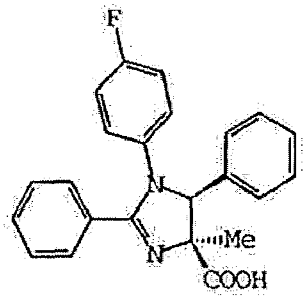
Figure 5:
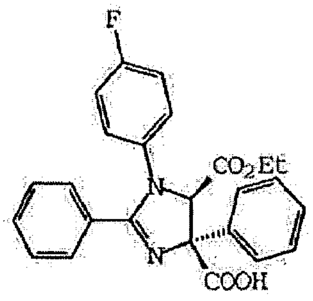
Figure 5:
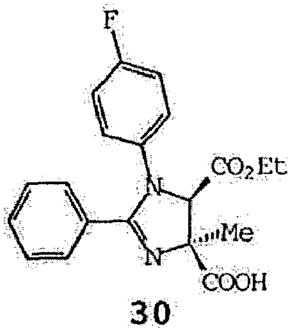
Figure 5:
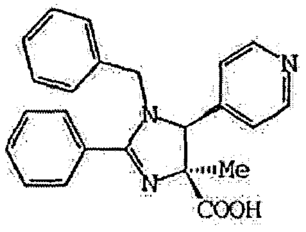
Figure 5:
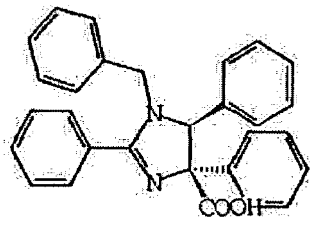
Figure 5:
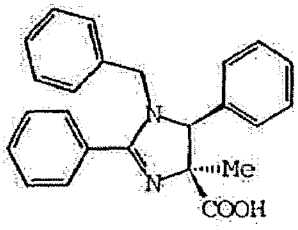

As shown in FIGS. 5 and 6, a new class of imidazoline has been synthesized which are potent inhibitors of NF-κB in T-cells.

We have recently reported a novel highly diastereoselective multicomponent one-pot synthesis of substituted imidazolines (FIG. 5) (Peddibhota et al., Org. Lett 4: 3533-3535 (2002)). These low molecular weight scaffolds contain a four-point diversity applicable to alkyl, aryl, acyl, and heterocyclic substitutions. Surprisingly, the utilization of azlactones (or oxazolones) had not yet resulted in an efficient entry into a stereoselective highly diverse class of imidazoline scaffolds. However, 1,3 dipolar cycloadditions utilizing N-methylated mesoionic oxazolones (or "munchones") are well known and provide a general route for the synthesis of pyrroles and imidazoles (Gerard and Rollines, Nat. Immunol. 2: 108-115 (2001); Hart et al., Am. J. Respir. Crit. Care Med. 158: 1885-1592 (1998); Makarov, Arthritis Res. 3: 200-206 (2001)). After screening a small number of Lewis acids we found that TMSCl promotes the reaction of oxazolones and imines to afford the imidazolines scaffolds in very good yields as single diastereomers (FIG. 6). A large library of imidazolines was prepared and several members were evaluated for their biological properties. Upon screening of these agents we found that the imidazolines were potent inhibitors of NF-κB activation. The synthesis of these compounds is described below.

Reactions were carried out in oven-dried glassware under nitrogen atmosphere, unless otherwise noted. All commercial reagents were used without further purification. All solvents were reagent grade. THF was freshly distilled from sodium/benzophenone under nitrogen. Toluene, Dichloromethane and TMSCl were freshly distilled from $CaH_2$ under nitrogen. All reactions were magnetically stirred and monitored by thin layer chromatography with Analtech 0.25-mm pre-coated silica gel plates. Column chromatography was carried out on silica gel 60 (230-400 mesh) supplied by EM Science. Yields refer to chromatographically and spectroscopically pure compounds unless otherwise stated. Melting points were determined on a Mel-Temp (Laboratory devices) apparatus with a microscope attachment. Infrared spectra were recorded on a Nicolet IR/42 spectrometer. Proton, carbon, and NMR spectra were recorded on a Varian Gemini-300 spectrometer or a Varian VXR-500 spectrometer. Chemical shifts are reported relative to the residue peaks of solvent chloroform (δ 7.24 for $^1H$ and δ 77.0 for $^{13}C$) and dimethyl sulfoxide (δ_2.49 for $^1H$ and δ 39.5 for $^{13}C$). High-resolution mass spectra were obtained at the Mass Spectrometry Laboratory of the University of South Carolina, Department of Chemistry & Biochemistry with a Micromass VG-70S mass spectrometer. Gas chromatography/low-resolution mass spectra were recorded on a Hewlet-Packard 5890 Series II gas chromatograph connected to a TRIO-1 EI mass spectrometer. All chemicals were obtained from Aldrich Chemical Co. and used as received.

TABLE 6

| Compound | IR ($cm^{-1}$) | $^1$H NMR (300 MHz) |
|---|---|---|
| 33 (2a) | 3350, 1738 | (DMSO-$d_6$): δ 1.8 (3H, s) , 4.05 (1H, d, J=15 Hz), 4.95 (1H, d, J=14.8 Hz), 5.05 (1H, s), 7.05 (2H, s), 7.25-7.54 (8H, m), 7.74 (2H, t, J=7.2 Hz), 7.83 (1H, t, J=6.9 Hz), 8.0 (2H, d, J=8.4 Hz) |
| 34 (2b) | 3388, 1738 | ($CDC1_3$ + 2 drops (DMSO-$d_6$): δ 1.8 (3H, s), 3.8 (3H, s), 3.95 (1H, d, J=15.3 Hz), 4.5 (1H, s), 4.9 (1H, d, J=15 Hz), 6.83-6.92 (4H, m), 7.08-7.19 (3H, m), 7.3-7.4 (3H, dd, $J_1$=5.1 Hz, $J_2$=1.8 Hz), 7.54-7.62 (2H, t, J=7.2 Hz), 762-7.68 (1H, t, J=7.2 Hz), 7.9 (2H, d, J=6.9 Hz); |
| 28 (2c) | 3450, 1744 | (DMSO-$d_6$): δ 1.98 (3H, s), 5.98 (1H, s), 7.05-7.65 (14H, m) |
| 31 (2d) | 3400, 1746 | (DMSO-$d_6$): δ 1.8 (3H, s), 4.24 (1H, d, J=15.9 Hz), 4.9 (1H, d, J=14.8 Hz), 5.15 (1H, s), 7.0-7.15 (2H, m), 7.25-7.35 (3H, m), 7.4-7.5 (2H, m), 7.7-7.9 (3H, m), −7.95-8.05 (2H, m), 8.6-8.7 (2H, m) |
| 29 (2e) | 3450, 1743 | ($CD_3OD$): δ 1.2 (3H, t, J=7.2 Hz), 2.03 (3H, s), 4.9 (2H, dq, J1=7.2 Hz, J2=2.1 Hz), 5.48 (1H, s), 7.1-7.8 (9H, m) |
| 40 (2g) | 3468, 1747 | ($CD_3OD$): δ 1.99 (3H, (1H, d, J=18.3 Hz), 4.53 (1H, d, J=18.3 Hz), 5.39 (1H, s), 7.47-7.50 (5H, m), 7.74-7.87 (5H, m) |
| 42 (2h) | 3431, 1740 | ($CD_3OD$): δ 1.19 (d, J=6.9, 3H), 2.06 (s, 3H), 3.38 (s, 3H), 4.89 (q, J=6.9, 1H0, 5.44 (s, 1H), 7.43-7.46 (5H, m), 7.75-7.85 (5H, m). |
| 41 (2i) | 3481, 1743 | ($CD_3OD$): δ 1.17 (t, J=7.5, 3H), 1.9 (s, 3H), 2.47-2.52 (m, 1H), 2.52-2.71 (m, 1H), 3.34-3.39 (m, 1H), 3.40-4.09 (m, 3H), 5.42 (s, 1H), 7.46-7.49 (m, 5H), 7.72-7.87 (m, 5H). |
| 37 (2j)* | 1730, 1595 | ($CDCl_3$): δ 0.84 (3H, t, J=7.2 Hz), 1.57 (3H, s), 3.60 (2H, q, J=7.2 Hz), 3.85 (1H, d, J=15.3 Hz), 4.32 (1H, s), 4.74 (1H, d, J=15.3 Hz), 6.98 (2H, dd, $J_1$=6.9 Hz and $J_2$=2.1 Hz), 7.27-7.35 (m, 8H), 7.49-7.51 (2H, m), 7.76-7.79 (2H, m). |
| 38 (2k)* | 1734, 1597 | ($CDCl_3$): δ 0.86 (3H, t, J=7.2 Hz), 1.57 (3H, s), 3.64 (2H, q, J=7.2 Hz), 3.83 (1H, d, J=15.3 Hz), 4.27 (1H, s), 4.77 (1H, d, J=15.3 Hz), 6.97 (2H, dd, $J_1$=7.2 Hz and $J_2$=2.4 Hz), 7.22-7.54 (6H, m), 7.31-7.54 (2H, m), 7.78-7.81 (2H, m), 8.59-8.61 (2H, m). |
| 45 (21)* | — | ($CDCl_3$): δ 1.25 (s, 3H), 3.48 (d, J=12, 1H), 3.56 (d, J=11.8, 1H), 3.75 (d, 12.9, 1H), 3.87 (s, 1H), 3.94 (d, J=12.9, 1H), 7.28-7.54 (m, 13H), 7.77-7.79 m, 2H), 8.06 (brs, 1H) |
| 39 (2m) | — | (DMSO-$d_6$): δ 1.76 (s, 3H), 5.34 (s, 1H), 7.34-7.36 (b, 5H), 7.69 (dd, J=8.1, 7.2, 2H), 7.81 (1H, dd, $J_1$=6.9 Hz and $J_2$=7.2 Hz), 8.15 (2H, d, J=8.4 Hz). |
| 32 (2n) | 3400, 1738 | ($CDCl_3$): δ 3.8 (1H, d, J=15.6 Hz), 4.62 (1H, d, J=15.6 Hz), 4.98 (1H, s), 6.58 (2H, d, J= 8.1 Hz), 7.05-7.65 (16H, m), 7.9 (2H, d, J=7.2 Hz). |
| 35 (2o) | 3400, 1733 | ($CDCl_3$): δ 4 (1H, d, J=15.6 Hz), 5.0 (1H, d, J=15.6 Hz), 5.38 (1H, s), 7.1-7.65 (17H, m), 8.5 (2H, d, J=7.2 Hz). |
| 30 (2p) | 3331, 1736 | ($CDCl_3$): δ 0.84 (3H, t, J=7.2 Hz), 3.89 (2H, dq, $J_1$=7.2 Hz, $J_2$=3 Hz), 4.73 (1H, s), 6.7-6.84 (2H, m), 6.89 (2H, t, J=9 Hz), 7.34-7.5 (3H, m), 7.55 (3H, t, J=7.5 Hz), 7.65 (2H, t, J=8.1 Hz), 7.83 (2H, dd, $J_1$=8.1 Hz, $J_2$=2.1 Hz), 8.1-8.22 (2H, m) |
| 36 (2q) | 3420, 1741 | (DMSO-$d_6$): δ 3.95 (1H, d, J=16.2 Hz), 4.6 (1H, d, J=16.2 Hz), 5.25 (1H, s), 6.1 (2H, d, J=7.8 Hz)), 6.9-7.3 (5H, m), 7.3-8.0 (15H, m). |
| 44 (2r) | 1734, 1653 | ($CDCl_3$): δ 2.05-2.25 (2H, m), 2.3-2.5 (2H, m), 3.55 (3H, s), 4.38 (2H, ddd, J1=4 Hz, J2=9 Hz, J3=25 Hz), 4.86 (1H, q, J=3.3), 7.1-7.6 (12H, m), 7.7-7.9 (4H, m). |
| 2s | 3350, 1704 | (DMSO-$d_6$): δ 3.47 (1H, d, J=15.6 Hz), 4.31 (1H, d, J=15.6 Hz), 5.8 (1H, s), 6.4-7.4 (20 H, m) |
| 46 (2t) | 3350, 1624 | ($CDCl_3$): δ 1.74 (3H, s), 3.67 (1H, d, J=15.3 Hz), 4.11 (1H, d, J=14.7 Hz), 4.38 (1H, s), 4.46 (1H, d, J=14.7 Hz) 4.59 (1H, d, J=15.3 Hz), 6.77 (2H, d, J=7 Hz), 7.0- 7.6 (13H, m) |
| 47 (3t) | 3350, 1738 | ($CDCl_3$): δ 1.14 (3H, s), 3.94 (1H, d, J=15.6 Hz), 4.24 (2H, q, J=8.7 Hz), 4.56 (1H, d, J=15 Hz), 5.74 (1H, s), 6.65 (2H, d, J=7.5 Hz), 7.0-7.4 (13H, m) |

*derivatives: k and 1 -ethyl esters; m-alcohol.

TABLE 7

| Compound | $^{13}$C NMR (75 MHz) |
|---|---|
| 33 (2a) | (DMSO-$d_6$): δ 25.2, 48.8, 70.4, 73.3, 122.3, 127.8, 128.3, 128.5, 128.9, 129.1, 129.3, 129.6, 129.7, 132.3, 133.2, 134, 166.1, 169.5 |
| 34 (2b) | ($CD_3OD$): δ 25.3, 48.8, 55.6, 70.9, 74.1, 115.2, 122.2, 123, 125.5, 127.9, 128.4, 129.2, 129.3, 129.6, 129.9, 132.8, 134.2, 161.1, 166.3, 168.4 |
| 28 (2c) | (DMSO-$d_6$): δ 25.2, 71.2, 77.9, 116.9, 117, 117.1, 117.3, 123, 125.1, 125.3, 129.3, 129.4, 129.6, 130.1, 130.3, 130.4, 130.5, 132.5, 133.3, 134.5, 160.4, 163.7, 165.3, 170.4 |
| 31 (2d) | (DMSO-$d_6$): δ 25.1, 49.1, 70.6, 71.7, 122.1, 123, 127.9, 128.4, 128.8, 129.2, 129.4, 132.8, 133.9, 141.4, 149.8, 166.5, 169.05 |
| 29 (2e) | ($CD_3OD$): δ 169.9, 166.2, 164.0, 162.1, 134.4, 131.5, 129.7, 129.6, 129.5, 129.3, 121.8, 116.9, 116.7, 75.1, 69.1, 62.9, 24.2, 12.8 |
| 40 (2g) | ($CD_3OD$): δ 24.23, 52.09, 70.83, 75.38, 121.84, 128.26, 128.69, 129.52, 129.75, 131.78, 134.02, 167.59, 168.62, 169.19 |
| 42 (2h) | ($CD_3OD$): δ 14.9, 25.6, 52.7, 56.7, 71.9, 72.5, 122.2, 128.8, 128.9, 129.6, 130.0, 134.5, 135.8, 169.2, 169.4, 170.4 |
| 41 (2i) | ($CD_3OD$): δ 13.3, 24.8, 30.6, 41.6, 61.0, 70.9, 73.5, 122.7, 128.9, 129.2, 129.8, 130.1, 132.7, 134.0, 167.3, 169.8, 170.9 |
| 37 (2j)* | ($CDCl_3$): δ 13.80, 27.13, 49.12, 60.06, 71.31, 127.98, 128.03, 128.12, 128.67, 129.02, 129.11, 130.96, 136.40, 136.80, 166.11, 171.78 |
| 38 (2k)* | ($CDCl_3$): δ 13.45, 27.13, 49.47, 60.83, 71.87, 77.94, 122.56, 127.79, 127.93, 128.55, 128.70, 130.21, 130.51, 135.82, 146.59, 149.75, 166.02, 171.37 |
| 45 (21)* | ($CDCl_3$): δ 17.25, 51.67, 61.54, 66.28, 66.93, 127.266, 127.68, 128.26, 128.56, 128.82, 129.06, 131.77, 135.48, 138.03, 139.90, 167.91 |
| 39 (2m) | (DMSO-$d_6$): δ 25.32, 55.66, 70.79, 72.57, 123.12, 128.24, 128.96, 129.42, 129.67, 130.12, 135.42, 136.24, 164.24, 170.77 |
| 32 (2n) | ($CDCl_3$): δ 29.7, 48.3, 75.6, 79.1, 123.1, 125.7, 126.7, 127.3, 127.4, 127.9, 128.1, 128.2, 128.8, 128.9, 129, 129.3, 132.9, 133.8, 136, 143.1, 164.8, 168.1 |
| 35 (2o) | ($CDCl_3$) δ 45.2, 66.3, 75.6, 123.7, 126.5, 126.9, 128.5, 128.6, 128.8, 129.2, 129.3, 131.9, 133.5, 134.4, 136.2, 143.4, 149.7, 166.6, 166.9 |
| 30 (2p) | ($CDCl_3$): δ 176.8, 169, 162.1, 155.7, 142.1, 142, 134.6, 133, 128.6, 128.2, 126.1, 125, 117.4, 117.3, 115.6, 115.3, 76.3, 66.1, 61.1, 13.3 |
| 36 (2q) | (DMSO-$d_6$): δ 169.6, 166, 136.5, 133.7, 132.5, 132.3, 129.7, 129.4, 128.9, 128.7, 128.6, 127.9, 127.8, 126.7, 126.6, 122.7, 121.4, 119, 111, 105.8, 74.4, 70.4, 48.5, 32.3 |
| 44 (2r) | ($CDCl_3$): δ 27.6, 30.1, 43.3, 51.6, 52.7, 127.1, 127.2, 127.3, 128.2, 128.3, 131.5, 131.6, 133.3, 137.8, 167.5, 171.4, 173.6 |

TABLE 7-continued

| Compound | $^{13}C$ NMR (75 MHz) |
|---|---|
| 2s | ($DMSO-d_6$): δ 30.7, 47.5, 72.1, 100.2, 126.2, 126.6, 126.8, 127.3, 127.7, 127.9, 128.0, 128.5, 128.6, 129.0, 131.4, 132.5, 133.4, 136.4, 164.4, 171.6 |
| 46 (2t) | ($CDCl_3$): δ 175.1, 164.8, 133.5, 132.8, 132.2, 129.7, 129.2, 129.1, 128.9, 128.6, 128.3, 127.6, 71.1, 70.6, 48.1, 32.4, 22.1 |
| 47 (3t) | ($DMSO-d_6$+ CD3OD): δ 170.6, 165.6, 134.2, 133.5, 132.2, 129.9, 129.8, 129.5, 129.4, 129.3, 129, 128.9, 128.7, 128.5, 128.3, 127.9, 73.5, 71.5, 48.6, 38.7, 27.1 |

*derivatives: k and 1 -ethyl esters; m-alcohol.

The general procedure for synthesizing the above compounds was as follows.

Synthesis of 2-oxazolin-5-ones was a follows. A solution of benzoyl amino acid (2 mmol.) and EDCI.HCl (2 mmol.) in dichloromethane (20 mL) was stirred at 0° C. for 1 hour for racemic compounds, 15 minutes for optically active compounds. The reaction mixture was washed successively with cold (containing ice) water, aqueous $NaHCO_3$, and water (10 mL each) The solution was dried over anhydrous magnesium sulfate, filtered, and the solvent evaporated to dryness in vacuo giving the oxazolones as solids or oils.

Synthesis of Imidazoline-4-carboxylic acids was as follows. A solution of aldehyde (1 mmol) and amine (1 mmol) in dry toluene/dry dichloromethane (10 mL) was refluxed under nitrogen for 2 hours. The solvent was evaporated under reduced pressure and the imine redissolved in dichloromethane (10 mL). To the solution was added oxazolone (1 mmol) and chlorotrimethylsilane (1.3 mmol) and the mixture was refluxed under nitrogen for 6 hours and then stirred overnight at room temperature. The product was either precipitated out from 1:1 dichloromethane/hexane or isolated after silica gel chromatography with 4:1 ethyl acetate/methanol.

Compound 33 (2a), dl-(4S,5S)-1-Benzyl-4-methyl-2,5-diphenyl-4,5-dihydro-1H-imidazole-4-carboxylic acid was syntesized as follows. A solution of benzaldehyde (0.06 g, 0.57 mmol), benzylamine (0.061 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (0.155 g, 74%).; HRMS (EI): calculated for $C_{24}H_{22}N_2O_2$ $[M-H]^+$ 369.1603, found $[M-H]^+$ 369.1610; M. P.: decomposes at 185-190° C.

Compound 34 (2b), dl-(4S,5S)-1-Benzyl-5-(4-methoxyphenyl)-4methyl-2-phenyl-4,5-dihydro-1H-imidazole-4-carboxylic acid was synthesized as follows. A solution of p-anisaldehyde (0.077 g, 0.57 mmol), benzylamine (0.061 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (0.180 g, 78%). HRMS (EI): calculated for $C_{25}H_{24}N_2O_3$ $[M-H]^+$ 397.1709, found $[M-H]^+$ 399.1717; M. P.: decomposes at 205-208° C.

Compound 28 (2c), dl-(4S,5S)-1-(4-Fluorophenyl)-4-methyl-2,5-diphenyl-4,5-dihydro-1H-imidazole-4-carboxylic acid was synthesized as follows. A solution of benzaldehyde (0.060 g, 0.57 mmol), 4-fluoroaniline (0.063 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (0.160 g, 74%). HRMS (EI): calculated for $C_{23}H_{19}FN_2O_2$ $[M-H]^+$ 373.1352, found $[M-H]^+$ 373.1359; M. P.: decomposes at 230-232° C.

Compound 31 (2d), dl-(4S,5S)-1-Benzyl-4-methyl-2-phenyl-5-pyridin-4yl-4,5-dihydro-1H-imidazole-4-carboxylic acid was synthesized as follows. A solution of pyridin-4-carboxylaldehyde (0.061 g, 0.57 mmol), benzylamine (0.061 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was isolated using 4:1 ethyl acetate/methanol as an off-white solid (0.161 g, 76%). HRMS (EI): calculated for $C_{23}H_{21}N_3O_2$ $[M-H]^+$ 370.1556, found $[M-H]^+$ 370.1556; M. P.: decomposes at 185-190° C.

Compound 29 (2e), dl-(4S,5S)-1-(4-Fluorophenyl)-4-methyl-2-phenyl-4,5-dihydro-1H-imidazole-4,5-dicarboxylic acid 5-ethyl ester was synthesized as follows. A solution of ethyl glyoxalate (0.058 g, 0.57 mmol) as 50% solution in toluene (1.03 g/mL), 4-fluoroaniline (0.063 g, 0.57 mmol) in dry dichloromethane (15 mL) was refluxed under nitrogen for 2 hours. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 hours and then stirred overnight at room temperature. The reaction mixture was evaporated to dryness under vacuum. The product was purified by silica-gel column chromatography using 4:1 ethyl acetate/methanol, to yield a white solid (0.152 g, 72%). HRMS (EI): calculated for $C_{20}H_{19}FN_2O_4$ $[M-H]^+$ 369.1251, and observed $[M-H]^+$ 369.1255; M. P.: decomposes at 190-193° C.

Compound 40 (2g), dl-(4S,5S)-1-Methoxycarbonylmethyl-4-methyl-2,5-diphenyl-4,5-dihydro-1H-imidazole-4-carboxylic acid was synthesized as follows. To a well stirred solution of 2-Phenyl-4-methyl-4H-oxazolin-5-one (0.5 g, 2.85 mmol) and TMSCl (0.37 g, 3.42 mmol) in dry dichloromethane (50 ml) added a solution of (benzylidene-amino)-acetic acid methyl ester (0. gm, mmol) in dry methylene chloride (20 ml) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (0.70 g, 70%). MS (EI): calculated for $C_{20}H_{20}N_2O_4$ (m/z) 352.14 observed m/z 353.2; M. P.: decomposes at 215-217° C.

Compound 42 (2h), dl-(4S,5S)-1-(1-Methoxycarbonyl-ethyl)-4-methyl-2,5-diphenyl-4,5-dihydro-1H-imidazole-4-carboxylic acid was synthesized as follows. To a well stirred solution of 2-Phenyl-4-methyl-4H-oxazolin-5-one (0.25 g, 1.5 mmol) and TMSCl (0.23 ml, 1.8 mmol) in dry dichloromethane (50 ml) added a solution of 2-(Benzylidene-amino)-propionic acid methyl ester (0.34 gm, 1.8 mmol) in dry methylene chloride (20 ml) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (0.340 g, 66%). MS (EI): calculated for $C_{21}H_{22}N_2O_4$ (m/z) 366.4 observed m/z=366.6. M.P.: decomposes at 222-226° C.

Compound 41 (2i), dl-(4S,5S)-1-(2-Ethoxycarbonyl-ethyl)-4-methyl-2,5-diphenyl-4,5-dihydro-1H-imidazole-4-carboxylic acid was synthesized as follows. To a well stirred solution of 2-Phenyl-4-dimethyl-4H-oxazolin-5-one (1.0 g, 5.7 mmol) and TMSCl (1 ml, 6.8 mmol) in dry dichloromethane (80 ml) added a solution of 3-(benzylidene-amino)-propionic acid ethyl ester (1.4 gm, 6.8 mmol) in dry methylene chloride (60 ml) and the mixture was refluxed under nitrogen for 10 hours and then stirred overnight at room temperature. The reaction mixture was evaporated to dryness under vacuum. The product was precipitated out as a white solid using a 1:1 dichloromethane/hexanes mixture (1.08 g, 51.4%). MS (EI): calculated for $C_{22}H_{24}N_2O_4$ (m/z) 380.44 observed m/z=380.7. M.P.: decomposes at 218-220° C.

Compound 37 (2j), dl-(4S,5S)-1-Benzyl-4-methyl-2,5-diphenyl-4,5-dihydro-1H-imidazole-4-carboxylic acid ethyl ester was synthesized as follows. To a well-stirred suspension of imidazoline-4-carboxylic acid 2a (0.1 g, 0.27 mmol) in dry methylene chloride (30 mL) at 0° C. added a solution of oxallyl chloride (0.14 g, 1.1 mmol) in dry dichloromethane (5 mL). A solution of DMF (0.001 mL) in dry dichloromethane (1 mL) was added to the reaction mixture and was stirred at 0° C. for another 2 hours. The dichloromethane was evaporated under vacuum and the reaction mixture cooled to 0° C. after which absolute ethanol (20 mL) was added. The solution was allowed to stir for an additional 1 hour. The solvent was evaporated under vacuum and the reaction mixture diluted with dichloromethane (30 mL) and washed with saturated sodium bicarbonate (10 mL) and water (10 mL). The organic layer was dried over sodium sulfate and was concentrated under vacuum to yield crude product, which was further purified by silica-gel column chromatography using ethyl acetate, to yield colorless oil (0.095 gm, 89%). MS (EI): calculated for $C_{26}H_{26}N_2O_2$ (m/z) 398.2 observed m/z=398.9.

Compound 38 (2k), dl-(4S,5S)-1-Benzyl-4-methyl-2-phenyl-5-pyridin-4-yl-4,5-dihydro-1H-imidazole-4-carboxylic acid ethyl ester was synthesized as follows. To a well-stirred suspension of dl-(3S,4S)-1-benzyl-4-methyl-2-phenyl-5-pyridin-4yl-4,5-dihydro-1H-imidazole-4-carboxylic acid 2d (0.1 g, 0.27 mmol) in dry dichloromethane (30 mL) at 0° C. added a solution of oxallyl chloride (0.14 g, 1.1 mmol) in dry dichloromethane (5 mL). A solution of DMF (0.001 mL) in dry dichloromethane (1 mL) was added to the reaction mixture and was stirred at 0° C. for another 2 hours. The dichloromethane was evaporated under vacuum and the reaction mixture cooled to 0° C. after which absolute ethanol (20 mL) was added. The solution was allowed to stir for an additional 1 hour. The solvent was evaporated under vacuum and the reaction mixture diluted with dichloromethane (30 mL) and washed with saturated sodium bicarbonate (10 mL) and water (10 mL). The organic layer was dried over sodium sulfate and was concentrated under vacuum to yield crude product, which was further purified by silica-gel column chromatography using ethyl acetate, to yield a pale yellow oil (0.097 gm, 91%). MS (EI): calculated for $C_{25}H_{26}N_2O_2$ (m/z) 399.19 observed m/z: 399.3.

Compound 45 (2l), dl-(4S,5S)-1-Benzyl-4-methyl-2,5-diphenyl-4,5-dihydro-1H-imidazol-4-yl)-methanol was synthesized as follows. To a well stirred suspension of Lithium aluminum hydride (0.12 gm, 0.3 mmol) in dry THF (5 ml) added a solution of 1-benzyl-4-methyll-2,5-diphenyl-4,5-ihydro-1H-imidazole-4-carboxylic acid (0.1 gm, 0.27 mmol) in dry THF (5 ml) at 0° C. drop wise, stirred at same temperature for 15 minutes quenched with ice cold saturated ammonium chloride solution [Caution: Ammonium chloride solution kept at 0° C. for about 30 minutes; and should be added with extreme care; highly exothermic reaction and the reaction mixture should be at 0° C.] then added about 10 ml of 10% HCl. The reaction mixture diluted with excess of ethyl acetate (100 ml) washed with water (20 ml) dried over anhydrous sodium sulfate, filtered through a fluted filter paper and the organic layer evaporated under reduced pressure to yield the crude product which was purified by column chromatography using ethyl acetate. yield: 79%; viscous oil, m/z: 357.2.

Compound 39 (2m), dl-(4S,5S)-4-Methyl-2,5-diphenyl-4,5-dihydro-1H-imidazole-4-carboxylic acid was synthesized as follows. To a well-stirred suspension of imidazoline-4-carboxylic acid 2a (0.1 g, 0.27 mmol) and cyclohexene (0.1 mL, 1.25 mmol) in dry THF (30 mL) was added 10% Pd/C (45 mg, 0.06 mmol). The suspension was refluxed for 36 hours. The reaction mixture cooled to room temperature and ethanol (10 mL) was added. The mixture was filtered through a Celite bed, washed with ethanol and the filtrate was evaporated under reduced pressure. The crude product was purified by column silica-gel chromatography using ethanol, to yield a white solid (0.070 g, 93%). MS (EI): calculated for $C_{17}H_{16}N_2O_2$ (m/z) 280.12 observed m/z: 280.1; M. P.: decomposes at 222-224° C.

Compound 32 (2n), dl-(4S,5S)-1-Benzyl-2,4,5-triphenyl-4,5-dihydro-1H-imidazole-4-carboxylic acid was synthesized as follows. A solution of benzaldehyde (0.6 g, 5.7 mmol), benzylamine (0.61 g, 5.7 mmol) in dry dichloromethane (120 mL) was refluxed under nitrogen for 2 hours. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 hours and then stirred overnight at room temperature. The product was purify by silica-gel column chromatography with 1:5 ethanol/ethyl acetate to afford 2.1 g of the product in 65% yield as an off-white solid. HRMS (EI): calculated for $C_{29}H_{24}N_2O_2$ [(M−H)—$CO_2$]$^+$387.1526 and observed [(M−H)—$CO_2$]$^+$387.1539; M. P.: decomposes at 153-155° C.

Compound 35 (2o), dl-(4S,5S)-1-Benzyl-2,4-diphenyl-5-pyridin-4-yl-4,5-dihydro-1H-imidazole-4-carboxylic acid was synthesized as follows. A solution of pyridin-4-carboxylaldehyde (0.61 g, 0.57 mmol), benzylamine (0.61 g, 5.7 mmol) in dry dichloromethane (120 mL) was refluxed under nitrogen for 2 hours. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 hours and then stirred overnight at room temperature. The product was purified by precipitation from dichloromethane/ether mixture to afford 1.35 g of the product in 55% yield as an off-white solid. MS (EI): calculated for $C_{24}H_{22}N_2O_2$ (m/z) 434.34, found (m/z) 434.2

Compound 30 (2p), dl-(4S,5S)-1-(4-Fluorophenyl)-2,4-diphenyl-4,5-dihydro-1H-imidazole-4,5-dicarboxylic acid 5-ethyl ester was synthesized as follows. A solution of ethyl glyoxalate (0.85 g, 8.3 mmol) as 50% solution in toluene (1.03 g/mL), 4-fluoroaniline (0.93 g, 8.3 mmol) in dry dichloromethane (250 mL) was refluxed under nitrogen for 2 hours. 2,4-diphenyl-4H-oxazolin-5-one (2 g, 8.3 mmol) and chlorotrimethylsilane (1.16, 10.8 mmol) were added and the mixture was refluxed under nitrogen for 6 hours and then stirred overnight at room temperature. The reaction mixture was evaporated to dryness under vacuum. The product was purified by precipatation with dichloromethane/ether to yield a white solid (2.4 g, 68%). MS (EI): calculated for $C_{25}H_{21}FN_2O_4$ $[M]^+$432.15, and observed $[M]^+$ 432.4;

Compound 36 (2q), dl-(4S,5S)-1-Benzyl-4-(1H-indol-3-ylmethyl)-2,5-diphenyl-4,5-dihydro-1H-imidazole-4-carboxylic acid was synthesized as follows. A solution of benzaldehyde (0.6 g, 5.7 mmol), benzylamine (0.61 g, 5.7 mmol) in dry dichloromethane (120 mL) was refluxed under nitrogen for 2 hours. 4-(1H-Indol-3-ylmethyl)-2-phenyl-4H-oxazol-5-one (1.65 g, 5.7 mmol) and chlorotrimethylsilane (0.8 g, 7.4 mmol) were added and the mixture was refluxed under nitrogen for 6 hours and then stirred overnight at room temperature. The product was purified by silica-gel column chromatography with 1:5 ethanol/ethyl acetate to afford 3.1 g of product in 68% yield as an off-white solid. HRMS (EI): calculated for $C_{32}H_{27}N_3O_2$ $[M-H]^+$ 484.2025 and observed $[M-]^+$ 484.2011; M.P.: decomposes at >250° C.

Compound 44 (2r), dl-(4S,5S)-1-Benzyl-4-(2-methoxy-carbonyl-ethyl)-2,5-diphenyl-4,5-dihydro-1H-imidazole-4-carboxylic acid was synthesized as follows. A solution of benzaldehyde (0.252 g, 2.4 mmol), benzylamine (0.258 g, 2.4 mmol) in dry dichloromethane (100 mL) was refluxed under nitrogen for 2 hours. 3-(5-Oxo-2-phenyl-4,5-dihydro-oxazol-4-yl)-propionic acid methyl ester SP-1-182 (1e) (0.5 g, 2 mmol) and chlorotrimethylsilane (0.282 g, 2.6 mmol) were added and the mixture was refluxed under nitrogen for 6 hours and then stirred overnight at room temperature. The reaction mixture was evaporated to dryness under vacuum. The product was precipitated out as a white solid using a 1:1 dichloromethane/hexanes mixture (0.54 g, 60%). MS (EI): calculated for $C_{24}H_{22}N_2O_2$ (m/z) 442.5, found (m/z) 442.2.

Compound 2s, dl-(4S,5S)-1,2-dibenzyl-4,5-diphenyl-4,5-dihydro-1H-imidazole-4-carboxylic acid was synthesized as follows. A solution of benzaldehyde (0.6 g, 5.7 mmol), benzylamine (0.61 g, 5.7 mmol) in dry dichloromethane (120 mL) was refluxed under nitrogen for 2 hours. 2-benzyl-4-phenyl-4H-oxazolin-5-one (1.43 g, 5.7 mmol) and chlorotrimethylsilane (0.8 g, 7.4 mmol) were added and the mixture was refluxed under nitrogen for 6 hours and then stirred overnight at room temperature. The product was a mixture of diastereomers (3:1 ratio) and was obtained in 60% yield. The above trans-diastereomer was obtained by repeated precipitation from methanol/ether. HRMS (EI): calculated for $C_{30}H_{26}N_2O_2$ $[(M-H)—CO_2]^+$ 402.5 and observed $[(M-H)—CO_2]^+$ 402.1.

Compound 46 (2t), dl-(4S,5S)-1,2-Dibenzyl-4-methyl-5-phenyl-4,5-dihydro-1H-imidazole-4-carboxylic acid, and Compound 47 (3t), dl-(4S,5R)-1,2-Dibenzyl-4-methyl-5-phenyl-4,5-dihydro-1H-imidazole-4-carboxylic acid were synthesized as follows. A solution of benzaldehyde (1.13 g, 10.58 mmol), benzylamine (1.13 g, 10.58 mmol) in dry dichloromethane (250 mL) was refluxed under nitrogen for 2 hours. 2-benzyl-4-methyl-4H-oxazolin-5-one (2 g, 10.58 mmol) and chlorotrimethylsilane (1.48 g, 10.58 mmol) were added and the mixture was refluxed under nitrogen for 6 hours and then stirred overnight at room temperature. The reaction mixture was evaporated to dryness under vacuum. The product, that precipitated out as a white solid using a dichloromethane/ether mixture (0.6 g, 30%), was found to be the cis-isomer (3t). The trans-isomer (2t) then precipitated out from the mother liquor. A small amount was then reprecipitated to remove traces of (3) (0.15 g, 7%) and for characterization.

The compounds and method for synthesis are summarized in Tables 8 and 9.

TABLE 8

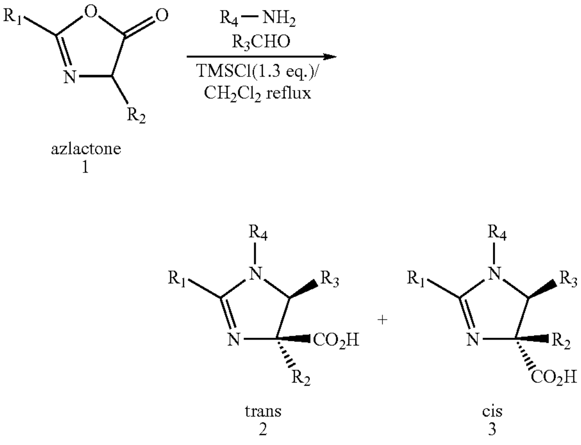

azlactone 1
trans 2
cis 3

| | $R_1$ | $R_2$ | $R_3$ | $R_4$ | % Yield 1 | Ratio 2:3 | % Yield 2 |
|---|---|---|---|---|---|---|---|
| a | Ph | Me | Ph | Bn | 75 | >95:5 | 74 |
| b | Ph | Me | 4-methoxy-phenyl | Bn | 75 | >95:5 | 78 |
| c | Ph | Me | Ph | 4-fluorophenyl | 75 | >95:5 | 74 |
| d | Ph | Me | 4-pyridinyl | Bn | 75 | >95:5 | 76 |
| e | Ph | Me | $—CO_2Et$ | 4-fluorophenyl | 75 | >95:5 | 72 |
| f | Ph | Me | Ph | benzhydryl | 75 | >95:5 | 0 |
| g | Ph | Me | Ph | $—CH_2CO_2Me$ | 75 | >95:5 | 70 |
| h | Ph | Me | Ph | $—CH(CH_3)CO_2Me$ | 75 | >95:5 | 66 |
| i | Ph | Me | Ph | $—CH_2CH_2CO_2Et$ | 75 | 75:25 | 51 |
| j* | Ph | Me | Ph | Bn | 75 | ethyl ester | 75 |
| k* | Ph | Me | 4-pyridinyl | Bn | 75 | ethyl ester | 76 |
| l* | Ph | Me | Ph | Bn | 75 | alcohol | 79 |
| m* | Ph | Me | Ph | H | 75 | >95:5 | 71 |

*derivatives: k and l -ethyl esters; l-alcohol.

TABLE 9

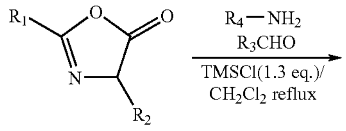

azlactone
1

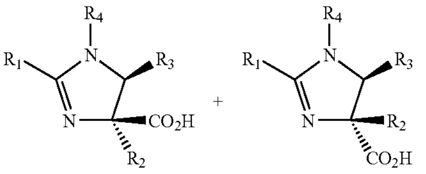

trans
2 cis
3

| | $R_1$ | $R_2$ | $R_3$ | $R_4$ | % Yield 1 | Ratio 2:3 | % Yield* 2 |
|---|---|---|---|---|---|---|---|
| a | Ph | Me | Ph | Bn | 75 | >95:5 | 74 |
| n | Ph | Ph | Ph | Bn | 70 | >95:5 | 65 |
| o | Ph | Ph | 4-pyridinyl | Bn | 75 | >95:5 | 55 |
| p | Ph | Ph | —$CO_2$Et | 4-fluorophenyl | 75 | >95:5 | 68 |
| q | Ph | indolyl-3-methyl | Ph | Bn | 80 | >95:5 | 68 |
| r | Ph | —$CH_2CH_2CO_2$Me | Ph | Bn | 69 | >95:5 | 60 |
| s | Bn | Ph | Ph | Bn | 90 | 75:25 | 45 |
| t | Bn | Me | Ph | Bn | 76 | 67:33 | N.O. |
| u | Me | Me | Ph | Bn | 60 | 50:50 | N.O. |

N.O.—not optimized

EXAMPLE 26

Figure 7:
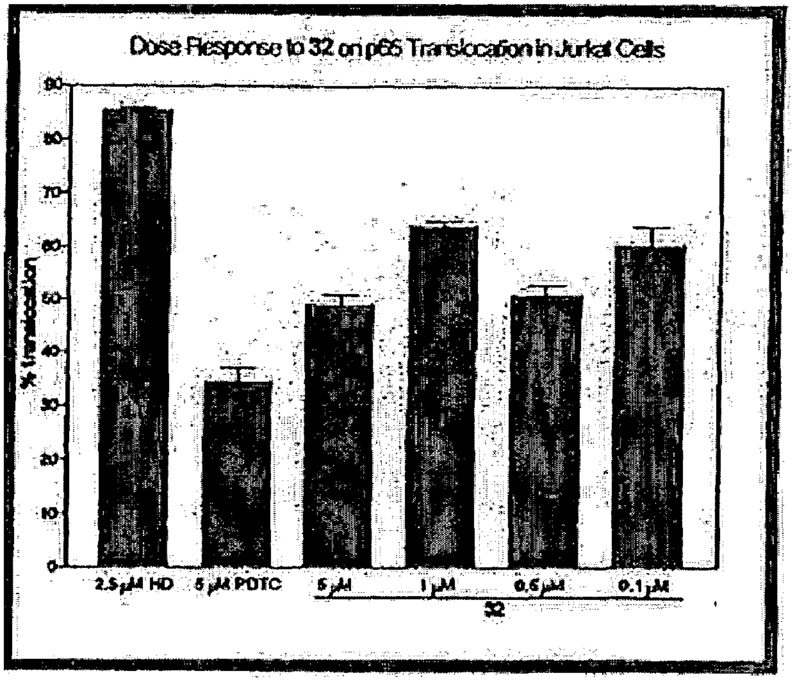
FIG. 7 shows the inhibition of nuclear translocation of NF-κB by compound 32 as measured by a p65 ELISA.
Figure 8:
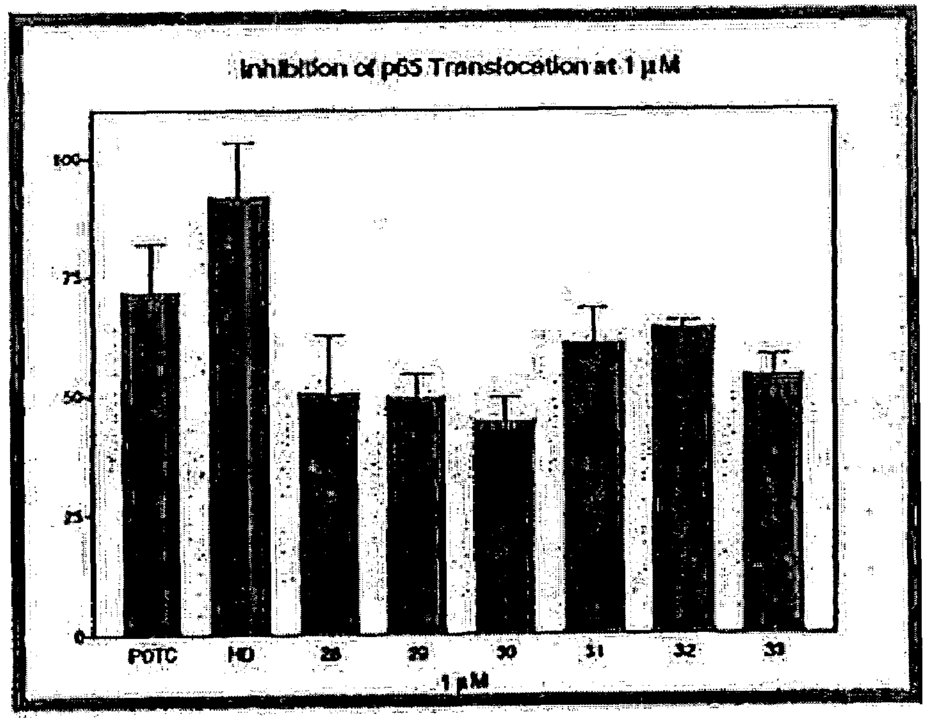
FIG. 8 shows the inhibition of nuclear translocation of NF-κB by compounds 28-33 as measured by a p65 ELISA.

The ability of the imidazolines in FIG. 5 to inhibit the nuclear translocation of NF-κB is described. Inhibition of the nuclear translocation of the p50/p65 heterodimer of NF-κB was confirmed by a p65-ELISA assay. Cells were treated with the PDTC (positive control-reported to inhibit IκB phosphorylation thus inhibiting NF-κB translocation), and imidazoline 32, 30 minutes prior to PMA activation, followed by the isolation of the nuclear extract after a 30 minute incubation period. PDTC and the imidazolines, but not hymenialdisine (negative control-inhibits NF-κB-DNA binding, but not nuclear translocation) indicated significant inhibition of NF-κB p50/p65 heterodimer translocation at concentrations ranging from 100 ηM-5.0 μM (FIG. 7, for a representative titration of imidazoline 32). These results, therefore, indicate that the imidazoline 32 significantly inhibits NF-κB translocation at submicromolar concentrations, and were even found to be more active than PDTC. Similar results were obtained for compounds 28-33 (FIG. 8).

Figure 9:
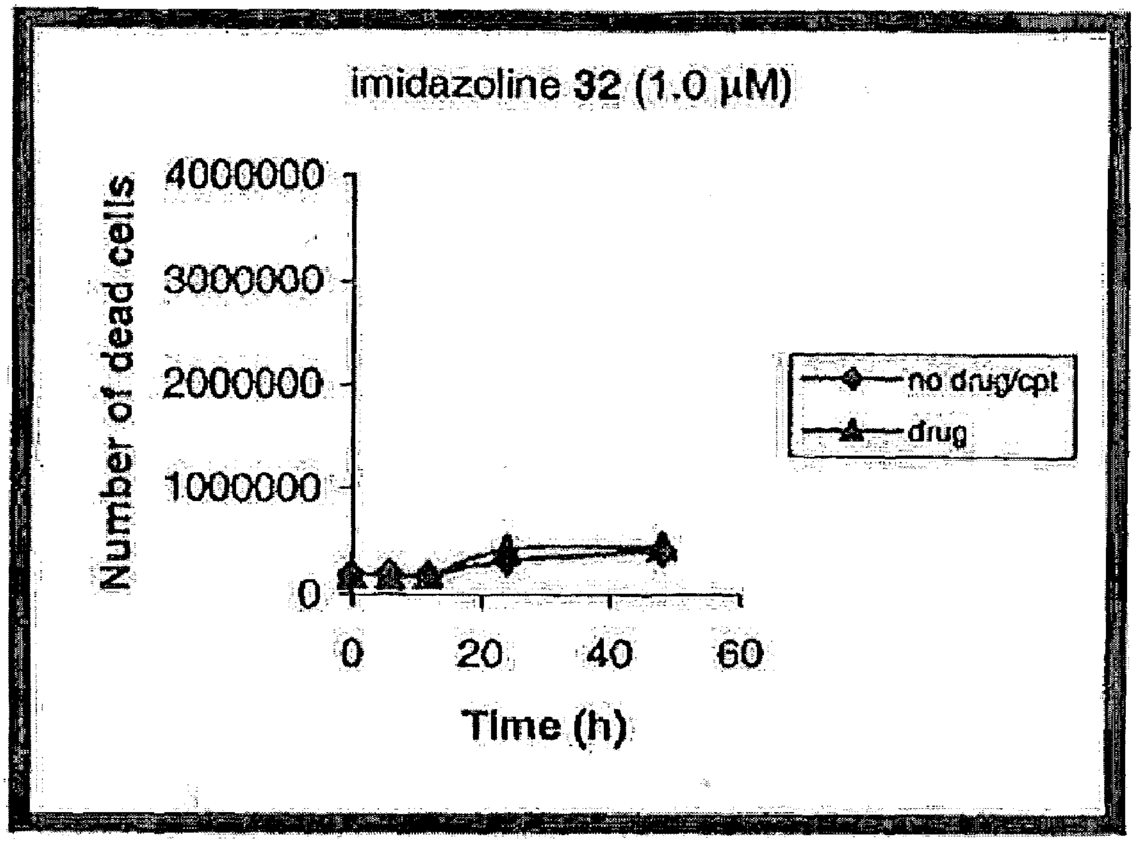
FIG. 9 shows that cell death over time in response to compound 32 is insignificant.

Compounds 28-33 were evaluated for their toxicity in T-cells and were found to exhibit no significant toxicity. Cell death was measured over a 48 hour period and the results shown in Table 10 and a representative graph of the "most toxic" inhibitor 32 is shown on FIG. 9.

TABLE 10

| Compound (1.0 μm) | Apoptosis (±S.D.) |
|---|---|
| Cells only | 1.00 (normalized) |
| 28 | 1.25 ± 0.18 |
| 29 | 0.95 ± 0.24 |
| 30 | 1.18 ± 0.20 |

TABLE 10-continued

| Compound (1.0 μm) | Apoptosis (±S.D.) |
|---|---|
| 31 | 1.18 ± 0.00[b] |
| 32 | 1.98 ± 0.0001 |

Figure 10A:
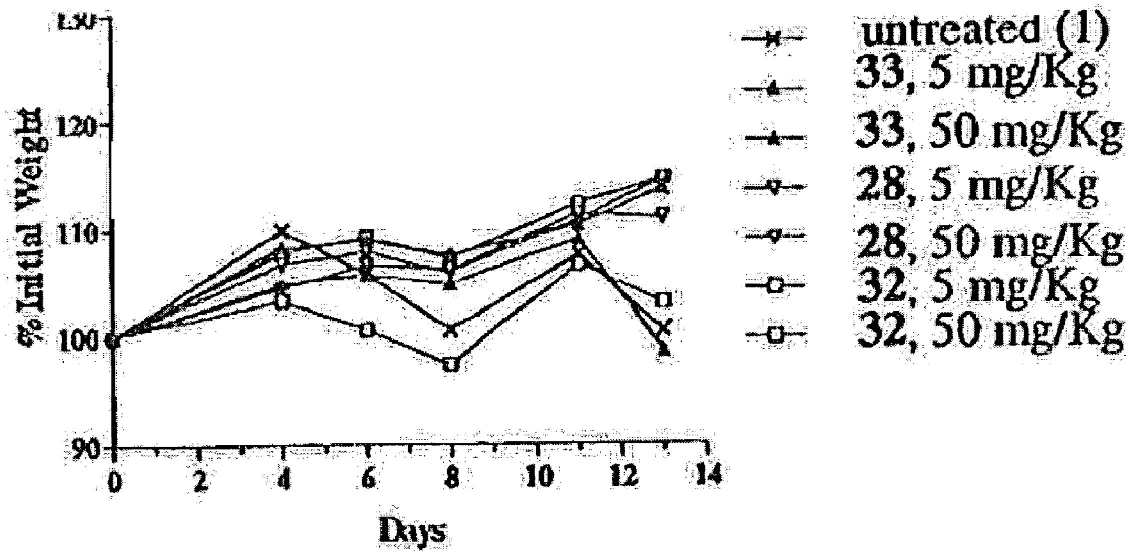
FIG. 10A shows compounds 28, 32, and 33 are not toxic to mice.
Figure 10B:
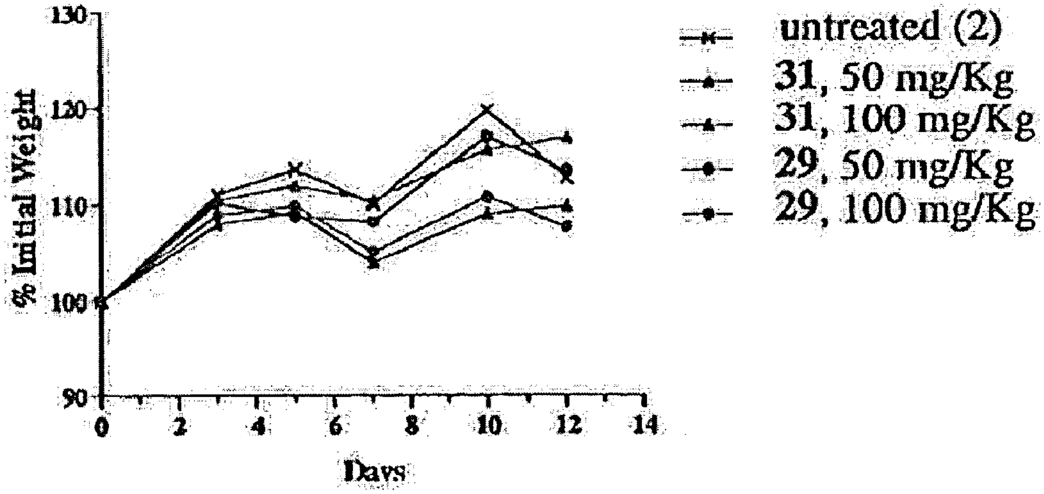
FIG. 10B shows compounds 29 and 31 are not toxic to mice.

Prior to the combinatorial studies, the toxicity of the compounds was determined in the mouse model. Compounds 28-33 showed no apparent toxicity to the mice at concentrations up to 100 mg/kg. In short, the drugs are dissolved in DMSO and 100 μL given to the mice on day 0 by intraperitoneal injection (IP). Initially, doses (5.0 and 50 mg/kg of compounds 28, 32, and 33) were used. Since these were well tolerated (FIG. 6A), compounds (29 and 31) were used at 50 and 100 mg/kg (FIG. 10B). If weight did not drop at least 10% from the initial weight, then the toxicity was not considered significant. Weight and death were the two measures of toxicity. No toxicity was observed in these models during a two-week period. Compound 30 was also found to be non-toxic in the same type of experiment.

The results show that these novel imidazolines are potent inhibitors of the transcription factor NF-κB and were found to be non-toxic in T-cells and animal models. The combination of a non-toxic potent NF-κB inhibitor is useful in the treatment of NF-κB regulated diseases and disorders such as inflammatory diseases, certain viral infections, autoimmune diseases, and inhibiting rejection of organ and tissue transplants.

EXAMPLE 27

This example shows the inhibitory effects of imidazolines 28-33 on NF-kB activation and its ability to cehmopotentiate cis-platin.

Camptothecin (CPT) is an alkaloid isolated from the extracts of the fruit of *Camptotheca acuminata* Decaisne and was found to be a topoisomerase inhibitor (Denny, ACS Press: Washington, D.C., 483-500 (1995)). Currently, CPT-11 and several water soluble analogues including topotecan have successfully past clinical trials in the United States (Wall, Med. Res. Rev. 18: 299-314 (1998)). Camptothecin exhibits its antitumor activity via the formation of a stable ternary topoisomerase I-DNA cleavable complex. Stabilization of this cleaved DNA complex initiates a signaling pathway, ultimately resulting in apoptotic cell death (Pommier et al., Biochim. Biophys. Acta 1400: 83-105 (1998); Macdonald et al., Comprehensive natural products chemistry; Elsevier-North Holland: Amsterdam, pp 593-614 (1999)).

Figure 11:
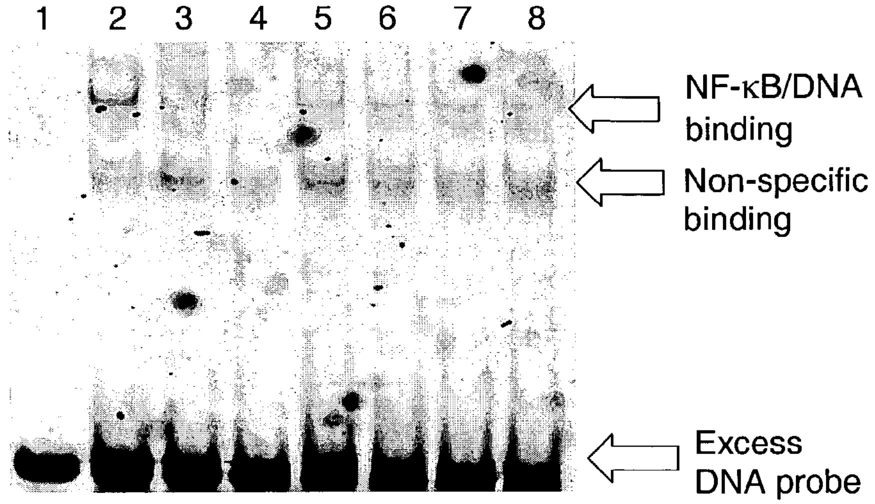
FIG. 11 shows an EMSA assay for NF-κB activation by camptothecin. Lane 1: NF-κB consensus oligonucleotide (0.16 pmol/λ); Lane 2: NF-κB consensus oligo (0.16 pmol/λ)+Nuclear extract (PMA/PHA, 20 μg); Lane 3: NF-κB consensus oligo (0.16 pmol/λ)+Nuclear extract (PMA/PHA, 20 μg)+Antibody p65; Lane 4: NF-κB consensus oligo (0.16 pmol/λ)+Nuclear extract (-PMA/-PHA, 20 μg); Lane 5: NF-κB consensus oligo (0.16 pmol/λ)+Nuclear extract (10 μM CPT, 20 μg); Lane 6: NF-κB consensus oligo (0.16 pmol/λ)+Nuclear extract (1 μM CPT, 20 μg); Lane 7: NF-κB consensus oligo (0.16 μmol/λ)+Nuclear extract (0.1 μM CPT, 20 μg); Lane 8: NF-κB consensus oligo (0.16 pmol/λ)+Nuclear extract (0.01 μM CPT, 20 μg). All incubations with CPT were performed for 2 hours. The positive control with PMA/PHA was incubated for 4 hours.

In addition to the stabilization of the topoisomerase I-DNA cleavable complex, camptothecin also activates DNA repair mechanism mediated by the nuclear transcription factor NF-κB (Boland, Biochem Soc Trans 29: 674-678 (2001); Bottero et al., Cancer Res 61: 7785-7791 (2001); Huanget al., J Biol Chem 275: 9501-9509 (2000); Piret and Piette, Nucl. Acids Res. 24: 4242-4248 (1996)). Activation of NF-κB by DNA damaging agents such as the camptothecin (CPT) has been documented in different cell lines by several groups (Bottero et al., Cancer Res 61: 7785-7791 (2001); Huanget al., J Biol Chem 275: 9501-9509 (2000); Piret and Piette, Nucl. Acids Res. 24: 4242-4248 (1996)). CEM leukemia T-cells were demonstrated to be sensitive to NF-κB activation by camptothecin and these results were confirmed in our laboratory using an EMSA assay (FIG. 3) (Piret and Piette, Nucl. Acids Res. 24: 4242-4248 (1996)). CEM cells were incubated with and without varying concentrations of camptothecin (CPT). Positive controls included PMA/PHA activation (FIG. 11, lane 2). Lane 3 included a positive control using PMA/PHA activation followed by the treatment of the extract with a NF-κB p65 antibody to unambiguously identify the NF-κB/DNA complex.

As anticipated, treatment of the nuclear extract with the p65 antibody resulted in a significant decrease in NF-κB/DNA binding (lane 3). As a negative control, cells were left unactivated and nuclear extracts were treated with the NF-κB consensus sequence, illustrating only a slight background level of NF-κB (lane 4). Treatment of the CEM cells with camptothecin concentrations ranging from 10 μM to 10 nM (FIG. 11, lanes 5-8) illustrated a significant amount of NF-κB/DNA binding due to NF-κB activation.

Inhibition of camptothecin mediated activation of NF-κB by imidazolines is as follows. Induction of NF-κB activation can proceed via a wide range of signaling pathways (Delhase et al., Science 284: 309-313 (1999); Karin, Oncogene 18: 6867-6874 (1999)). Inhibition of NF-κB activation can proceed via the inhibition of many different pathways (Epinat and Gilmore, Oncogene 18: 6896-6909 (1999)). Modulators of these pathways may be therefore act as general activation inhibitors, whereas others may inhibited specific induction pathways (Epinat and Gilmore, Oncogene 18: 6896-6909 (1999)). In order to investigate whether the imidazolines inhibit the specific pathway of camptothecin induced NF-κB activation, we examined the inhibition of camptothecin induced NF-κB nuclear binding in the presence of the imidazolines.

Figure 12:
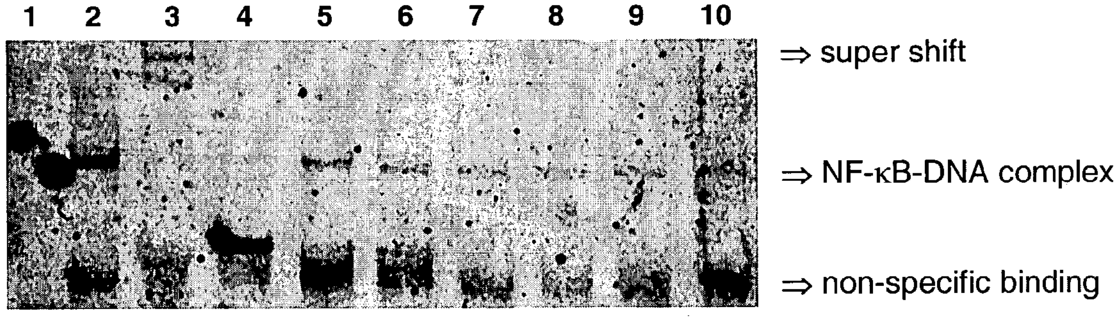
FIG. 12 shows an EMSA assay for inhibition of CPT activated NF-κB by imidazoline 32. Lane 1: NF-κB consensus oligonucleotide (0.16 pmol/λ); Lane 2: NF-κB consensus oligo (0.16 pmol/λ)+nuclear extract (PMA/PHA); Lane 3: NF-κB consensus oligo (0.16 pmol/λ)+nuclear extract (PMA/PHA)+Antibody p65; Lane 4: NF-κB consensus oligo (0.16 pmol/λ)+nuclear extract (-PMA/-PHA); Lane 5: NF-κB consensus oligo (0.16 pmol/λ)+nuclear extract (0.1 μM CPT); Lane 6: NF-κB consensus oligo (0.16 pmol/λ)+nuclear extract (0.1 μM CPT+5 μM PDTC); Lane 7: NF-κB consensus oligo (0.16 pmol/λ)+nuclear extract (0.1 μM CPT+10 μM 32); Lane 8: NF-κB consensus oligo (0.16 pmol/λ)+nuclear extract (0.1 μM CPT+1 μM 32); Lane 9: NF-κB consensus oligo (0.16 pmol/λ)+nuclear extract (0.1 μM CPT+0.1 μM 32); Lane 10: NF-κB consensus oligo (0.16 pmol/λ)+nuclear extract (0.1 μM CPT+0.01 μM 32). All incubations with CPT were performed for 2 hours. The positive control with PMA/PHA was incubated for 4 hours.
Figure 13A:
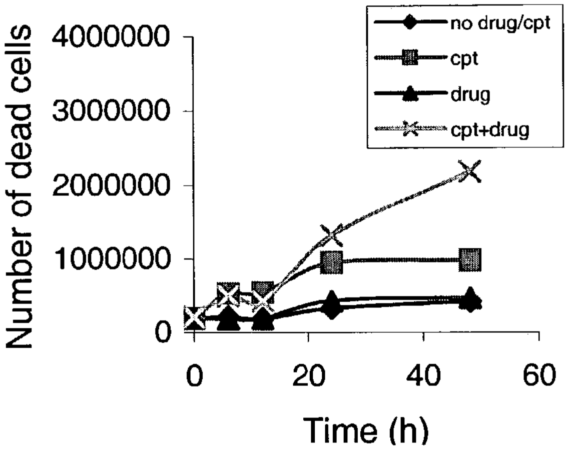
FIG. 13A shows the sensitization of CEM cells towards camptothecin by 1 μM imidazoline 31.
Figure 13B:
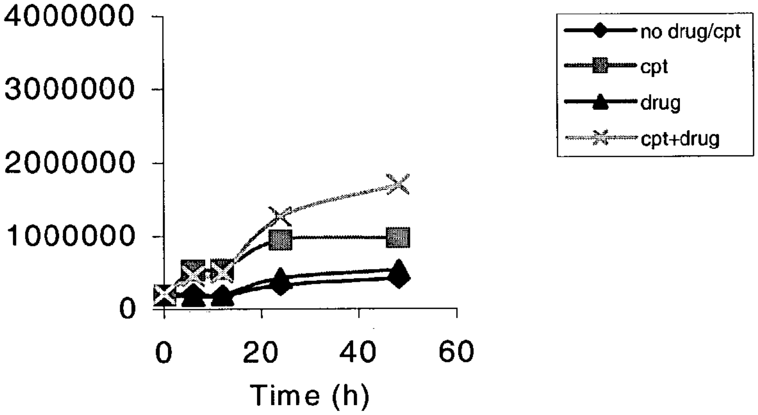
FIG. 13B shows the sensitization of CEM cells towards camptothecin by 0.1 μM imidazoline 31.
Figure 13C:
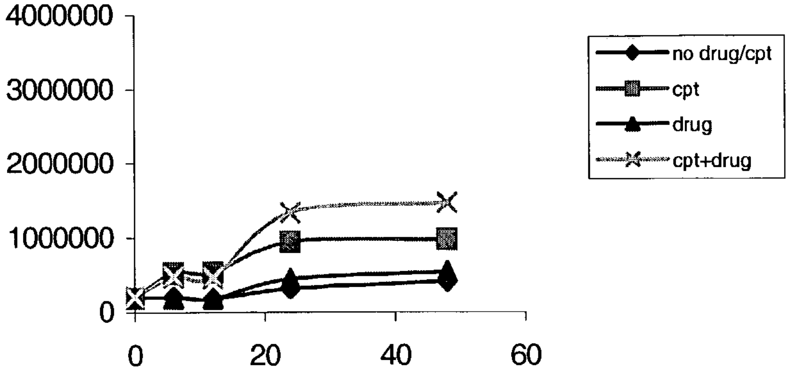
FIG. 13C shows the sensitization of CEM cells towards camptothecin by 0.01 μM imadizoline 31.
Figure 13D:
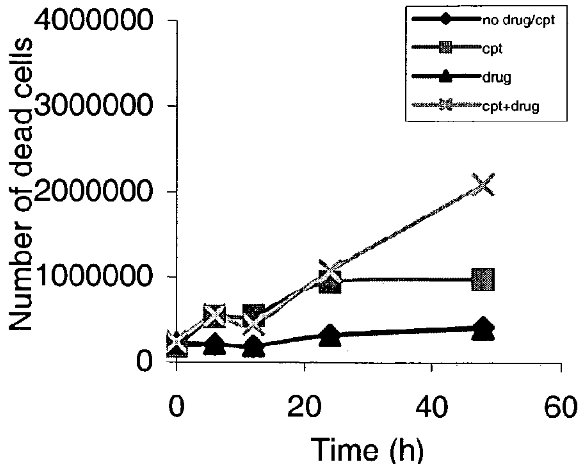
FIG. 13D shows the sensitization of CEM cells towards camptothecin by 1 μM imidazoline 30.
Figure 13E:
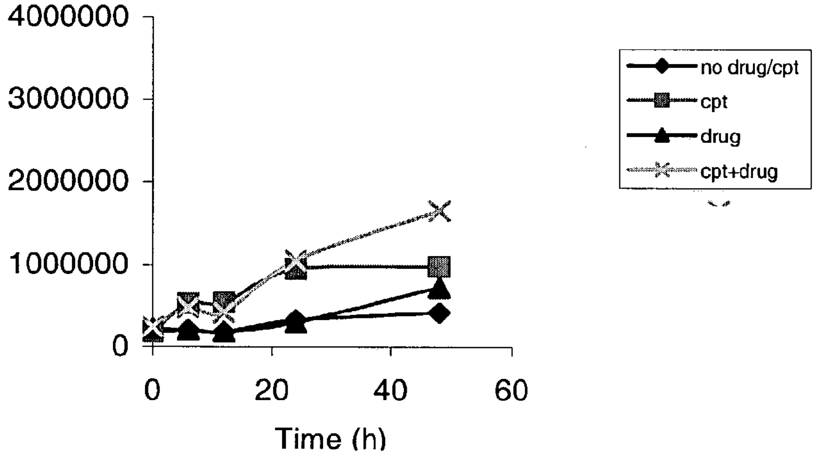
FIG. 13E shows the sensitization of CEM cells towards camptothecin by 0.1 μM imidazoline 30.
Figure 13F:
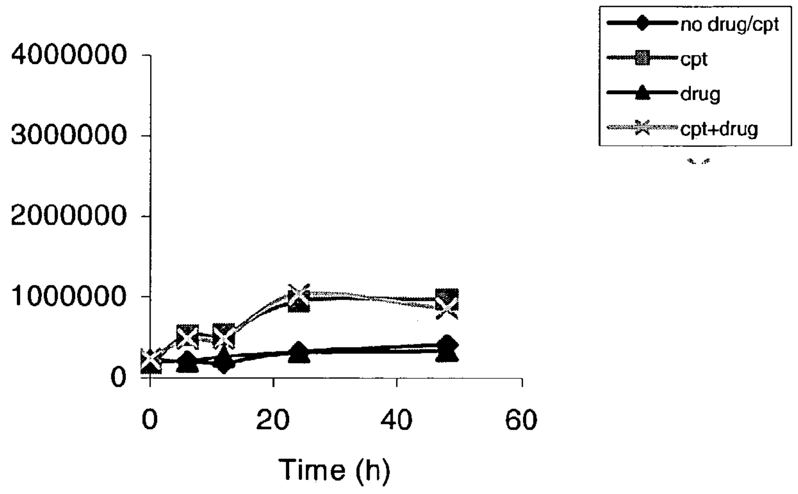
FIG. 13F shows the sensitization of CEM cells towards camptothecin by 0.01 μM imidazoline 30.

CEM cells were treated with various concentration of imidazoline 32, 30 minutes prior to activation by camptothecin (0.1 μM). As illustrated in FIG. 12, the addition of imidazoline 32 inhibited camptothecin induced NF-κB nuclear binding in a dose responds manner. Control lanes include: DNA only (lane 1), PMA/PHA activated NF-κB (lane 2), PMA/PHA activated NF-κB treated with a p65 antibody, which provide a supershift (lane 3) and the unactivated control (lane 4). Activation of NF-κB with camptothecin provide a strong band indicative of the NF-κB-DNA complex (lane 5). Inhibition of DNA binding in the presence of the non-selective NF-κB inhibitor PDTC resulted in a decrease of binding (lane 6). A similar decrease of camptothecin induced DNA binding is clearly illustrated in lanes 7-10, upon treatment of imidazoline 32 ranging from 10 μM to 10 nM concentration. Comparison of lane 5 (activated by 0.1 μM CPT) with lane 7 (activated by 0.1 μM CPT+10 μM compound 32) indicates a significant decrease in NF-κB-DNA complex formation.

Imidazolines 28-33 were evaluated for their ability to enhance the activity of camptothecin in CEM cells. Induction of apoptosis is the hallmark of most chemotherapeutic agents including camptothecin. The systematic disassembly of apoptotic cells is accomplished by active caspases (Thornberry et al., Nature 356: 768-774 (1992); Nicholson et al., Trends Biochem. Sci. 22: 299-306 (1997)). A standard apoptosis assay is Promega's APO-ONE homogeneous caspase-3/7 assay, which takes advantage of this caspase activity to directly quantify the induction of apoptosis in cells (Thornberry et al., Nature 356: 768-774 (1992); Nicholson et al., Trends Biochem. Sci. 22: 299-306 (1997)). According to the hypothesis that NF-κB inhibition should enhance the activity of chemotherapeutic agents via the inhibition of anti-apoptotic signaling pathway—thus enhancement of apoptosis—(Boland, Biochem Soc Trans 29: 674-678 (2001); Chiao et al., Cancer 95: 1696-1705 (2002)), we investigated the effects of the imidazolines using this caspase-3/7 assay. This assay quantifies the level of apoptotic cell death induced by camptothecin with and without the imidazolines and will establish the direct level of enhancement of apoptosis by camptothecin. Representative cell death graphs are shown in FIGS. 13A-F.

The graphs illustrate two very important biological effects. The imidazolines appear to be non-toxic (or at least exhibit no significant cytotoxic effects in the CEM cells) as illustrate by the drug (imidazoline) only line (black triangle). The imidazolines appear to significantly induce apoptosis when the agents are used in combination with the topoisomerase inhibitor, camptothecin (CPT) (line with X versus CPT only line with square). The concentration of camptothecin was kept constant at 0.1 μM in all experiments and a significant, dose-time response induction of apoptosis was noted upon combinational treatment with the imidazolines.

TABLE 11

| Compound (1.0 μM) | Apoptosis ±S.D. | Fold enhancement of camptothecin (0.1 μM) after 48 hours |
|---|---|---|
| Cells only | 1.00 (normalized) | |
| 28 | 1.25 ± (0.18) | |
| 29 | 0.95 ± (0.24) | |
| 30 | 1.18 ± (0.20) | |
| 31 | 1.18 ± (0.00)[b] | |
| 32 | 1.98 ± (0.0001) | |
| CPT (0.1 μM) | 3.17 ± (1.35) | 1.00 |
| CPT + 28 | 4.55 ± (0.83) | 1.44 |
| CPT + 29 | 7.32 ± (0.93) | 2.26 |
| CPT + 30 | 7.15 ± (0.11) | 2.31 |
| CPT + 31 | 7.74 ± (0.00)[b] | 2.44 |
| CPT + 32 | 12.63 ± (0.85)[a] | 3.98 |

[a]Complete set of data shown in FIG. 13A-F.
[b]Data from single experiment.

Figure 14:
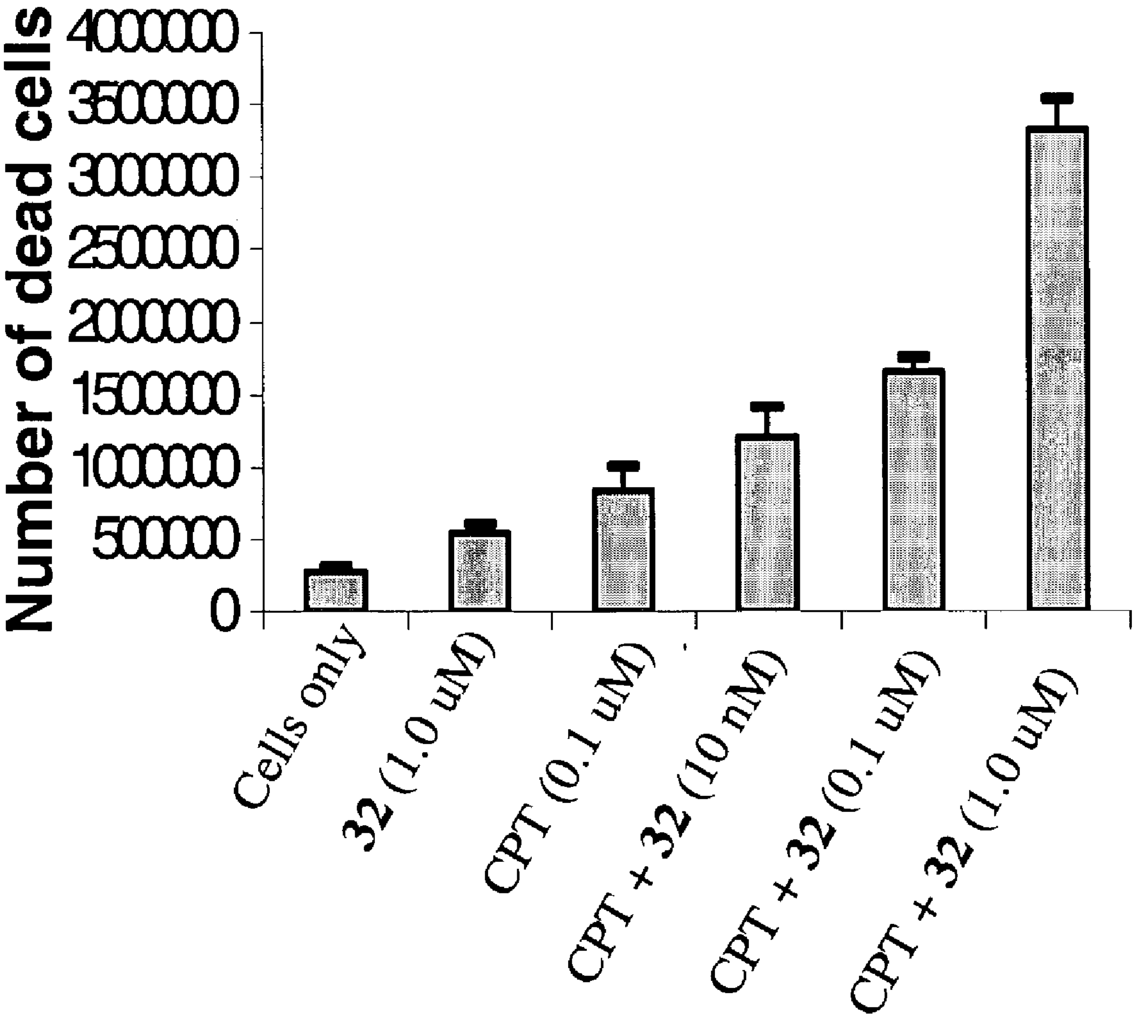
FIG. 14 is a chart showing the dose dependent enhancement of apoptosis measured after 48 hours in combinatorial treatment of CPT (0.1 μM) with varying concentrations of imidazoline 32.

One of the most active compounds in the series, thus far, is the triphenyl substituted benzyl imidazoline 32. The imidazoline 32 at 1.0 μM enhanced the camptothecin-induced level of apoptosis 4 fold (see Table 11 and FIG. 14).

No significant induction of cell death was observed when cells were treated with only the imidazolines up to 1.0 μM over 48 hours in this apoptosis (caspase-3) assay as well as tested by cell count up to 10 μM over 72 hours (data not shown). A summary of our results of the induction of apoptosis by several other imidazolines is depicted in Table 11.

This was determined by the number of apoptotic cell death after 48 hours after treatment of CEM cells with 0.1 μM camptothecin (CPT) compared to number of dead cells after a combinational treatment of 0.1 μM camptothecin (CPT) and 1.0 μM imidazoline 32.

Figure 15A:
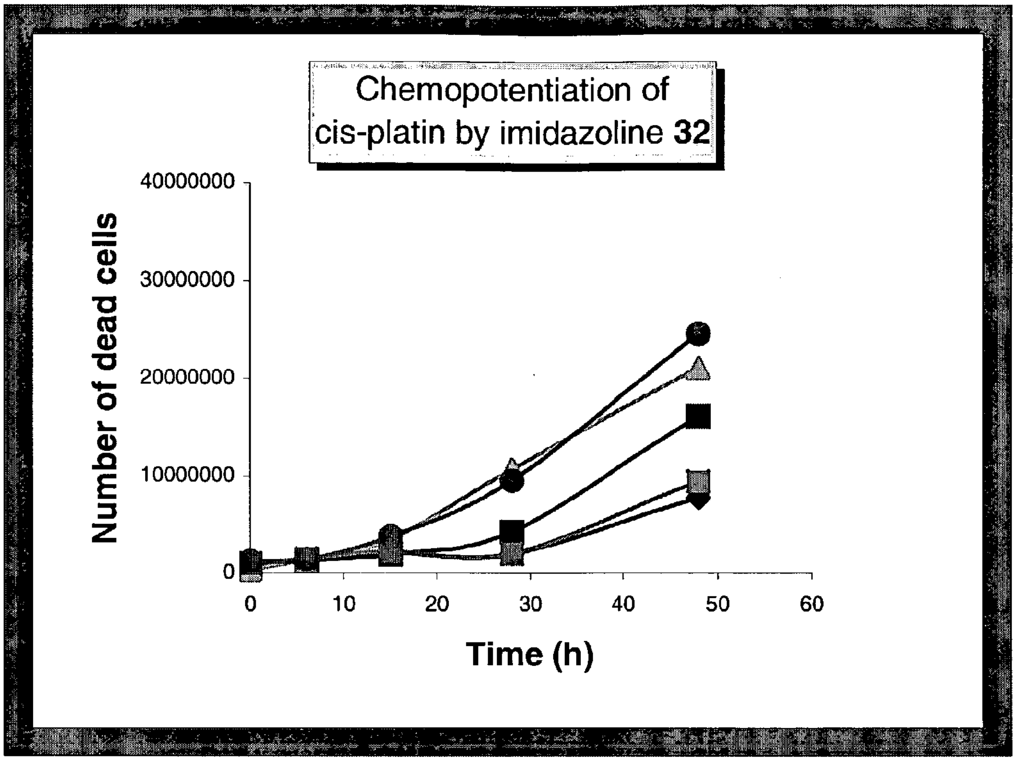
FIG. 15A shows the chemopotentiation of cis-platin by imidazoline 32. ● is 0.1 μM cis-platin and 0.1 μM imidiazoline 32; ▲ is 1.0 μM cis-platin; ■ is 0.01 μM cis-platin; ♦ is 10 μM imidazoline 32.
Figure 15B:
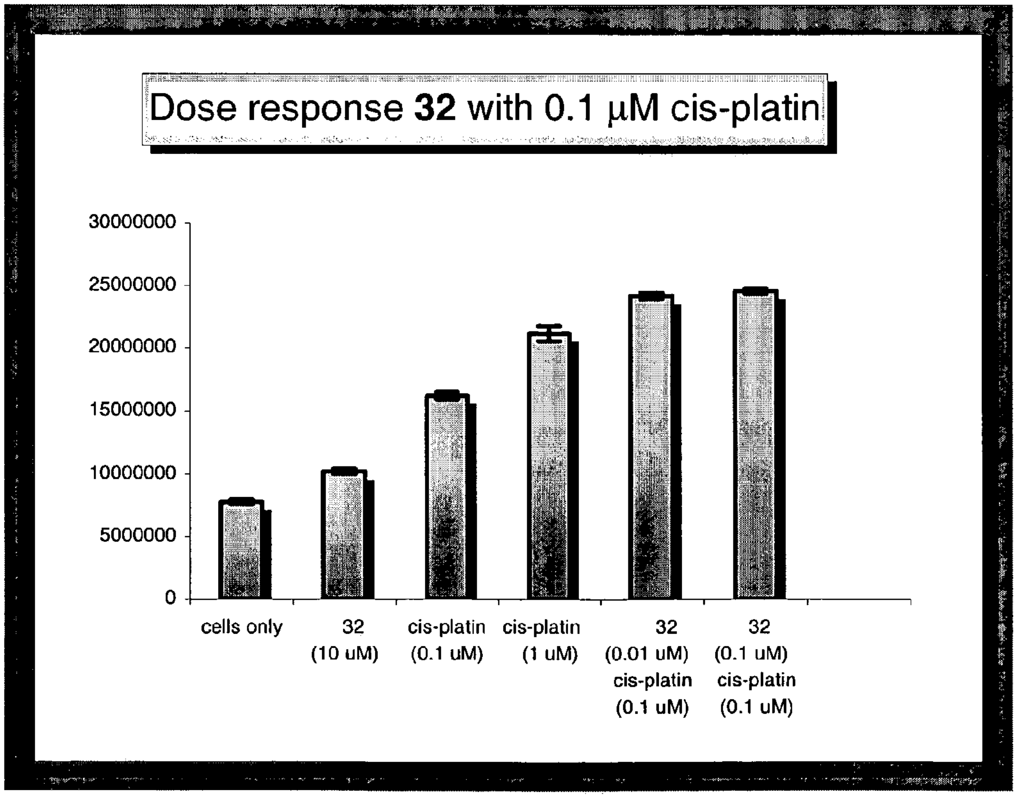
FIG. 15B is a chart showing dose responses of imidazoline 32 with 0.1 μM cis-platin.

In a similar experiment, the imidazoline 32 was found to chemopotentiate cis-platin (FIGS. 15A and 15B). Combination of 0.1 micromolar cis-platin with 0.1 micromolar 32 was found induce more apoptosis in T-cells (CEM cells) that 1.0 micromolar of cis-platin (a 10-fold increase) by itself.

Materials and Methods

EMSA assay for NF-κB-DNA binding was as follows. Human Jurkat leukemia T-cells (clone E6-1; Amer. Type Culture Collection, Rockville, Md.) were grown in RPMI-1640 Media (Gibco-BRL, Rockville, Md.) supplemented with 10% fetal bovine serum, penicillin (614 ηg/mL), streptomycin (10 μg/mL) and HEPES buffer, pH 7.2 at 37° C., 5% $CO_2$. The Jurkat cells ($1\times10^6$ cells/mL) were subsequently treated with various concentrations of the compounds for 30 minutes at 37° C. and 5% $CO_2$ followed by PMA (50 ng/mL) and PHA (1 mM/mL) stimulation for an additional 30 minutes. The cells were harvested by centrifugation, washed in ice cold PBS and the nuclear extracts were prepared as previously described (Dignam, et al., Nucl. Acids Res 11: 1475-1489 (1983)). The protein concentration of the extracts was determined according to the Method of Bradford (1976) with BioRad reagents. Nuclear extracts are incubated for 20 minutes at room temperature with a double stranded Cy3 labeled NF-kB consensus oligonucleotide, 5'-AGT-TGAGGGGACTTTC CCAGGC-3' (SEQ ID NO:1). The binding mixture (25 mL) contained 10 mM HEPES-NaOH pH 7.9, 4 mM tris-HCl, pH 7.9, 6.0 mM KCl, 1 mM EDTA, 1 mM DTT, 10% glycerol, 0.3 mg/mL bovide serum albumin and 1 mg of poly (dI.dC). The binding mixtures (10 mg of nuclear extract protein) were incubated for 20 minutes at room temrperature with 0.16 pmol of Cy3 labeled oligonucleotide. The mixture was loaded on a 4% polyacrylamide gel prepared in 1× tris borate/EDTA buffer and was electrophoresed at 200 V for 20 minutes. After electrophoresis the gel was analyzed using a phosphorimager (Biorad FX plus) for detection of the NF-kB—DNA binding.

Inhibition of translocation with p65-ELISA assay was as follows. The quantity of p65/p50 heterodimer that has translocated into the nucleus was measured using a NF-κB p65 sandwich ELISA assay (Imgenex Corp.). Jurkat cells were grown to $2\times10^6$ cells/mL and treated with 50 ng/mL PMA and 1 μg/mL PMA/PHA and incubated at 37° C., 5% $CO_2$. The cells are harvested after 30 minutes and nuclear extracts are prepared as previously described by Dignam and coworkers (Dignam, et al., Nucl. Acids Res 11: 1475-1489 (1983)). The NF-κB p65 sandwich ELISA kit was then used to monitor and quantify p65 translocation into the nucleus according to the manufacturers protocol. PDTC is reported to be an inhibitor of NF-κB translocation and our data confirmed that it inhibited NF-κB translocation at concentrations ranging from 100 nM to 5.0 μM.

Induction of apoptosis using caspase 3/7 assay was as follows. CEM cells (CCRF-CEM); Amer. Type Culture Collection, Rockville, Md.) were grown in RPMI-1640 Media (Gibco-BRL, Rockville, Md.) supplemented with 10% fetal bovine serum, penicillin (614 ηg/mL), streptomycin (10 μg/mL) and hepes buffer, pH 7.2 at 37° C., 5% $CO_2$. DMSO was used as the vector for all drugs and added in the control experiments. Cell cultures were treated with 1 μM, 0.1 μM or 10 nM of the imidazolines and allowed to incubate at 37° C., 5% $CO_2$. An aliquote was transferred to a 96-well plate and mixed with an equal volume of Apo-ONE™ Homogenous Caspase-3/7 assay (Promega Corporation) reagent. The contents of the plate were gently mixed and allowed to incubate for 1 hour. The fluorescence of each well was then measured on a Molecular Imager FX Pro at 532 nm. All reported data was the average of two independent experiments unless otherwise indicated.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for enhancing the effect of known antiproliferative drugs in a mammal wherein the effect is enhancement of apoptosis which comprises administering an imidazoline of the formula:

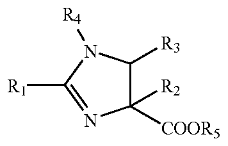

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; and $R_5$ is selected from the group consisting of hydrogen and an alkyl group, all of which are optionally substituted, in conjunction with the antiproliferative drug selected from the group consisting of a platinate and a camptothecin to the mammal.

2. The method of claim 1 wherein the mammal is human.

3. The method of any one of claims 1 or 2, wherein the administration is orally to the mammal.

4. The method of any one of claims 1 or 2, wherein the administration is topically to the mammal.

5. The method of any one of claim 1 or 2, wherein the administration is by injection into the mammal.

6. The method of any one of claim 1 or 2, wherein the administration is intravenous into the mammal.

7. The method of claim 1 wherein the imidazoline is dl-(4S,5S)-1-benzyl-2,4,5-triphenyl-4,5-dihydro-1-1H-imidazole-4-carboxylic acid.

* * * * *